(12) United States Patent
Wikström et al.

(10) Patent No.: US 12,059,424 B2
(45) Date of Patent: Aug. 13, 2024

(54) PHARMACEUTICAL COMPOSITIONS COMPRISING (2S)-N-{(1S)-1-CYANO-2-[4-(3-METHYL-2-OXO-2,3-DIHYDRO-1,3-BENZOXAZOL-5-YL) PHENYL]ETHYL}-1,4-OXAZEPANE-2-CARBOXAMIDE

(71) Applicant: ASTRAZENECA AB, Södertälje (SE)

(72) Inventors: Håkan Wikström, Mölndal (SE); Jufang Wu Ludvigsson, Mölndal (SE); Thomas Andersson, Mölndal (SE)

(73) Assignee: AstraZeneca AB, Södertälje (SE)

(*) Notice: Subject to any disclaimer, the term of this patent is extended or adjusted under 35 U.S.C. 154(b) by 357 days.

(21) Appl. No.: 16/975,292

(22) PCT Filed: Mar. 1, 2019

(86) PCT No.: PCT/EP2019/055138
§ 371 (c)(1),
(2) Date: Aug. 24, 2020

(87) PCT Pub. No.: WO2019/166626
PCT Pub. Date: Sep. 6, 2019

(65) Prior Publication Data
US 2021/0369732 A1  Dec. 2, 2021

Related U.S. Application Data

(60) Provisional application No. 62/636,944, filed on Mar. 1, 2018.

(51) Int. Cl.
| | | |
|---|---|---|
| A61K 31/553 | (2006.01) | |
| A61K 9/20 | (2006.01) | |
| A61K 31/675 | (2006.01) | |
| A61K 45/06 | (2006.01) | |
| C07K 16/24 | (2006.01) | |
| C07K 16/28 | (2006.01) | |

(52) U.S. Cl.
CPC .......... *A61K 31/553* (2013.01); *A61K 9/2009* (2013.01); *A61K 9/2013* (2013.01); *A61K 9/2054* (2013.01); *A61K 9/2059* (2013.01); *A61K 31/675* (2013.01); *A61K 45/06* (2013.01); *C07K 16/241* (2013.01); *C07K 16/2887* (2013.01)

(58) Field of Classification Search
CPC .. A61K 31/553; A61K 9/2009; A61K 9/2013; A61K 9/2054; A61K 9/2059; A61K 31/675; A61K 45/06; C07K 16/241; C07K 16/2887
USPC ....................................................... 514/211
See application file for complete search history.

(56) References Cited

U.S. PATENT DOCUMENTS

| | | | |
|---|---|---|---|
| 8,552,034 B2 * | 10/2013 | Verwijs .................. | A61P 19/08 |
| | | | 546/283.7 |
| 8,871,783 B2 | 10/2014 | Anderskewitz et al. | |
| 8,877,775 B2 | 11/2014 | Anderskewitz et al. | |
| 8,889,708 B2 | 11/2014 | Grauert et al. | |
| 8,987,249 B2 | 3/2015 | Anderskewitz et al. | |
| 8,999,975 B2 | 4/2015 | Grundl et al. | |
| 9,073,869 B2 | 7/2015 | Anderskewitz et al. | |
| 9,440,960 B2 | 9/2016 | Grauert et al. | |
| 9,522,894 B2 * | 12/2016 | Lonn ....................... | A61P 31/06 |
| 9,713,606 B2 | 7/2017 | Anderskewitz et al. | |
| 9,815,805 B2 | 11/2017 | Lonn et al. | |
| 9,856,228 B2 | 1/2018 | Lauritzen et al. | |
| 9,879,026 B2 | 1/2018 | Vintonyak et al. | |
| 10,238,633 B2 | 3/2019 | Anderskewitz et al. | |
| 10,287,258 B2 | 5/2019 | Lonn et al. | |
| RE47,636 E | 10/2019 | Vintonyak et al. | |
| 10,479,781 B2 | 11/2019 | Lauritzen et al. | |
| 10,669,245 B2 | 6/2020 | Lonn et al. | |
| 11,117,874 B2 | 9/2021 | Lonn et al. | |
| 11,655,221 B2 | 5/2023 | Lönn et al. | |
| 11,655,222 B2 | 5/2023 | Lönn et al. | |
| 11,655,223 B2 | 5/2023 | Lönn et al. | |
| 11,655,224 B2 | 5/2023 | Lönn et al. | |
| 11,667,615 B2 | 6/2023 | Lonn et al. | |
| 11,673,871 B2 | 6/2023 | Lönn et al. | |
| 11,673,872 B2 | 6/2023 | Lönn et al. | |
| 11,680,049 B2 | 6/2023 | Lönn et al. | |
| 11,773,069 B2 | 10/2023 | Lönn et al. | |
| 2008/0221093 A1 | 9/2008 | Gege et al. | |
| 2012/0315271 A1 | 12/2012 | Shelton et al. | |

(Continued)

FOREIGN PATENT DOCUMENTS

| | | |
|---|---|---|
| CN | 101945851 A | 1/2011 |
| CN | 102574830 A | 7/2012 |

(Continued)

OTHER PUBLICATIONS

Golchert D, Bines E, Carmody A. Evaluation of some compression aids in tableting of roller compacted swellable core drug layer. Int J Pharm. Sep. 10, 2013;453(2):322-8. doi: 10.1016/j.ijpharm.2013. 06.025. Epub Jun. 21, 2013. PMID: 23796839 (Year: 2013).*
Karthik VV. Excipients Used in the Formulation of Tablets. RRJCHEM. Jun. 2016; 5(2); 143-154. e-ISSN: 2319-9849 (Year: 2016).*
NCT03218917 (https://clinicaltrials.gov/;) Randomized, Double-Blind, Placebo-Controlled, Parallel-Group, Multi-Center Study of Efficacy, Safety & Tolerability, and Pharmacokinetics of INS1007 Administered Daily for 24 Weeks in Non-Cystic Fibrosis Bronchiectasis—The Willow Study, Jul. 12, 2017. (Year: 2017).*

(Continued)

*Primary Examiner* — Jared Barsky
*Assistant Examiner* — Liyuan Mou
(74) *Attorney, Agent, or Firm* — Cooley LLP

(57) ABSTRACT

The present disclosure relates to pharmaceutical compositions suitable for oral administration, and more particularly to pharmaceutical compositions, including pharmaceutical tablet compositions, containing (2S)-N-{(1S)-1-cyano-2-[4-(3-methyl-2-oxo-2,3-dihydro-1,3-benzoxazol-5-yl)phenyl] ethyl}-1,4-oxazepane-2-carboxamide (Compound A) or a pharmaceutically acceptable salt thereof.

8 Claims, 12 Drawing Sheets

(56) References Cited

U.S. PATENT DOCUMENTS

| | | |
|---|---|---|
| 2012/0329775 A1 | 12/2012 | Ford et al. |
| 2014/0275159 A1 | 9/2014 | Anderskewitz et al. |
| 2015/0025058 A1 | 1/2015 | Deutsch et al. |
| 2015/0105375 A1 | 4/2015 | Anderskewitz et al. |
| 2015/0210655 A1 | 7/2015 | Lonn et al. |
| 2015/0224199 A1* | 8/2015 | De Weer ............... A61P 43/00 514/228.5 |
| 2015/0346203 A1 | 12/2015 | Xu et al. |
| 2016/0061824 A1 | 3/2016 | Hahn et al. |
| 2016/0324854 A1* | 11/2016 | Finnie ................... A61K 9/2054 |
| 2017/0027907 A1* | 2/2017 | Legangneux .......... A61K 9/2018 |
| 2017/0057938 A1 | 3/2017 | Lonn et al. |
| 2018/0028541 A1 | 2/2018 | Lonn et al. |
| 2018/0044328 A1 | 2/2018 | Lauritzen et al. |
| 2018/0169017 A1 | 6/2018 | Desai et al. |
| 2018/0251436 A1 | 9/2018 | Lonn et al. |
| 2019/0091236 A1 | 3/2019 | Lonn et al. |
| 2019/0167636 A1 | 6/2019 | Anderskewitz et al. |
| 2019/0247400 A1 | 8/2019 | Dipetrillo et al. |
| 2020/0017455 A1 | 1/2020 | Lonn et al. |
| 2020/0138780 A1 | 5/2020 | Anderskewitz et al. |
| 2020/0179398 A1 | 6/2020 | Lonn et al. |
| 2020/0247765 A1 | 8/2020 | Lonn et al. |
| 2020/0390781 A1 | 12/2020 | Dipetrillo et al. |
| 2021/0186931 A1 | 6/2021 | Davidson et al. |
| 2021/0186984 A1 | 6/2021 | Dipetrillo et al. |
| 2021/0238152 A1 | 8/2021 | Lonn et al. |
| 2021/0252015 A1 | 8/2021 | Zhang |
| 2021/0322438 A1 | 10/2021 | Zhang |
| 2022/0133737 A1 | 5/2022 | Lonn et al. |
| 2023/0025351 A1 | 1/2023 | Lönn et al. |
| 2023/0028726 A1 | 1/2023 | Lönn et al. |
| 2023/0033573 A1 | 2/2023 | Lönn et al. |
| 2023/0062646 A1 | 3/2023 | Lönn et al. |
| 2023/0069044 A1 | 3/2023 | Lönn et al. |
| 2023/0085620 A1 | 3/2023 | Lönn et al. |
| 2023/0115170 A1 | 4/2023 | Lönn et al. |
| 2023/0116721 A1 | 4/2023 | Lönn et al. |
| 2023/0250071 A1 | 8/2023 | Lönn et al. |
| 2023/0278969 A1 | 9/2023 | Lönn et al. |

FOREIGN PATENT DOCUMENTS

| | | |
|---|---|---|
| EP | 1317555 B1 | 11/2007 |
| EP | 2840083 A1 | 2/2015 |
| JP | 2006527704 A | 12/2006 |
| JP | 2008501692 A | 1/2008 |
| JP | 2008504307 A | 2/2008 |
| JP | 2010540526 A | 12/2010 |
| JP | 2011506421 A | 3/2011 |
| JP | 2011522011 A | 7/2011 |
| JP | 2012522764 A | 9/2012 |
| JP | 2012526093 A | 10/2012 |
| JP | 2016515576 A | 5/2016 |
| JP | 2017503832 A | 2/2017 |
| JP | 2019070029 A | 5/2019 |
| JP | 2021046423 A | 3/2021 |
| TW | 201041889 A | 12/2010 |
| WO | WO 1999/017777 | 4/1999 |
| WO | WO 2001/016108 | 3/2001 |
| WO | WO 2001/096285 | 12/2001 |
| WO | WO 2002/051831 | 7/2002 |
| WO | WO 2003/048123 | 6/2003 |
| WO | WO-2004076434 A1 | 9/2004 |
| WO | WO 2004/087153 | 10/2004 |
| WO | WO 2004/110988 | 12/2004 |
| WO | WO-2004106289 A1 | 12/2004 |
| WO | WO 2005/107762 | 11/2005 |
| WO | WO-2005106012 A2 | 11/2005 |
| WO | WO-2005120465 A2 | 12/2005 |
| WO | WO-2006000228 A2 | 1/2006 |
| WO | WO 2006/020145 | 2/2006 |
| WO | WO 2007/005668 | 1/2007 |
| WO | WO 2008/109180 | 9/2008 |
| WO | WO 2008/109181 | 9/2008 |
| WO | WO 2009/026701 | 3/2009 |
| WO | WO-2009042187 A1 | 4/2009 |
| WO | WO 2009/074829 | 6/2009 |
| WO | WO-2009147238 A1 | 12/2009 |
| WO | WO 2010/077680 | 7/2010 |
| WO | WO-2010114405 A2 | 10/2010 |
| WO | WO 2010/128324 | 11/2010 |
| WO | WO 2010/142985 | 12/2010 |
| WO | WO 2011/154677 | 12/2011 |
| WO | WO 2012/064715 | 5/2012 |
| WO | WO 2012/119941 | 9/2012 |
| WO | WO 2013/041497 | 3/2013 |
| WO | WO 2014/091443 | 6/2014 |
| WO | WO 2014/140075 | 9/2014 |
| WO | WO 2014/140081 | 9/2014 |
| WO | WO 2014/140091 | 9/2014 |
| WO | WO 2014/151784 | 9/2014 |
| WO | WO-2014165303 A1 | 10/2014 |
| WO | WO 2015/032942 | 3/2015 |
| WO | WO 2015/032943 | 3/2015 |
| WO | WO 2015/032945 | 3/2015 |
| WO | WO 2015/110826 | 7/2015 |
| WO | WO-2015175939 A1 | 11/2015 |
| WO | WO 2016/075240 | 5/2016 |
| WO | WO 2018/022978 | 2/2018 |
| WO | WO 2019/157050 | 8/2019 |
| WO | WO-2019166626 A1 | 9/2019 |
| WO | WO 2020/018547 | 1/2020 |
| WO | WO 2020/018551 | 1/2020 |
| WO | WO-2020247665 A1 | 12/2020 |
| WO | WO-2022140516 A1 | 6/2022 |
| WO | WO-2022232420 A1 | 11/2022 |
| WO | WO-2022232573 A1 | 11/2022 |

OTHER PUBLICATIONS

Ludvigsson et al. Journal of Pharmaceutical and Biomedical Analysis 158 (2018) 82-87, "Degradation caused by incompatibility between sodium stearyl fumarate (PRUV) and AZD7986 in the drug product" (Year: 2018).*

Wang et al. European Journal of Pharmaceutics and Biopharmaceutics 75 (2010), 1-15, "Lubrication in tablet formulations" (Year: 2010).*

Li et al. Lubricants Feb. 2014, 21-43; doi: 10.3390/lubricants2010021, "Lubricants in Pharmaceutical Solid Dosage Forms" (Year: 2014).*

Alpsoy, E. (Apr. 2005), "Behcet's Disease: Treatment of Mucocutaneous Lesions," Clinical and Experimental Rheumatology, vol. 23, No. 4, pp. 532-539.

Avci, D. (Feb. 2019), "Dipeptidyl Peptidase-4 Inhibitors and Inflammation: Dpp-4 Inhibitors Improve Mean Pleatelet Volume and Gamma Glutamyl Transferase Level," Journal of Biosciences and Medicines, vol. 7, No. 2, pp. 42-53.

Bae, S. et al. (Jul. 2012), "Elevated interleukin-32 expression in granulomatosis with polyangiitis," Rheumatology 2012;51:1979-1988, doi:10.1093/rheumatology/kes163, Advance Access publication.

Chalmers, J. D. et al. (Mar. 2014), "The Bronchiectasis Severity Index. An International Derivation and Validation Study," Am. J. Respir. Crit. Care Med., 189(5):576-585.

Everts-Graber, J. et al. (2019), "Proteomic analysis of neutrophils in ANCA-associated vasculitis reveals a dysregulation in proteinase 3-associated proteins such as annexin-A1 involved in apoptotic cell clearance," Kidney International 96, 397-408; https://doi.org/10.1016/j.kint.2019.02.017.

Extended European Search Report for European Application No. 19751012.6, dated Oct. 4, 2021, 7 pages.

Extended European Search Report for European Application No. 19837016.5, mailed Mar. 18, 2022, 10 pages.

Extended European Search Report for European Application No. 19838400.0, mailed Mar. 24, 2022, 9 pages.

Goeminne, P. C. et al. (Feb. 2014), "Mortality in non-cystic fibrosis bronchiectasis: A prospective cohort analysis," Respir. Med., 108(2):287-296.

International Search Report and Written Opinion for International Application No. PCT/US2021/064810, mailed Mar. 16, 2022, 8 pages.

(56) References Cited

OTHER PUBLICATIONS

International Search Report and Written Opinion for International Application No. PCT/US2022/026769, mailed Sep. 9, 2022, 15 pages.
International Search Report and Written Opinion for International Application No. PCT/US2022/027026, mailed Sep. 14, 2022, 11 pages.
Invitation to Pay Additional Fees for International Application No. PCT/US2022/026769, mailed Jun. 27, 2022, 3 pages.
Invitation to Pay Additional Fees for International Application No. PCT/US2022/027026, mailed Jul. 8, 2022, 2 pages.
Jones, B. E. et al. (2017), "Gene-Specific DNA Methylation Changes Predict Remission in Patients with ANCA-Associated Vasculitis," J Am Soc Nephrol 28: 1175-1187. doi: 10.1681/ASN.2016050548.
Kelly, M. G. et al. (Sep. 2003), "Bronchiectasis in secondary care: A comprehensive profile of a neglected disease," Eur. J. Intern. Med., 14(8):488-492.
Kono, H., et al. (Oct. 2012), "The IL-1-dependent sterile inflammatory response has a substantial caspase-1-independent component that requires cathepsin C," The Journal of Immunology, vol. 189, No. 7, pp. 3734-3740.
Schreiber, A. et al. (Mar. 2012), "Neutrophil serine proteases promote IL-1β generation and injury in necrotizing crescentic glomerulonephritis," Journal of the American Society of Nephrology, vol. 23, No. 3, pp. 470-482.
Clinical Trials Identifier: NCT03218917, ClinicalTrials.gov submitted on Aug. 15, 2017, 5 pages.
Clinical Trials Identifier: NCT03218917, ClinicalTrials.gov submitted on Aug. 20, 2018, 17 pages.
Clinical Trials Identifier: NCT03218917, ClinicalTrials.gov submitted on Dec. 11, 2020, 10 pages.
Clinical Trials Identifier: NCT03218917, ClinicalTrials.gov submitted on Dec. 17, 2018, 17 pages.
Clinical Trials Identifier: NCT03218917, ClinicalTrials.gov submitted on Dec. 17, 2019, 10 pages.
Clinical Trials Identifier: NCT03218917, ClinicalTrials.gov submitted on Dec. 4, 2019, 10 pages.
Clinical Trials Identifier: NCT03218917, ClinicalTrials.gov submitted on Dec. 8, 2018, 17 pages.
Clinical Trials Identifier: NCT03218917, ClinicalTrials.gov submitted on Feb. 11, 2019, 17 pages.
Clinical Trials Identifier: NCT03218917, ClinicalTrials.gov submitted on Feb. 12, 2019, 17 pages.
Clinical Trials Identifier: NCT03218917, ClinicalTrials.gov submitted on Feb. 5, 2018, 5 pages.
Clinical Trials Identifier: NCT03218917, ClinicalTrials.gov submitted on Jan. 14, 2019, 17 pages.
Clinical Trials Identifier: NCT03218917, ClinicalTrials.gov submitted on Jan. 28, 2019, 17 pages.
Clinical Trials Identifier: NCT03218917, ClinicalTrials.gov submitted on Jan. 3, 2019, 17 pages.
Clinical Trials Identifier: NCT03218917, ClinicalTrials.gov submitted on Jan. 31, 2019, 17 pages.
Clinical Trials Identifier: NCT03218917, ClinicalTrials.gov submitted on Jul. 12, 2017, 7 pages.
Clinical Trials Identifier: NCT03218917, ClinicalTrials.gov submitted on Jul. 30, 2018, 5 pages.
Clinical Trials Identifier: NCT03218917, ClinicalTrials.gov submitted on Mar. 28, 2019, 16 pages.
Clinical Trials Identifier: NCT03218917, ClinicalTrials.gov submitted on May 28, 2019, 10 pages.
Clinical Trials Identifier: NCT03218917, ClinicalTrials.gov submitted on Nov. 13, 2018, 17 pages.
Clinical Trials Identifier: NCT03218917, ClinicalTrials.gov submitted on Nov. 28, 2018, 17 pages.
Clinical Trials Identifier: NCT03218917, ClinicalTrials.gov submitted on Nov. 6, 2018, 17 pages.
Clinical Trials Identifier: NCT03218917, ClinicalTrials.gov submitted on Oct. 16, 2018, 17 pages.
Clinical Trials Identifier: NCT03218917, ClinicalTrials.gov submitted on Sep. 12, 2018, 17 pages.
Clinical Trials Identifier: NCT03218917, ClinicalTrials.gov submitted on Sep. 24, 2018, 17 pages.
Clinical Trials Identifier: NCT04594369. ClinicalTrials.gov submitted on Apr. 12, 2022, 33 pages.
Clinical Trials Identifier: NCT04594369. ClinicalTrials.gov submitted on Apr. 22, 2021, 14 pages.
Clinical Trials Identifier: NCT04594369. ClinicalTrials.gov submitted on Apr. 22, 2022, 32 pages.
Clinical Trials Identifier: NCT04594369. ClinicalTrials.gov submitted on Apr. 5, 2022, 32 pages.
Clinical Trials Identifier: NCT04594369. ClinicalTrials.gov submitted on Apr. 9, 2021, 13 pages.
Clinical Trials Identifier: NCT04594369. ClinicalTrials.gov submitted on Aug. 1, 2022, 32 pages.
Clinical Trials Identifier: NCT04594369. ClinicalTrials.gov submitted on Aug. 18, 2022, 32 pages.
Clinical Trials Identifier: NCT04594369. ClinicalTrials.gov submitted on Aug. 23, 2021, 24 pages.
Clinical Trials Identifier: NCT04594369. ClinicalTrials.gov submitted on Aug. 30, 2022, 32 pages.
Clinical Trials Identifier: NCT04594369. ClinicalTrials.gov submitted on Aug. 9, 2021, 23 pages.
Clinical Trials Identifier: NCT04594369. ClinicalTrials.gov submitted on Dec. 1, 2020, 6 pages.
Clinical Trials Identifier: NCT04594369. ClinicalTrials.gov submitted on Dec. 10, 2020, 6 pages.
Clinical Trials Identifier: NCT04594369. ClinicalTrials.gov submitted on Dec. 3, 2021, 28 pages.
Clinical Trials Identifier: NCT04594369. ClinicalTrials.gov submitted on Jul. 11, 2022, 32 pages.
Clinical Trials Identifier: NCT04594369. ClinicalTrials.gov submitted on Jul. 23, 2021, 21 pages.
Clinical Trials Identifier: NCT04594369. ClinicalTrials.gov submitted on Jul. 27, 2022, 32 pages.
Clinical Trials Identifier: NCT04594369. ClinicalTrials.gov submitted on Jul. 9, 2021, 21 pages.
Clinical Trials Identifier: NCT04594369. ClinicalTrials.gov submitted on Jun. 20, 2022, 32 pages.
Clinical Trials Identifier: NCT04594369. ClinicalTrials.gov submitted on Jun. 21, 2021, 19 pages.
Clinical Trials Identifier: NCT04594369. ClinicalTrials.gov submitted on Jun. 24, 2021, 19 pages.
Clinical Trials Identifier: NCT04594369. ClinicalTrials.gov submitted on Jun. 30, 2021, 20 pages.
Clinical Trials Identifier: NCT04594369. ClinicalTrials.gov submitted on Jun. 7, 2021, 19 pages.
Clinical Trials Identifier: NCT04594369. ClinicalTrials.gov submitted on Jun. 7, 2022, 32 pages.
Clinical Trials Identifier: NCT04594369. ClinicalTrials.gov submitted on Mar. 11, 2021, 9 pages.
Clinical Trials Identifier: NCT04594369. ClinicalTrials.gov submitted on Mar. 13, 2022, 33 pages.
Clinical Trials Identifier: NCT04594369. ClinicalTrials.gov submitted on Mar. 25, 2021, 11 pages.
Clinical Trials Identifier: NCT04594369. ClinicalTrials.gov submitted on Mar. 25, 2022, 31 pages.
Clinical Trials Identifier: NCT04594369. ClinicalTrials.gov submitted on Mar. 25, 2022, 34 pages.
Clinical Trials Identifier: NCT04594369. ClinicalTrials.gov submitted on Mar. 4, 2022, 32 pages.
Clinical Trials Identifier: NCT04594369. ClinicalTrials.gov submitted on Nov. 10, 2021, 29 pages.
Clinical Trials Identifier: NCT04594369. ClinicalTrials.gov submitted on Nov. 15, 2022, 30 pages.
Clinical Trials Identifier: NCT04594369. ClinicalTrials.gov submitted on Nov. 19, 2022, 6 pages.
Clinical Trials Identifier: NCT04594369. ClinicalTrials.gov submitted on Nov. 23, 2022, 30 pages.
Clinical Trials Identifier: NCT04594369. ClinicalTrials.gov submitted on Oct. 10, 2022, 31 pages.

(56) References Cited

OTHER PUBLICATIONS

Clinical Trials Identifier: NCT04594369. ClinicalTrials.gov submitted on Oct. 14, 2022, 6 pages.
Clinical Trials Identifier: NCT04594369. ClinicalTrials.gov submitted on Oct. 27, 2022, 31 pages.
Clinical Trials Identifier: NCT04594369. ClinicalTrials.gov submitted on Oct. 28, 2022, 29 pages.
Clinical Trials Identifier: NCT04594369. ClinicalTrials.gov submitted on Oct. 29, 2022, 29 pages.
Clinical Trials Identifier: NCT04594369. ClinicalTrials.gov submitted on Oct. 8, 2021, 28 pages.
Clinical Trials Identifier: NCT04594369. ClinicalTrials.gov submitted on Sep. 12, 2022, 31 pages.
Clinical Trials Identifier: NCT04594369. ClinicalTrials.gov submitted on Sep. 27, 2022, 31 pages.
Clinical Trials Identifier: NCT04594369. ClinicalTrials.gov submitted on Sep. 7, 2021, 25 pages.
Clinical Trials Identifier: NCT04817332. ClinicalTrials.gov submitted on Aug. 12, 2021, 8 pages.
Clinical Trials Identifier: NCT04817332. ClinicalTrials.gov submitted on Mar. 25, 2021, 8 pages.
Clinical Trials Identifier: NCT05090904. ClinicalTrials.gov submitted on Apr. 14, 2022, 6 pages.
Clinical Trials Identifier: NCT05090904. ClinicalTrials.gov submitted on Apr. 5, 2022, 6 pages.
Clinical Trials Identifier: NCT05090904. ClinicalTrials.gov submitted on Aug. 23, 2022, 7 pages.
Clinical Trials Identifier: NCT05090904. ClinicalTrials.gov submitted on Dec. 3, 2021, 6 pages.
Clinical Trials Identifier: NCT05090904. ClinicalTrials.gov submitted on Jul. 27, 2022, 7 pages.
Clinical Trials Identifier: NCT05090904. ClinicalTrials.gov submitted on Jul. 29, 2022, 7 pages.
Clinical Trials Identifier: NCT05090904. ClinicalTrials.gov submitted on Jul. 4, 2022, 7 pages.
Clinical Trials Identifier: NCT05090904. ClinicalTrials.gov submitted on Jun. 22, 2022, 7 pages.
Clinical Trials Identifier: NCT05090904. ClinicalTrials.gov submitted on Jun. 7, 2022, 7 pages.
Clinical Trials Identifier: NCT05090904. ClinicalTrials.gov submitted on Mar. 8, 2022, 6 pages.
Clinical Trials Identifier: NCT05090904. ClinicalTrials.gov submitted on May 13, 2022, 7 pages.
Clinical Trials Identifier: NCT05090904. ClinicalTrials.gov submitted on May 25, 2022, 7 pages.
Clinical Trials Identifier: NCT05090904. ClinicalTrials.gov submitted on Nov. 10, 2022, 7 pages.
Clinical Trials Identifier: NCT05090904. ClinicalTrials.gov submitted on Oct. 12, 2022, 7 pages.
Clinical Trials Identifier: NCT05090904. ClinicalTrials.gov submitted on Oct. 14, 2021, 5 pages.
Clinical Trials Identifier: NCT05090904. ClinicalTrials.gov submitted on Oct. 29, 2021, 5 pages.
Clinical Trials Identifier: NCT05090904. ClinicalTrials.gov submitted on Sep. 9, 2022, 7 pages.
Clinical Trials Identifier: NCT05344508. ClinicalTrials.gov submitted on Apr. 18, 2022, 3 pages.
Clinical Trials Identifier: NCT05344508. ClinicalTrials.gov submitted on Aug. 3, 2022, 3 pages.
Clinical Trials Identifier: NCT05344508. ClinicalTrials.gov submitted on Oct. 6, 2022, 3 pages.
Clinical Trials Identifier: NCT05355935. ClinicalTrials.gov submitted on Apr. 26, 2022, 6 pages.
Clinical Trials Identifier: NCT05355935. ClinicalTrials.gov submitted on Aug. 16, 2022, 6 pages.
Clinical Trials Identifier: NCT05355935. ClinicalTrials.gov submitted on Jul. 27, 2022, 6 pages.
Clinical Trials Identifier: NCT05355935. ClinicalTrials.gov submitted on Jul. 5, 2022, 6 pages.
Clinical Trials Identifier: NCT05355935. ClinicalTrials.gov submitted on Jun. 7, 2022, 6 pages.
Clinical Trials Identifier: NCT05355935. ClinicalTrials.gov submitted on May 16, 2022, 6 pages.
Clinical Trials Identifier: NCT05355935. ClinicalTrials.gov submitted on Oct. 19, 2022, 5 pages.
Clinical Trials Identifier: NCT05355935. ClinicalTrials.gov submitted on Sep. 9, 2022, 6 pages.
Clinical Trials Identifier: NCT05517525. ClinicalTrials.gov submitted on Aug. 24, 2022, 5 pages.
Clinical Trials Identifier: NCT05517525. ClinicalTrials.gov submitted on Nov. 7, 2022, 4 pages.
Clinical Trials Identifier: NCT05517525. ClinicalTrials.gov submitted on Oct. 17, 2022, 4 pages.
Clinical Trials Identifier: NCT05517525. ClinicalTrials.gov submitted on Sep. 21, 2022, 5 pages.
International Search Report and Written Opinion for International Application No. PCT/US2017/044343, mailed Oct. 12, 2017, 7 pages.
Extended European Search Report for European Application No. 17835331.4, mailed Feb. 11, 2020, 8 pages.
International Search Report and Written Opinion for International Application No. PCT/GB2015/050155, mailed Mar. 6, 2015, 7 pages.
Extended European Search Report for European Application No. 17195612.1, mailed Mar. 21, 2018, 5 pages.
Extended European Search Report for European Application No. 20173862.2, mailed Sep. 11, 2020, 7 pages.
International Search Report and Written Opinion for International Application No. PCT/EP2019/055138, mailed Jul. 19, 2019, 11 pages.
International Search Report and Written Opinion for International Application No. PCT/US2019/016844, mailed May 31, 2019, 10 pages.
International Search Report and Written Opinion for International Application No. PCT/US2019/042026, mailed Sep. 4, 2019, 7 pages.
International Search Report and Written Opinion for International Application No. PCT/US2019/042021, mailed Sep. 4, 2019, 7 pages.
Pubchem, CID 134527801, "(2S)-2-[[Hydroxy-[(2S)-1,4-oxazepan-2-yl]methyl]amino]-3-[4-(3-methyl-2-oxo-1,3-benzoxazol-5-yl)phenyl]propanenitrile," Jun. 23, 2018, Retrieved from the Internet: <URL: https://pubchem.ncbi.nlm.nih.gov/compound/134527801>, 6 pages.
Birring, S. S. et al., "Development of a symptom specific health status measure for patients with chronic cough: Leicester Cough Questionnaire (LCQ)," Thorax 2003; 58:339-343.
Bondebjerg, J. et al., "Dipeptidyl nitriles as human dipeptidyl peptidase I inhibitors," Bioorganic & Medicinal Chemistry Letters, vol. 16, No. 13, pp. 3614-3617 (2006).
Doyle, K. et al., "Discovery of second generation reversible covalent DPP1 inhibitors leading to an Oxazepane Amidoacetonitrile based clinical candidate (AZD7986)," Journal of Medicinal Chemistry, 59(20):9457-9472 (Oct. 2016).
Furber, M. et al., "Cathepsin C Inhibitors: Property Optimization and Identification of a Clinical Candidate," Journal of Medicinal Chemistry, 2014, vol. 57, pp. 2357-2367.
Miller, M. R. et al., "Standardisation of spirometry," Eur. Respir. J. 2005; 26:319-338.
Murray, M. P. et al., "Sputum colour: a useful clinical tool in non-cystic fibrosis bronchiectasis," Eur Respir J 2009; 34: 361-364.
Murray, M. P. et al., "Validation of the Leicester Cough Questionnaire in non-cystic fibrosis bronchiectasis," Eur Respir J 2009; 34: 125-131.
Stenton, C., "The MRC breathlessness scale," Occupational Medicine 2008; 58:226-227.
Stockley, R. et al., "Phase II study of a neutrophil elastase inhibitor (AZD9668) in patients with bronchiectasis," Respiratory Medicine, vol. 107, No. 4, Feb. 2013, pp. 524-533.
Korkmaz, B. et al., "Neutrophil Elastase, Proteinase 3, and Cathepsin G as Therapeutic Targets in Human Diseases," Pharmacological Reviews, vol. 62, No. 4, Nov. 2010, pp. 726-759.

(56) References Cited

OTHER PUBLICATIONS

Wickremasinghe, M. et al., "Non-tuberculous mycobacteria in patients with bronchiectasis," Thorax, 60(12): 1045-1051 (2005).
Bragg, R. A. et al., "Aortic Binding of AZD5248: Mechanistic Insight and Reactivity Assays To Support Lead Optimization," Chem Res Toxicol. Oct. 19, 2015;28(10):1991-1999. doi: 10.1021/acs.chemrestox.5b00236. Epub Sep. 16, 2015.
Adkison, A. M. et al., "Dipeptidyl peptidase I activates neutrophil-derived serine proteases and regulates the development of acute experimental arthritis," J. Clin. Invest. 109(3):363-371 (2002).
Suppiah, R. et al., "A cross-sectional study of the Birmingham Vasculitis Activity Score version 3 in systemic vasculitis," Rheumatology 2011;50:899-905.
Floris, A. et al., "Using the Birmingham vasculitis activity score as a screening tool in patients with suspected vasculitis," i174, Apr. 28, 2016, Poster Viewing III, Retrieved from the Internet: < URL: https://academic.oup.com/rheumatology/article-abstract/55/suppl_1/i174/1795586>, Retrieved from the Internet on Apr. 23, 2018, 1 page.
Birmingham Vasculitis Activity Score (version 3), 1 page [No Date].
Cartin-Ceba, R. et al., "Rituximab for Remission Induction and Maintenance in Refractory Granulomatosis With Polyangiitis (Wegener's)," Arthritis & Rheumatism, vol. 64, No. 11, Nov. 2012, pp. 3770-3778.
Dadoniene, J. et al., "Clinical characteristics and long-term survival differences of the ANCA-associated vasculitis group: a cross-sectional study of 27 patients," ACTA Medica Lituanica, 2017, vol. 24, No. 2, pp. 107-112.
Geetha, D. et al., "Current therapy of granulomatosis with polyangiitis and microscopic polyangiitis: the role of rituximab," J Nephrol (2015) 28:17-27.
Guillevin, L. et al., "Microscopic Polyangiitis," Arthritis & Rheumatism, vol. 42, No. 3, Mar. 1999, pp. 421-430.
Insmed, "Insmed Announces Positive Top-Line Results from Phase 2 WILLOW Study of INS1007 in Patients with Non-Cystic Fibrosis Bronchiectasis," Feb. 3, 2020, 5 pages.
Jarrot, P-A et al., "Review Pathogenesis of ANCA-associated vasculitis: An update," Autoimmunity Reviews, vol. 15, Issue 7, Jul. 2016, pp. 704-713.
Jenne, D. E., "Wegener's autoantigen decoded," Nature, vol. 346, Aug. 9, 1990, p. 520.
Jennette, J. C., "Nomenclature and classification of vasculitis: lessons learned from granulomatosis with polyangiitis (Wegener's granulomatosis)," Clinical and Experimental Immunology, 164 (Suppl. 1), 7-10 (2011).
Kallenberg, C. G. M. et al., "Mechanisms of Disease: pathogenesis and treatment of ANCA-associated vasculitides," Nature Clinical Practice Rheumatology, Dec. 2006, vol. 2, No. 12, pp. 661-670.
Keogh, K. A. et al., "Rituximab for Refractory Wegener's Granulomatosis. Report of a Prospective, Open-Label Pilot Trial," Am J Respir Crit Care Med vol. 173. pp 180-187 (2006).
Kettritz, R., "Autoimmunity in kidney diseases," The Scandinavian Journal of Clinical & Laboratory Investigation, vol. 68, No. S241, Jun. 2008, 99-103.
Knopf, A. et al., "Clinical aspects of granulomatosis with polyangiitis affecting the head and neck," Eur Arch Otorhinolaryngol (2015) 272:185-193.
Korkmaz, B. et al., "Neutrophil proteinase 3 and dipeptidyl peptidase I (cathepsin C) as pharmacological targets in granulomatosis with polyangiitis (Wegener granulomatosis)," Semin Immunopathol (2013) 35:411-421.
Lins, L. et al., "SF-36 total score as a single measure of health-related quality of life: Scoping review," SAGE Open Medicine, vol. 4:1-12 (2016).
Luqmani, R. A. et al., "Birmingham Vasculitis Activity Score (BVAS) in Systemic Necrotizing Vasculitis," Q. J. Med. 1994; 87:671-678.
Mukhtyar, C. et al., "Modification and validation of the Birmingham Vasculitis Activity Score (version 3)," Ann Rheum Dis 2009;68:1827-1832.
Pagnoux, C. et al., "Optimal therapy and prospects for new medicines in eosinophilic granulomatosis with polyangiitis (Churg-Strauss syndrome)," Expert Review of Clinical Immunology, vol. 12, No. 10, pp. 1059-1067 (2016).
Pagnoux, C. et al., "Treatment of granulomatosis with polyangiitis (Wegener's)," Expert Review of Clinical Immunology, 11:3, 339-348 (2015).
Falk, R. J. et al., "Anti-neutrophil cytoplasmic autoantibodies induce neutrophils to degranulate and produce oxygen radicals in vitro," Proc. Natl. Acad. Sci. USA, vol. 87, pp. 4115-4119, Jun. 1990.
Popa, E. R. et al., "Differential B- and T-cell activation in Wegener's granulomatosis," J Allergy Clin Immunol 1999;103:885-894.
Rawn, S. et al., "Purpura, petechiae, and bullae as first signs of juvenile granulomatosis with polyangiitis," Eur J Pediatr (2014) 173:1685-1689.
Selga, D. et al., "Polyarteritis nodosa when applying the Chapel Hill nomenclature—a descriptive study on ten patients," Rheumatology 2006;45:1276-1281.
Shapiro, S. C. et al., "Inflammatory bowel disease mimicking granulomatosis with polyangiitis: a case report," Journal of Medical Case Reports (2016) 10:214.
Schirmer, J. H. et al., "Clinical presentation and long-term outcome of 144 patients with microscopic polyangiitis in a monocentric German cohort," Rheumatology 2016;55:71-79.
Stone, J. H. et al., "A Disease-Specific Activity Index for Wegener's Granulomatosis," Arthritis & Rheumatism, vol. 44, No. 4, Apr. 2001, pp. 912-920.
Suka, M. et al., "Improvement in health-related quality of life in MPO-ANCA-associated vasculitis patients treated with cyclophosphamide plus prednisolone: an analysis of 18 months of follow-up data from the JMAAV study," Mod Rheumatol (2012) 22:877-884.
Trouvin, A.-P. et al., "Usefulness of monitoring of B cell depletion in rituximab-treated rheumatoid arthritis patients in order to predict clinical relapse: a prospective observational study," Clinical and Experimental Immunology, 180: 11-18 (2014).
Von Vietinghoff, S. et al., "Membrane proteinase 3 and Wegener's granulomatosis," Clinical Nephrology, vol. 64, No. 4, pp. 453-459 (2005).
Yates, M. et al., "EULAR/ERA-EDTA recommendations for the management of ANCA-associated vasculitis," Ann Rheum Dis 2016;75:1583-1594.
Bondebjerg, J. et al., "Novel semicarbazide-derived inhibitors of human dipeptidyl peptidase I (hDPPI)," Bioorg Med Chem. 2005;13:4408-4424.
Bondejberg, J. et al., "Dipeptidyl Nitriles as Human Dipeptidyl Peptidase 1 Inhibitors," Bioorg Med Chem Lett. 2006;16:3614-3617.
Chalmers, J. D. et al., "Phase 2 Trial of the DPP-1 Inhibitor Brensocatib in Bronchiectasis," N Engl J Med. Nov. 26, 2020;383(22):2127-2137. doi: 10.1056/NEJMoa2021713.
Chalmers, J. D. et al., "Neutrophil Elastase Activity Is Associated with Exacerbations and Lung Function Decline in Bronchiectasis," Am J Respir Crit Care Med. 2017; 195(10):1384-1393.
Gardiner, P. et al., "Neutrophil maturation rate determines the effects of dipeptidyl peptidase 1 inhibition on neutrophil serine protease activity," Br J Pharmacol. 2016;173:2390-401.
Guarino, C. et al., "Prolonged pharmacological inhibition of cathepsin C results in elimination of neutrophil serine proteases," Biochem Pharmacol. 2017;131:52-67.
Guay, D. et al., "Therapeutic Utility and Medicinal chemistry of Cathepsin C Inhibitors," Curr Top Med Chem. 2010;10:708-716.
Guay, D. et al., "Design and synthesis of dipeptidyl nitriles as potent, selective, and reversible inhibitors of cathepsin C," Bioorg Med Chem Lett. 2009;19:5392-5396.
Korkmaz, B. et al., "Therapeutic targeting of cathepsin C: from pathophysiology to treatment," Pharmacol Ther. 2018;190:202-236.
Korkmaz, B. et al., "Lung Protection by Cathepsin C Inhibition: A New Hope for COVID-19 and ARDS?" J Med Chem. 2020;63:13258-13265. doi:10.1021/acs.jmedchem.0c00776.

(56) References Cited

OTHER PUBLICATIONS

Korkmaz, B. et al., "Structure-based design and in vivo anti-arthritic activity evaluation of a potent dipeptidyl cyclopropyl nitrile inhibitor of cathepsin C," Biochem Pharmacol. 2019;164:349-367.

Laine, D. I. et al., "Inhibitors of Cathepsin C (DPPI)," Expert Rev. Ther Pat. 2010;20: 497-506.

Laine, D. I. et al., "Discovery of novel cyanamide-based inhibitors of cathepsin C," ACS Med Chem Lett. 2010;2(2):142-147.

McShane, P. J. et al., "Non-cystic fibrosis bronchiectasis," Am J Respir Crit Care Med. 2013;188(6):647-656. doi: 10.1164/rccm. 201303-0411CI.

Méthot, N. et al., "Inhibition of the activation of multiple serine proteases with a cathepsin C inhibitor requires sustained exposure to prevent proenzyme processing," J. Biol Chem. 2007;282:20836-20846.

Méthot, N. et al., "In Vivo Inhibition of Serine Proteases\ Processing Requires a High Fractional Inhibition of Cathepsin C," Mol. Pharm. 2008;73(6):1857-1865.

Miller, B. E. et al., "Epithelial desquamation observed in a Phase I study of an oral cathepsin C inhibitor (GSK2793660)," Br J Clin Pharmacol. 2017;83(12):2813-2820. doi: 10.1111/bcp.13398.

Palmér, R. et al., "Dipeptidyl Peptidase 1 Inhibitor AZD7986 Induces a Sustained, Exposure-Dependent Reduction in Neutrophil Elastase Activity in Healthy Subjects," Clin Pharmacol Ther. 2018; 104(6):1155-1164. doi: 10.1002/cpt.1053.

Pham, C. T., "Neutrophil serine proteases: specific regulators of inflammation," Nat. Rev. Immunol. Jul. 2006;6:541-550.

Rehm, S. R. T. et al., "Premedication with a cathepsin C inhibitor alleviates early primary graft dysfunction in mouse recipients after lung transplantation," Sci Rep. 2019;9(1):9925-9933.

Zhang, J. et al., "The Reversible Dipeptidyl Peptidase 1 Inhibitor, INS1007, Decreases Surface Proteinase 3 Expression and Neutrophil Serine Protease Activities in Human Neutrophils," Rheumatology. 2019;58(Supplement 2), p. ii24.

Zhang, J. et al., "INS1007, a Reversible Dipeptidyl Peptidase 1 Inhibitor, Ameliorates Interferon-alpha-Accelerated Lupus Nephritis in Mice," Abstract Review, 17th International Congress of Immunology. 2019. Abstract: A-1059-0027-00953, 1 page.

International Search Report and Written Opinion for International Application No. PCT/US2023/062731, dated May 30, 2023, 32 pages.

Korkmaz, B. et al., "Cathepsin C inhibition as a potential treatment strategy in cancer," Biochemical Pharmacology, 194 (Dec. 2021):114803, 15 pages.

Insmed Announces Worldwide License Agreement with AstraZeneca for Oral DPP1 Inhibitor, Oct. 2016, 3 pages.

\* cited by examiner

Tabletability plot for tablets from second lubrication trial

PHARMACEUTICAL COMPOSITIONS COMPRISING (2S)-N-{(1S)-1-CYANO-2-[4-(3-METHYL-2-OXO-2,3-DIHYDRO-1,3-BENZOXAZOL-5-YL)PHENYL]ETHYL}-1,4-OXAZEPANE-2-CARBOXAMIDE

CROSS-REFERENCE TO RELATED APPLICATIONS

This application is a U.S. National Phase of PCT/EP2019/055138, filed Mar. 1, 2019, which claims priority from U.S. Provisional Patent Application No. 62/636,944, filed Mar. 1, 2018, the disclosure of which is incorporated by reference herein in their entireties.

BACKGROUND OF THE INVENTION

The present disclosure relates to pharmaceutical compositions containing the compound (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide (or "Compound A"), or a pharmaceutically acceptable salt thereof. Compound A has the following structural formula:

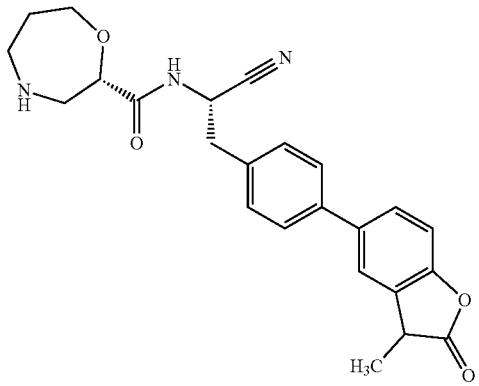 [SMILES: CC1C(=O)Oc2ccc(-c3ccc(C[C@@H](C#N)NC(=O)[C@@H]4CNCCCO4)cc3)cc21]

Compound A, and pharmaceutically acceptable salts thereof, is disclosed in U.S. Patent Publication No. 2015/0210655, which is hereby incorporated by reference in its entirety for all purposes, as an inhibitor of dipeptidyl peptidase (DPP1; EC 3.4.14.1). U.S. Patent Publication No. 2015/0210655 also describes the use of Compound A in the treatment and/or prevention of clinical conditions including respiratory diseases (such as asthma, bronchiectasis and chronic obstructive pulmonary disease (COPD)), Compound A's therapeutic use, pharmaceutical compositions containing Compound A and processes for preparing Compound A.

SUMMARY OF THE INVENTION

In one aspect, a pharmaceutical composition comprising from about 1.0 to about 30 wt % of a compound of Formula (I), or a pharmaceutically acceptable salt thereof, is provided:

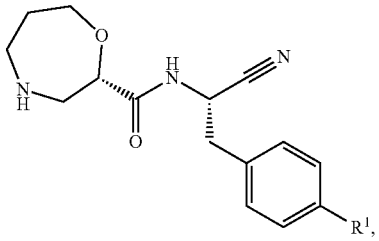

wherein, $R^1$ is

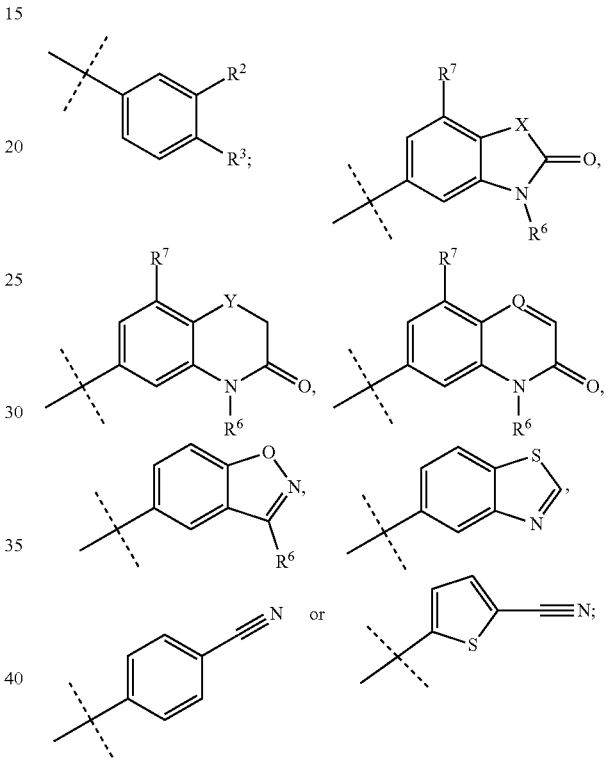

$R^2$ is hydrogen, F, Cl, Br, $OSO_2C_{1-3}$alkyl, or $C_{1-3}$alkyl;
$R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring; or
$R^6$ is $C_{1-3}$alkyl, optionally substituted by 1, 2 or 3 F and/or optionally by OH, $OC_{1-3}$alkyl, $N(C_{1-3}$alkyl$)_2$, cyclopropyl, or tetrahydropyran;
$R^7$ is hydrogen, F, Cl or $CH_3$;
X is O, S or $CF_2$;
Y is O or S;
Q is CH or N.

The composition further comprises from about 55 to about 75 wt % of a pharmaceutical diluent, from about 15% to about 25% of a compression aid, from about 3.0% to about 5.0 wt % of a pharmaceutical disintegrant, from about 0.00 to about 1.0 wt % of a pharmaceutical glidant; and from about 2 to about 6 wt % of a pharmaceutical lubricant; wherein the component weights add up to 100.

In one embodiment of the composition provided herein, the pharmaceutical composition comprises glycerol behenate as the pharmaceutical lubricant.

In one embodiment of the composition provided herein, the pharmaceutical composition comprises microcrystalline cellulose as the diluent.

In even another embodiment, the pharmaceutical composition provided herein comprises dibasic calcium phosphate dihydrate as the compression aid.

One embodiment of the composition provided herein includes a composition comprising sodium starch glycolate as the pharmaceutical disintegrant.

Yet another embodiment is directed to a pharmaceutical composition comprising silicon dioxide as the glidant.

In one embodiment, the pharmaceutical composition comprises about 1.0 to about 30 wt % of (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide (Compound A); about 55 to about 75 wt % of a pharmaceutical diluent, from about 15% to about 25% of a compression aid, from about 3.0% to about 5.0 wt % of a pharmaceutical disintegrant, from about 0.00 to about 1.0 wt % of a pharmaceutical glidant; and from about 2 to about 6 wt % of a pharmaceutical lubricant; wherein the component weights add up to 100. In a further embodiment, the diluent is microcrystalline cellulose, the compression aid is dibasic calcium phosphate dihydrate, the disintegrant is sodium starch glycolate, the glidant is silicon dioxide, and the lubricant is glycerol behenate.

Another aspect of the invention is directed to a method of treating an obstructive disease of the airway in a patient in need thereof. The method comprises administering to the patient in need of treatment, one of the compositions provided herein. In one embodiment, the composition comprises Compound A as the compound of Formula (I). In a further embodiment, the obstructive disease of the airway is bronchiectasis or cystic fibrosis. In a further embodiment, the obstructive disease of the airway is bronchiectasis.

Another aspect of the invention is directed to a method for treating an antineutrophil cytoplasmic autoantibodies (ANCA) associated vasculitis in a patient in need thereof. The method comprises administering to the patient in need of treatment, one of the compositions provided herein. In one embodiment, the composition comprises Compound A as the compound of Formula (I). In one embodiment, the ANCA associated vasculitis is granulomatosis with polyangiitis (GPA). In another embodiment, the ANCA associated vasculitis is microscopic polyangiitis (MPA). In one embodiment, the patient has an active ANCA associated vasculitis (e.g., active GPA or MPA). In another embodiment, the patient is in remission of an ANCA associated vasculitis (e.g., in remission of GPA or MPA).

DETAILED DESCRIPTION OF THE INVENTION

Figure 1:
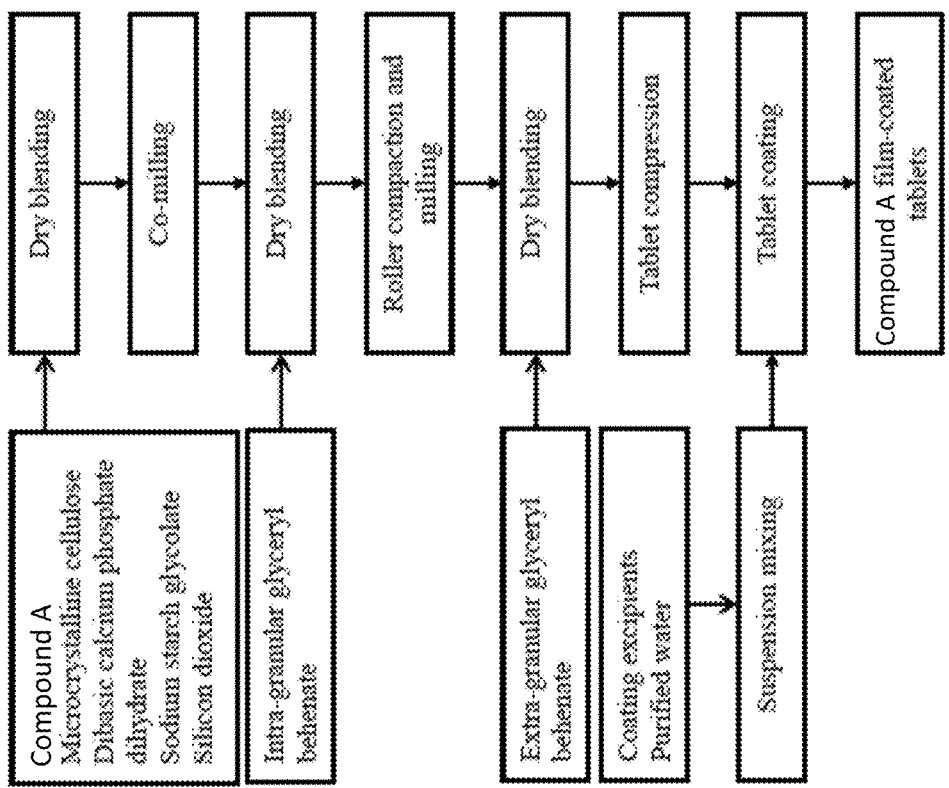
FIG. 1 is a flow diagram for an embodiment of a method for manufacturing one of the compositions of the invention.

As used herein, "$C_{1-3}$" means a carbon group having 1, 2 or 3 carbon atoms.

The term "alkyl", unless otherwise noted, includes both straight and branched chain alkyl groups and may be, substituted or non-substituted. "Alkyl" groups include, but are not limited to, methyl, ethyl, n-propyl, i-propyl, butyl, pentyl.

The term "pharmaceutically acceptable", unless otherwise noted, is used to characterize a moiety (e.g., a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

"Effective amount" or "therapeutically effective amount" means an amount of disease-modifying Compound A, or a pharmaceutically acceptable salt thereof, used in the present invention sufficient to result in the desired therapeutic response.

The skilled person will appreciate that certain pharmaceutical excipients may be used in anhydrate form or in one or more hydrated forms. For example, lactose may be used as an anhydrous form or as a monohydrate. Similarly, dibasic calcium phosphate may be used as the anhydrate form or as the dihydrate form. In the present disclosure, where the hydration level of any pharmaceutical excipients is not explicitly mentioned, it is to be interpreted that any and all conventional hydration levels are encompassed by the term. Therefore, "lactose" (without further qualification) includes lactose monohydrate, lactose in the anhydrate form and mixtures thereof.

Similarly, the skilled person will appreciate that calcium phosphate may be used in a dibasic form or a tribasic form. In present disclosure, "calcium phosphate" (without further qualification) includes the dibasic form, the tribasic form and mixtures thereof.

In the present disclosure, 'wt %' refers to 'weight percent' and has its ordinary meaning as is customary in the technical field. Accordingly, 'wt %' refers to a proportion of Component X within Composition Y, in each case calculated based on the weights of Component X and Composition Y (as opposed to other physical parameters, such as the volume or number of moles present). For example, if there is 2 g of Component X within 20 g of Composition Y then Component X makes up 10 wt % of Composition Y.

As described herein, the components of the pharmaceutical composition are described in terms of 'parts', where 'all parts are by weight'. It is to be understood that such language simply defines a relative ratio of the components, where the ratio is defined in terms of relative weights (as opposed to other physical parameters, such as the volume or number of moles present). By way of example, if there is 1 g of Component X and 4 g of Component Z in a mixture where the sum of the parts of Component X and Component Z are defined as being equal to 100, then in this example there are 20 parts of Component X and 80 parts of Component Z in the mixture.

Compositions

In one aspect, the present invention relates to a composition comprising one or more compounds of Formula (I), or a pharmaceutically acceptable salt thereof:

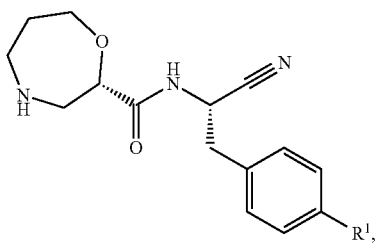

wherein,
R$^1$ is

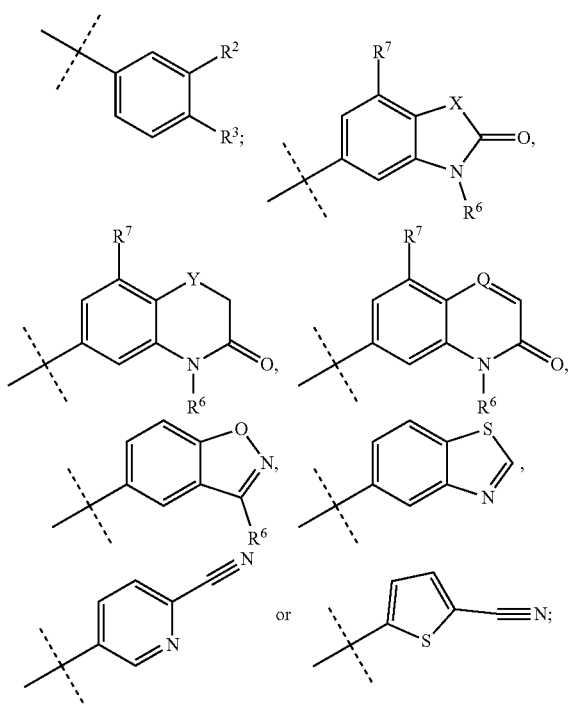

R$^2$ is hydrogen, F, Cl, Br, OSO$_2$C$_{1-3}$alkyl, or C$_{1-3}$alkyl;
R$^3$ is hydrogen, F, Cl, Br, CN, CF$_3$, SO$_2$C$_{1-3}$alkyl, CONH$_2$ or SO$_2$NR$^4$R$^5$, wherein R$^4$ and R$^5$ together with the nitrogen atom to which they are attached form an azetidine, pyrrolidine or piperidine ring; or
R$^6$ is C$_{1-3}$alkyl, optionally substituted by 1, 2 or 3 F and/or optionally by OH, OC$_{1-3}$alkyl, N(C$_{1-3}$alkyl)$_2$, cyclopropyl, or tetrahydropyran;

R$^7$ is hydrogen, F, Cl or CH$_3$;
X is O, S or CF$_2$;
Y is O or S; and
Q is CH or N.

In one embodiment R$^1$ is

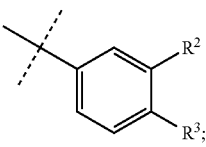

R$^2$ is hydrogen, F, Cl, Br, OSO$_2$C$_{1-3}$alkyl, or C$_{1-3}$alkyl; R$^3$ is hydrogen, F, Cl, Br, CN, CF$_3$, SO$_2$C$_{1-3}$alkyl, CONH$_2$ or SO$_2$NR$^4$R$^5$, wherein R$^4$ and R$^5$ together with the nitrogen atom to which they are attached form an azetidine, pyrrolidine or piperidine ring.

In a further embodiment, R$^1$ is

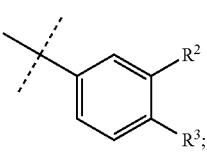

R$^2$ is hydrogen, F, Cl or C$_{1-3}$alkyl; and R$^3$ is hydrogen, F, Cl, CN or SO$_2$C$_{1-3}$alkyl.

In still a further embodiment, R$^1$ is

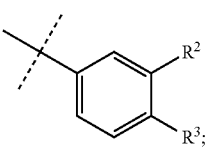

R$^2$ is hydrogen, F or C$_{1-3}$alkyl; and R$^3$ is hydrogen, F or CN.

In another embodiment, R$^1$ is

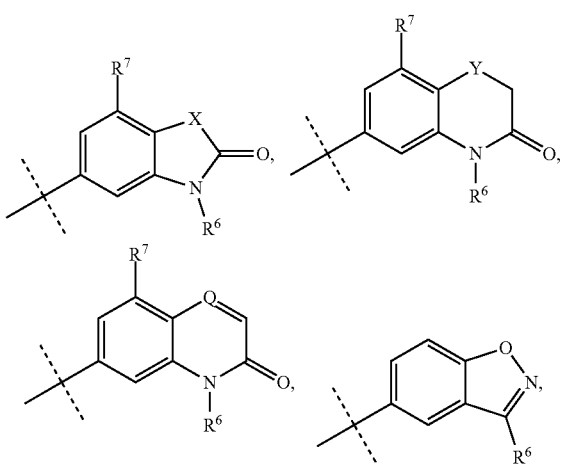

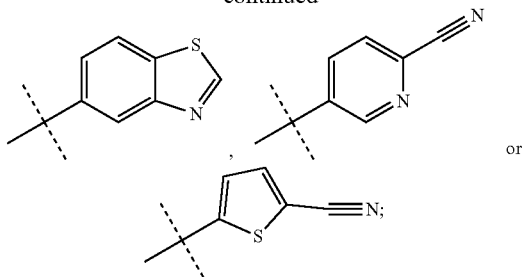

X is O, S or CF$_2$; Y is O or S; Q is CH or N; R$^6$ is C$_{1-3}$alkyl, wherein the C$_{1-3}$alkyl is optionally substituted by 1, 2 or 3 F and/or optionally substituted by OH, OC$_{1-3}$alkyl, N(C$_{1-3}$alkyl)$_2$, cyclopropyl, or tetrahydropyran; and R$^7$ is hydrogen, F, Cl or CH$_3$.

In still a further embodiment, R$^1$ is R$^1$

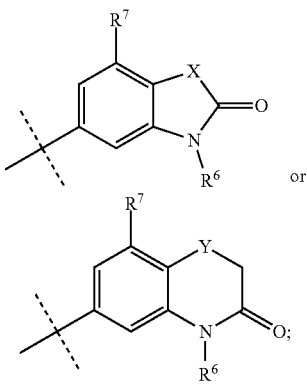

X is O, S or CF$_2$; Y is O or S; R$^6$ is C$_{1-3}$alkyl, optionally substituted by 1, 2 or 3 F and optionally substituted by OH, OC$_{1-3}$alkyl, N(C$_{1-3}$alkyl)$_2$, cyclopropyl, or tetrahydropyran; and R$^7$ is hydrogen, F, Cl or CH$_3$.

In still a further embodiment, R$^1$ is

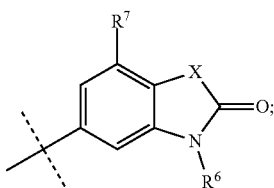

X is O, S or CF$_2$; R$^6$ is C$_{1-3}$alkyl, wherein the C$_{1-3}$alkyl is optionally substituted by 1, 2 or 3 F; and R$^7$ is hydrogen, F, Cl or CH$_3$.

In still a further embodiment, R$^1$ is

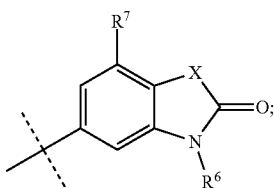

X is O; R$^6$ is C$_{1-3}$alkyl, wherein the C$_{1-3}$alkyl is optionally substituted by 1, 2 or 3 F; and R$^7$ is hydrogen.

In one embodiment, R$^2$ is hydrogen, F, Cl, Br, OSO$_2$C$_{1-3}$alkyl or C$_{1-3}$alkyl.

In a further embodiment, R$^2$ is hydrogen, F, Cl or C$_{1-3}$alkyl.

In still a further embodiment, R$^2$ is hydrogen, F or C$_{1-3}$alkyl.

In one embodiment, R$^3$ is hydrogen, F, Cl, Br, CN, CF$_3$, SO$_2$C$_{1-3}$alkyl CONH$_2$ or SO$_2$NR$^4$R$^5$, wherein R$^4$ and R$^5$ together with the nitrogen atom to which they are attached form an azetidine, pyrrolidine or piperidine ring.

In a further embodiment, R$^3$ is selected from hydrogen, F, Cl, CN or SO$_2$C$_{1-3}$alkyl.

In still a further embodiment, R$^3$ is selected from hydrogen, F or CN.

In one embodiment, R$^6$ is C$_{1-3}$alkyl, wherein said C$_{1-3}$alkyl is optionally substituted by 1, 2 or 3 F and optionally by one substituent selected from OH, OC$_{1-3}$alkyl, N(C$_{1-3}$alkyl)$_2$, cyclopropyl, or tetrahydropyran.

In a further embodiment, R$^6$ is C$_{1-3}$alkyl, wherein said C$_{1-3}$alkyl is optionally substituted by 1, 2 or 3 F. In still a further embodiment, R$^6$ is methyl or ethyl. In still a further embodiment, R$^6$ is methyl.

In one embodiment, R$^7$ is hydrogen, F, Cl or CH$_3$. In a further embodiment, R$^7$ is hydrogen.

In one embodiment, the compound of Formula (I) is (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide:

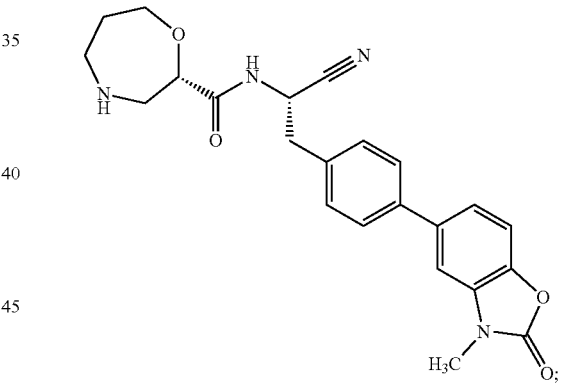

or a pharmaceutically acceptable salt thereof.

In one embodiment, the compound of Formula (I) is one or more of the following, or a pharmaceutically acceptable salt of one or more of the foregoing:

(2S)-N-[(1S)-1-Cyano-2-(4'-cyanobiphenyl-4-yl)ethyl]-1,4-oxazepane-2-carboxamide, (2S)-N-{(1S)-1-Cyano-2-[4-(3-methyl-2-oxo-2,3-dihydro-1,3-benzoxazol-5-yl)phenyl]ethyl}-1,4-oxazepane-2-carboxamide, (2S)-N-{(1S)-1-Cyano-2-[4-(3,7-dimethyl-2-oxo-2,3-dihydro-1,3-benzoxazol-5-yl)phenyl]ethyl}-1,4-oxazepane-2-carboxamide, 4'-[(2S)-2-Cyano-2-{[(2S)-1,4-oxazepan-2-ylcarbonyl]amino}ethyl]biphenyl-3-yl methanesulfonate, (2S)-N-{(1S)-1-Cyano-2-[4-(3-methyl-1,2-benzoxazol-5-yl)phenyl]ethyl}-1,4-oxazepane-2-carboxamide, (2S)-N-{(1S)-1-Cyano-2-[4'-(trifluoromethyl)biphenyl-4-yl]ethyl}-1,4-oxazepane-2-carboxamide, (2S)-N-[(1S)-1-Cyano-2-(3',4'-difluorobiphenyl-4-yl)ethyl]-1,4-oxazepane-2-carboxamide,
(2S)-N-{(1S)-1-Cyano-2-[4-(6-cyanopyridin-3-yl)phenyl]ethyl}-1,4-oxazepane-2-carboxamide,
(2S)-N-{(1S)-1-Cyano-2-[4-(4-methyl-3-oxo-3,4-dihydro-2H-1,4-benzothiazin-6-yl)phenyl]ethyl}-1,4-oxazepane-2-carboxamide,
(2S)-N-{(1S)-1-Cyano-2-[4-(3-ethyl-7-methyl-2-oxo-2,3-dihydro-1,3-benzoxazol-5-yl)phenyl]ethyl}-1,4-oxazepane-2-carboxamide,
(2S)-N-[(1S)-1-Cyano-2-{4-[3-(2-hydroxy-2-methylpropyl)-2-oxo-2,3-dihydro-1,3-benzoxazol-5-yl]phenyl}ethyl]-1,4-oxazepane-2-carboxamide,
(2S)-N-[(1S)-1-Cyano-2-{4-[3-(2,2-difluoroethyl)-7-fluoro-2-oxo-2,3-dihydro-1,3-benzoxazol-5-yl]phenyl}ethyl]-1,4-oxazepane-2-carboxamide,
(2S)-N-[(1S)-1-Cyano-2-(4-{3-[2-(dimethylamino)ethyl]-2-oxo-2,3-dihydro-1,3-benzoxazol-5-yl}phenyl)ethyl]-1,4-oxazepane-2-carboxamide,
(2S)-N-{(1S)-1-Cyano-2-[4-(3,3-difluoro-1-methyl-2-oxo-2,3-dihydro-1H-indol-6-yl)phenyl]ethyl}-1,4-oxazepane-2-carboxamide,
(2S)-N-{(1S)-1-Cyano-2-[4-(7-fluoro-3-methyl-2-oxo-2,3-dihydro-1,3-benzoxazol-5-yl)phenyl]ethyl}-1,4-oxazepane-2-carboxamide,
(2S)-N-{(1S)-1-Cyano-2-[4-(3-ethyl-2-oxo-2,3-dihydro-1,3-benzoxazol-5-yl)phenyl]ethyl}-1,4-oxazepane-2-carboxamide,
(2S)-N-[(1S)-1-Cyano-2-{4-[3-(cyclopropylmethyl)-2-oxo-2,3-dihydro-1,3-benzoxazol-5-yl]phenyl}ethyl]-1,4-oxazepane-2-carboxamide,
(2S)-N-[(1S)-1-Cyano-2-{4-[3-(2-methoxyethyl)-2-oxo-2,3-dihydro-1,3-benzothiazol-5-yl]phenyl}ethyl]-1,4-oxazepane-2-carboxamide,
(2S)-N-[(1S)-1-Cyano-2-{4-[2-oxo-3-(propan-2-yl)-2,3-dihydro-1,3-benzoxazol-5-yl]phenyl}ethyl]-1,4-oxazepane-2-carboxamide,
(2S)-N-{(1S)-1-Cyano-2-[4-(4-methyl-3-oxo-3,4-dihydro-2H-1,4-benzoxazin-6-yl)phenyl]ethyl}-1,4-oxazepane-2-carboxamide,
(2S)-N-[(1S)-1-Cyano-2-{4-[3-(2-methoxyethyl)-2-oxo-2,3-dihydro-1,3-benzoxazol-5-yl]phenyl}ethyl]-1,4-oxazepane-2-carboxamide,
(2S)-N-{(1S)-1-Cyano-2-[4-(5-cyanothiophen-2-yl)phenyl]ethyl}-1,4-oxazepane-2-carboxamide,
(2S)-N-[(1S)-2-(4'-Carbamoyl-3'-fluorobiphenyl-4-yl)-1-cyanoethyl]-1,4-oxazepane-2-carboxamide,
(2S)-N-{(1S)-1-Cyano-2-[4-(1-methyl-2-oxo-1,2-dihydroquinolin-7-yl)phenyl]ethyl}-1,4-oxazepane-2-carboxamide,
(2S)-N-[(1S)-1-Cyano-2-{4-[2-oxo-3-(tetrahydro-2H-pyran-4-ylmethyl)-2,3-dihydro-1,3-benzoxazol-5-yl]phenyl}ethyl]-1,4-oxazepane-2-carboxamide,
(2S)-N-{(1S)-2-[4-(7-Chloro-3-methyl-2-oxo-2,3-dihydro-1,3-benzoxazol-5-yl)phenyl]-1-cyanoethyl}-1,4-oxazepane-2-carboxamide,
(2S)-N-[(1S)-1-Cyano-2-{4-[3-(2,2-difluoroethyl)-2-oxo-2,3-dihydro-1,3-benzoxazol-5-yl]phenyl}ethyl]-1,4-oxazepane-2-carboxamide,
(2S)-N-[(1S)-1-Cyano-2-{4-[2-oxo-3-(2,2,2-trifluoroethyl)-2,3-dihydro-1,3-benzoxazol-5-yl]phenyl}ethyl]-1,4-oxazepane-2-carboxamide,
(2S)-N-{(1S)-1-Cyano-2-[4-(3-methyl-2-oxo-2,3-dihydro-1,3-benzothiazol-5-yl)phenyl]ethyl}-1,4-oxazepane-2-carboxamide,
(2S)-N-{(1S)-1-Cyano-2-[4'-(methylsulfonyl)biphenyl-4-yl]ethyl}-1,4-oxazepane-2-carboxamide,
(2S)-N-{(1S)-2-[4'-(Azetidin-1-ylsulfonyl)biphenyl-4-yl]-1-cyanoethyl}-1,4-oxazepane-2-carboxamide,
(2S)-N-[(1S)-1-Cyano-2-(4'-fluorobiphenyl-4-yl)ethyl]-1,4-oxazepane-2-carboxamide,
(2S)-N-{(1S)-2-[4-(1,3-Benzothiazol-5-yl)phenyl]-1-cyanoethyl}-1,4-oxazepane-2-carboxamide, or
(2S)-N-[(1S)-1-Cyano-2-(4'-cyanobiphenyl-4-yl)ethyl]-1,4-oxazepane-2-carboxamide, Methods of synthesizing compounds of Formula (I) are disclosed in PCT Publication No. 2015/110826, the disclosure of which is incorporated by reference herein in its entirety for all purposes.

In one embodiment, the compound of Formula (I) is "Compound A". Compound A, as used herein, is (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide. Compound A, also known as INS1007 or AZD7986, has the following structural formula:

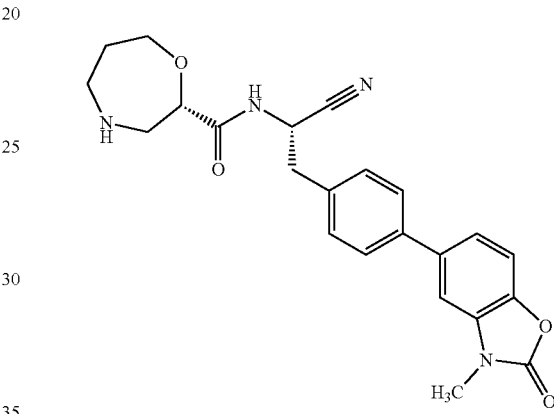

Methods of synthesizing Compound A are disclosed in U.S. Patent Publication No. 2015/0210655, the disclosure of which is incorporated by reference herein in its entirety for all purposes.

Compound A may be used in the free base form or as a pharmaceutically acceptable salt, or as any mixture thereof. In certain embodiments, Compound A is in the free base form. It is understood that "free base form" refers to the case where Compound A is not in the form of a salt.

In some embodiments of the present disclosure, Compound A is in the form of a pharmaceutically acceptable salt.

A pharmaceutically acceptable salt of Compound A may be formed using an inorganic or organic acid. A pharmaceutically acceptable salt may be formed, for example, using an inorganic acid, for example selected from hydrochloric acid, hydrobromic acid, sulfuric acid and phosphoric acid. A pharmaceutically acceptable salt may also be formed using an organic acid, for example selected from trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

In some embodiments, Compound A is polymorphic Form A of the free base form of Compound A. Polymorphic Form A of the free base form of Compound A is disclosed in U.S. Patent Publication No. 2015/0210655, the disclosure of which is incorporated herein in its entirety for all purposes.

In some embodiments, the Compound A is the free base form of Compound A and is characterized by an X-ray powder diffraction pattern having a peak at about 12.2±0.2 (° 2-theta), measured using CuKα radiation.

In some embodiments, the Compound A is the free base form of Compound A and is characterized by an X-ray powder diffraction pattern having a peak at about 20.6±0.2 (° 2-theta), measured using CuKα radiation.

In some embodiments, the Compound A is the free base form of Compound A and is characterized by an X-ray powder diffraction pattern having peaks at about 12.2±0.2° and about 20.6±0.2 ((° 2-theta), measured using CuKα radiation.

In some embodiments, the Compound A is the free base form of Compound A and is characterized by an X-ray powder diffraction pattern having peaks at about 12.2±0.2, about 14.3±0.2, about 16.2±0.2, about 19.1±0.2 and about 20.6±0.2 (° 2-theta), measured using CuKα radiation.

Unless otherwise provided herein, API weight percentages provided herein are for the respective free base form.

In some embodiments, the compositions described herein comprise a compound of Formula (I), e.g., Compound A, in an amount from about 1.0 to about 30 wt %; from about 1.0 to about 25 wt %; from about 1.0 to about 20 wt %; from about 1.0 to about 15 wt %; from about 1.0 to about 10 wt %; from about 1.0 to about 5 wt %, or from about 1.0 to about 3 wt %.

In some embodiments, the compositions described herein comprise a compound of Formula (I), e.g., Compound A, in an amount from about 1.5 to about 30 wt %; from about 1.5 to about 25 wt %; from about 1.5 to about 20 wt %; from about 1.5 to about 15 wt %; from about 1.5 to about 10 wt %; or from about 1.5 to about 5 wt %.

In some embodiments, the compositions described herein comprise a compound of Formula (I), e.g., Compound A, in an amount from about 3 to about 30 wt %; from about 3 to about 25 wt %; from about 3 to about 20 wt %; from about 3 to about 15 wt %; from about 3 to about 10 wt %; or from about 3 to about 5 wt %.

In one embodiment, the compositions described herein comprise a compound of Formula (I), e.g., Compound A, in an amount of about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt % or about 30 wt %.

In one embodiment, the compositions described herein comprise a compound of Formula (I), e.g., Compound A, in an amount of 10 mg to 50 mg, for example, 5 mg, 10 mg, 15 mg, 20 mg, 25 mg, 30 mg, 35 mg, 40 mg, 45 mg or a 50 mg. In a further embodiment, the compositions described herein comprise a compound of Formula (I) in an amount of 10 mg, 25 mg or 40 mg. In even a further embodiment, the compound is Compound A, or a pharmaceutically acceptable salt thereof.

In one aspect, the present disclosure provides a pharmaceutical composition comprising:
from about 1 to about 30 wt % of a compound of Formula (I), or a pharmaceutically acceptable salt thereof;
from about 55 to about 75 wt % of a pharmaceutical diluent;
from about 15 to about 25 wt % of a compression aid;
from about 3 to about 5 wt % of a pharmaceutical disintegrant;
from about 0.00 to about 1 wt % of a pharmaceutical glidant; and
from about 2 to about 6 wt % of a pharmaceutical lubricant;
wherein the components add up to 100 wt %.

In certain embodiments, the compound of Formula (I) is the free base form of Compound A.

The pharmaceutical composition of the present disclosure may be in any solid dosage form suitable for oral administration to a human being.

In certain embodiments, the pharmaceutical composition of the present disclosure is a pharmaceutical tablet. Pharmaceutical tablets may be prepared using methods known to those skilled in the art including, for example, dry mixing/direct compression process as described herein (see Examples section).

In some embodiments, pharmaceutical tablet comprises a tablet core wherein the tablet core comprises the pharmaceutical composition as defined herein and wherein the tablet core has a coating. In some embodiments, the coating is a film coating. Suitable film coatings are discussed herein.

The pharmaceutical compositions of the present disclosure, in one embodiment, comprise one or more pharmaceutical diluents. The term "diluent" is used interchangeably herein with "filler".

Suitable pharmaceutical diluents are known to those skilled in the art of pharmaceutical formulation science. Suitable pharmaceutical diluents, include, for example, microcrystalline cellulose, calcium carbonate, calcium phosphate, calcium sulfate, cellulose acetate, erythritol, ethylcellulose, fructose, inulin, isomalt, lactitol, lactose, magnesium carbonate, magnesium oxide, maltitol, maltodextrin, maltose, mannitol, polydextrose, polyethylene glycol, pullulan, simethicone, sodium bicarbonate, sodium carbonate, sodium chloride, sorbitol, starch, sucrose, trehalose and xylitol.

In one embodiment, the one or more pharmaceutical diluents is microcrystalline cellulose. Microcrystalline cellulose is a binder/diluent in oral tablet and capsule formulations and can be used in dry-granulation, wet-granulation, and direct-compression processes. Typical concentrations when used as a tablet diluent is 20-90%.

In some embodiments, the pharmaceutical compositions of the present disclosure comprise two or more pharmaceutical diluents.

In one embodiment, the compositions described herein comprise one or more pharmaceutical diluents in an amount from about 45 to about 85 wt %, from about 45 to about 80 wt %, from about 45 to about 75 wt %, from about 45 to about 70 wt %, from about 45 to about 65 wt %, from about 45 to about 60 wt %, or from about 45 to about 55 wt %. In a further embodiment, the one or more pharmaceutical diluents comprises microcrystalline cellulose. In even a further embodiment, the API in the formulation is Compound A, or a pharmaceutically acceptable salt thereof.

In another embodiment, the compositions described herein comprise one or more pharmaceutical diluents in an amount from about 45 to about 85 wt %, from about 50 to about 85 wt %, from about 50 to about 75 wt %, from about 55 to about 85 wt %, from about 55 to about 70 wt %, from about 60 to about 85 wt %, from about 65 to about 85 wt %, from about 70 to about 85 wt %, or from about 75 to about 85 wt %. In a further embodiment, the one or more pharmaceutical diluents comprises microcrystalline cellulose. In even a further embodiment, the API in the formulation is Compound A, or a pharmaceutically acceptable salt thereof.

In one embodiment, the compositions described herein comprise one or more pharmaceutical diluents in an amount of about 45 wt %, about 50 wt %, about 55 wt %, about 60 wt %, about 65 wt %, about 70 wt %, about 75 wt %, about 80 wt % or about 85 wt %.

In certain embodiments, the one or more pharmaceutical diluents is microcrystalline cellulose. In further such embodiments, the one or more pharmaceutical diluents comprises calcium carbonate, calcium phosphate, calcium sulfate, cellulose acetate, erythritol, ethylcellulose, fructose, inulin, isomalt, lactitol, magnesium carbonate, magnesium oxide, maltitol, maltodextrin, maltose, mannitol, polydextrose, polyethylene glycol, pullulan, simethicone, sodium bicarbonate, sodium carbonate, sodium chloride, sorbitol, starch, sucrose, trehalose and xylitol.

In this specification, the terms "disintegrant" and "disintegrants" are intended to be interpreted in the context of pharmaceutical formulation science. Accordingly, a disintegrant may be, for example: alginic acid, calcium alginate, carboxymethylcellulose calcium, chitosan, croscarmellose sodium, crospovidone, glycine, guar gum, hydroxypropyl cellulose, low-substituted hydroxypropyl cellulose, magnesium aluminum silicate, methylcellulose, povidone, sodium alginate, sodium carboxymethylcellulose, sodium starch glycolate, starch, or a combination thereof.

In one embodiment, the one or more disintegrants is sodium starch glycolate. The concentration (weight %) employed in a formulation in one embodiment, is between 2% and 8%. In a further embodiment, the concentration is about 2 wt %, about 2.5 wt %, about 3 wt %, about 3.5 wt %, about 4 wt % or about 4.5 wt %. The physical properties of sodium starch glycolate, and hence its effectiveness as a disintegrant, are affected by the degree of crosslinkage, extent of carboxymethylation, and purity.

In one embodiment, the one or more pharmaceutical disintegrants comprises croscarmellose sodium.

In certain embodiments, the compositions described herein comprise one or more pharmaceutical disintegrants in an amount from about 1 to about 15 wt %, from about 2 to about 14 wt %, from about 2 to about 13 wt %, from about 2 to about 12 wt %, from about 2 to about 11 wt %, from about 2 to about 10 wt %, from about 2 to about 9 wt %, from about 2 to about 8 wt %, from about 2 to about 7 wt %, from about 2 to about 6 wt %, from about 2 to about 5 wt %. In a further embodiment, the one or more pharmaceutical disintegrants is sodium starch glycolate. In a further embodiment, the one or more pharmaceutical diluents comprises microcrystalline cellulose. In even a further embodiment, the API in the formulation is Compound A, or a pharmaceutically acceptable salt thereof.

The terms "glidants" and "gliding agents" are intended to be interpreted in the context of pharmaceutical formulation science. Accordingly, a glidant may be, for example: silicon dioxide, colloidal silicon dioxide, powdered cellulose, hydrophobic colloidal silica, magnesium oxide, magnesium silicate, magnesium trisilicate, sodium stearate and talc.

Accordingly, in particular embodiments the one or more pharmaceutical glidants (d) comprises one or more pharmaceutical glidants selected from silicon dioxide, colloidal silicon dioxide, powdered cellulose, hydrophobic colloidal silica, magnesium oxide, magnesium silicate, magnesium trisilicate, sodium stearate and talc.

In one embodiment, the glidant is silicon dioxide. Its small particle size and large specific surface area give it desirable flow characteristics that are exploited to improve the flow properties of dry powders in a number of processes such as tableting and capsule filling. Typical silicon dioxide concentrations for use herein range from about 0.05 to about 1.0 wt %. Porous silica gel particles may also be used as a glidant, which may be an advantage for some formulations, with typical concentrations of 0.25-1%.

In one embodiment, the compositions described herein comprise one or more pharmaceutical glidants in an amount from about 0.00 to about 2 wt %; from about 0.00 to about 1.75 wt %; from about 0.00 to about 1.50 wt %; from about 0.00 to about 1.25 wt %; from about 0.00 to about 1.00 wt %; from about 0.00 to about 0.75 wt %; from about 0.00 to about 0.50 wt %; from about 0.00 to about 0.25 wt %; or from about 0.00 to about 0.20 wt %. In a further embodiment, the one or more pharmaceutical glidants comprises silicon dioxide. In a further embodiment, the one or more pharmaceutical disintegrants is sodium starch glycolate. In a further embodiment, the one or more pharmaceutical diluents comprises microcrystalline cellulose. In even a further embodiment, the API in the composition is Compound A, or a pharmaceutically acceptable salt thereof.

In one embodiment, the compositions described herein comprise one or more pharmaceutical glidants in an amount from about 0.05 to about 2 wt %; from about 0.05 to about 1.75 wt %; from about 0.05 to about 1.50 wt %; from about 0.05 to about 1.25 wt %; from about 0.05 to about 1.00 wt %; from about 0.05 to about 0.75 wt %; from about 0.05 to about 0.50 wt %; from about 0.05 to about 0.25 wt %; or from about 0.05 to about 0.20 wt %. In a further embodiment, the one or more pharmaceutical glidants comprises silicon dioxide. In a further embodiment, the one or more pharmaceutical disintegrants is sodium starch glycolate. In a further embodiment, the one or more pharmaceutical diluents comprises microcrystalline cellulose. In even a further embodiment, the API in the composition is Compound A, or a pharmaceutically acceptable salt thereof.

In one embodiment, the compositions described herein comprise one or more pharmaceutical glidants in an amount from about 0.00 to about 2 wt %; 0.05 to about 2 wt %; 0.10 to about 2 wt %; 0.2 to about 2 wt %; 0.3 to about 2 wt %; or from about 0.40 to about 2 wt %. In a further embodiment, the one or more pharmaceutical glidants comprises silicon dioxide. In a further embodiment, the one or more pharmaceutical disintegrants is sodium starch glycolate. In a further embodiment, the one or more pharmaceutical diluents comprises microcrystalline cellulose. In even a further embodiment, the API in the composition is Compound A, or a pharmaceutically acceptable salt thereof.

The terms "lubricant" and "lubricants", as used herein, are intended to be interpreted in the context of pharmaceutical formulation science. Accordingly, a lubricant may be, for example calcium stearate, glyceryl behenate, glyceryl monostearate, glyceryl palmitostearate, a mixture of behenate esters of glycerine (e.g. a mixture of glyceryl bihenehate, tribehenin and glyceryl behenate), leucine, magnesium stearate, myristic acid, palmitic acid, poloxamer, polyethylene glycol, potassium benzoate, sodium benzoate, sodium lauryl sulfate, sodium stearate, sodium stearyl fumarate, stearic acid, talc, tribehenin and zinc stearate.

Accordingly, in particular embodiments the one or more pharmaceutical lubricants (e) comprises one or more pharmaceutical lubricants selected from calcium stearate, glyceryl behenate, glyceryl monostearate, glyceryl palmitostearate, a mixture of behenate esters of glycerine (e.g., a mixture of glyceryl bihenehate, tribehenin and glyceryl behenate), leucine, magnesium stearate, myristic acid, palmitic acid, poloxamer, polyethylene glycol, potassium benzoate, sodium benzoate, sodium lauryl sulfate, sodium stearate, sodium stearyl fumarate, stearic acid, talc, tribehenin and zinc stearate.

In other particular embodiments, the one or more pharmaceutical lubricants (e) comprises one or more pharmaceutical lubricants selected from calcium stearate, glyceryl behenate, glyceryl monostearate, glyceryl palmitostearate, a mixture of behenate esters of glycerine (e.g., a mixture of glyceryl bihenehate, tribehenin and glyceryl behenate), leucine, magnesium stearate, myristic acid, palmitic acid, poloxamer, polyethylene glycol, potassium benzoate, sodium benzoate, sodium lauryl sulfate, sodium stearate, stearic acid, talc, tribehenin and zinc stearate.

Pharmaceutical compositions comprising Compound A show a specific degradant when sodium stearyl fumarate is the lubricant. The data in Table 8 (below) show that the impurity at relative retention time 1.03 (i.e., Compound A-fumarate Michael Addition adduct) is only present when sodium stearyl fumarate is the lubricant. In some embodiments, the pharmaceutical compositions comprises one or more pharmaceutical lubricants (e) and the lubricant is not sodium stearyl fumarate.

In one embodiment, the formulation provided herein includes glycerol behenate as the lubricant.

According to one embodiment of the disclosure, the one or more pharmaceutical lubricants (e) comprises glyceryl behenate, magnesium stearate, stearic acid, or a combination thereof.

In one embodiment, the lubricant is glyceryl behenate, magnesium stearate, or a combination thereof.

In one embodiment, the one or more pharmaceutical lubricants comprises sodium stearyl fumarate and/or one or more behenate esters of glycerine.

According to one embodiment, the pharmaceutical composition comprises one or more pharmaceutical lubricants in an amount from about 1 wt % to about 10 wt %, 1 wt % to about 9 wt %, 1 wt % to about 8 wt %, 1 wt % to about 7 wt %, 1 wt % to about 6 wt %, 1 wt % to about 5 wt %, from about 2 wt % to about 10 wt %, from about 2.5 wt % to about 10 wt %, from about 2 wt % to about 8 wt %, from about 2 wt % to about 7 wt %, from about 2 wt % to about 6 wt %, from about 2 wt % to about 5 wt %, from about 2 wt % to about 4.5 wt %, or from about 2.5 wt % to about 4.5 wt %. In a further embodiment, the one or more pharmaceutical lubricants in the composition is glycerol behenate. In a further embodiment, the one or more pharmaceutical glidants in the composition comprises silicon dioxide. In a further embodiment, the one or more pharmaceutical disintegrants in the composition is sodium starch glycolate. In a further embodiment, the one or more pharmaceutical diluents comprises microcrystalline cellulose. In even a further embodiment, the API in the composition is Compound A, or a pharmaceutically acceptable salt thereof.

In another embodiment the one or more pharmaceutical lubricants (e) consists of sodium stearyl fumarate and/or one or more behenate esters of glycerine or a mixture thereof.

In another embodiment the one or more pharmaceutical lubricants (e) consists of sodium stearyl fumarate, glyceryl dibehenate, glyceryl behenate, tribehenin or any mixture thereof.

In one embodiment, the one or more pharmaceutical lubricants comprises sodium stearyl fumarate. In another embodiment, the one or more pharmaceutical lubricants consists of sodium stearyl fumarate.

In one embodiment, the one or more pharmaceutical lubricants comprises one or more behenate esters of glycerine. (i.e., one or more of glyceryl dibehenate, tribehenin and glyceryl behenate).

In one embodiment, the formulation provided herein includes a compression aid. In a further embodiment, the compression aid is dicalcium phosphate dihydrate dibasic calcium phosphate dihydrate (DCPD). DCPD is used in tablet formulations both as an excipient and as a source of calcium and phosphorus in nutritional supplements.

In one embodiment, the compositions described herein comprise the compression aid, e.g., DCPD, in an amount from about 10 to about 30 wt %, including about 16 wt %, about 17 wt %, about 18 wt %, about 19 wt %, about 20 wt %, about 21 wt %, about 22 wt %, about 23 wt %, or about 24 wt %. In a further embodiment, the compression aid is present at about 20% (wt %).

In one embodiment, the compositions described herein comprise the compression aid, e.g., DCPD, in an amount from about 10 to about 25 wt %, from about 10 to about 20 wt %, from about 10 to about 15 wt %, from about 15 to about 25 wt %, or from about 20 to about 25 wt %. In a further embodiment, the one or more pharmaceutical lubricants in the composition is glycerol behenate. In a further embodiment, the one or more pharmaceutical glidants in the composition comprises silicon dioxide. In a further embodiment, the one or more pharmaceutical disintegrants in the composition is sodium starch glycolate. In a further embodiment, the one or more pharmaceutical diluents comprises microcrystalline cellulose. In even a further embodiment, the API in the composition is Compound A, or a pharmaceutically acceptable salt thereof.

In one embodiment, the composition provided herein is a tablet and has a film coating. The film coating may be applied using conventional methods known to those skilled in the art. A functional coating can be used to provide protection against, for example, moisture ingress or degradation by light, to color the formulation. Additionally, a functional coating may be used to modify or control the release of the API from the composition.

Modified- and controlled-release coatings are known to those skilled in the art and include, for example, enteric coating (e.g., cellulose acetate phthalate, hydroxypropyl methylcellulose phthalate, hydroxypropyl methylcellulose acetate succinate, polyvinyl acetate phthalate, pH-sensitive methacrylic acid/methylmethacrylate 30 copolymers, shellac, and mixtures thereof), reverse enteric coating (e.g., maltrin, aminoalkyl methacrylate copolymers available under the trade name of Eudragit® (type El 00 or EPO), polyvinylacetal diethylaminoacetate e.g., AEA® available from Sankyo Company Limited, Tokyo (Japan), and the like; and mixtures thereof) and water insoluble polymer coating (e.g., ethylcellulose, cellulose acetate, cellulose triacetate, cellulose acetate butyrate, polyvinyl acetate, neutral methacrylic acid-methylmethacrylate copolymers (e.g., Eudragit RL, RS, and NE30D, etc.), and mixtures thereof).

Suitable coatings, such as film coatings, that may be applied to the composition according to the disclosure comprise a film-forming agent, for example a sugar or more particularly a film-forming polymer. Suitable sugar coatings are well known to those skilled in the art and may comprise, for example, sucrose or lactose.

In one embodiment, the film coating comprises a mixture of hypromellose, polyethylene glycol, titanium dioxide and iron oxide red, iron oxide yellow and iron oxide black, for example, the mixture sold under the trade name Aquarius Prime Brown BAP 312542 (Ashland).

Other suitable film coatings are commercially available as concentrates that may be diluted with water and optionally a cellulose ether such as HPMC and a plasticizer such as polyethylene glycol prior to application to the composition. Such concentrates include Opaspray™ coatings from Colorcon, for example Opaspray™ Brown M-1-25092 and Opaspray Yellow M-1-22842.

Suitable film-forming agents include, for example film-forming polymers, such as cellulose ethers, esters and mixed ethers and esters, including esters of water-soluble cellulose ethers, for example hydroxypropyl methylcellulose, hydroxypropyl ethylcellulose, hydroxypropylcellulose, methylcellulose, hydroxypropyl methylcellulose acetate succinate or hydroxypropyl methylcellulose phthalate; film-forming acrylic polymers, for example methacrylate-methylmethacrylate copolymers; and film-forming vinyl polymers, for example polyvinyl alcohols or polyvinyl acetate phthalate. In some embodiments, the film-forming polymer is a water-soluble film-forming polymer, particularly a water-soluble cellulose ether for example hydroxypropyl methylcellulose (particularly hydroxypropyl methylcellulose with a dynamic viscosity of from 2 to 18 cP (measured in a 2% w/v solution at 20° C.) and selected from, for example grades 1828, 2208, 2906 and especially 2910 as defined hereinbefore). The amount of film-forming agent used will depend upon the desired properties of the film coating and the particular amount needed to achieve a desired property may be selected by those skilled in the art. Generally, the film forming agent will be present in an amount of from 40 to 90% by weight of the film coating, for example from 50 to 80% of the film coating. In certain embodiments, the film-forming agent is typically present at from about 0.5 to 5% by weight of the formulation. In other embodiments, said film-forming agent is present at from about 2.5 to 5% by weight of the formulation.

Optionally the film coating contains additional components such as plasticizer, colorants, dispersion aids and opacifiers. Plasticizers may be used to improve film flexibility and durability and adhesion properties of the film coating. Suitable plasticizers include, for example glycerin, acetylated monoglycerides, citrate esters (for example triethyl citrate), propylene glycols, polyethylene glycols (for example polyethylene glycols with a molecular weight of from 200 to 500, particularly 300), triacetin (glycerol triacetate), triglycerides (for example castor oil), or phthalate esters (for example diethylphthalate). Generally, the plasticizer, when used, is present in an amount of from 1 to 20%, for example 5 to 15% by weight of the film coating.

Suitable opacifiers and colorants are well known and include for example titanium dioxide, ferric oxides (for example iron oxide).

Suitable dispersion aids include, for example talc.

In some embodiments, the film coating comprises
(i) from 50 to 100 (e.g., from 50 to 80 parts of a water-soluble cellulose ether (e.g., hydroxypropyl methylcellulose, particularly hydroxypropyl methylcellulose with a dynamic viscosity of from 2 to 18 cP (measured in a 2% w/v solution at 20° C.), for example grades 2910, 1828, 2208 or 2906 as defined hereinbefore with a dynamic viscosity of from 5 to 7cP);
(ii) from 0 to 25 (particularly from 5 to 20 parts) parts plasticiser (e.g., polyethylene glycol, e.g., polyethylene glycol with a molecular weight of from 200 to 500); and
(iii) from 0 to 50 (particularly from 0 to 30) parts in total of opacifiers (e.g., titanium dioxide), colorants (e.g., iron oxide) and dispersion aids;
wherein all parts are by weight and the sum of the parts (i)+(ii)+(iii)=100.

The coating may comprise, for example, 0.5 to 10 wt % of the composition, e.g., from about 1 to 6%, or from about 2 to 5 wt %.

One or more of the compositions provided herein is used, in one embodiment, to treat an obstructive disease of the airway in a patient in need thereof. The obstructive disease of the airway, in one embodiment, is asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; alpha-1 antitrypsin deficiency; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus, acute lung injury, adult respiratory distress syndrome (ARDS), as well as exacerbations of each of the foregoing respiratory tract disease states. In one embodiment, the composition includes an effective amount of Compound A.

In one embodiment, the treatment is treatment of asthma (such as bronchial, allergic, intrinsic, extrinsic or dust asthma, particularly chronic or inveterate asthma (for example late asthma or airways hyper-responsiveness)), chronic obstructive pulmonary disease (COPD) or allergic rhinitis.

The compositions provided herein can be orally administered, in one embodiment, to a bronchiectasis patient in need of treatment. The bronchiectasis may be in a patient with cystic fibrosis, or a patient that does not have cystic fibrosis (sometimes referred to as "bronchiectasis unrelated to cystic fibrosis" or "non-CF bronchiectasis"). Administration schedules can be determined by the user of the method, e.g., a prescribing physician. In one embodiment, administration is once daily. In another embodiment, administration is twice daily. In another embodiment, administration is every other day, 3× per week or 4× per week.

Non-CF bronchiectasis has been reported to be caused by or associated with numerous aetiologies ranging from genetic illness to retained airway foreign body, and has been reported to be present in patients with systemic disease, common respiratory diseases such as chronic obstructive pulmonary disease (COPD) as well as uncommon diseases such as sarcoidosis (Chang and Bilton (2008). Thorax 63, pp. 269-276, incorporated by reference herein in its entirety for all purposes).

Bronchiectasis is considered a pathological endpoint that results from many disease processes and is a persistent or progressive condition characterized by dilated thick-walled bronchi. The symptoms vary from intermittent episodes of expectoration and infection localized to the region of the lung that is affected to persistent daily expectoration often of large volumes of purulent sputum. Bronchiectasis may be associated with other non-specific respiratory symptoms. The underlying pathological process of bronchiectasis, without wishing to be bound by theory, has been reported as damage to the airways which results from an event or series of events where inflammation is central to the process (Guideline for non-CF Bronchiectasis, Thorax, July 2010, V. 65(Suppl 1), incorporated by reference herein in its entirety for all purposes). Methods of treating bronchiectasis using a compound of Formula (I) are described in U.S. Publication No. 2018/0028541, which is incorporated by reference herein in its entirety for all purposes.

The term "treating" in one embodiment, includes: (1) preventing or delaying the appearance of clinical symptoms of the state, disorder or condition developing in the patient that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); (3) relieving the condition (i.e., causing regression of the state, disorder or condition or at least one of its clinical or subclinical symptoms). In one embodiment, the clinical symptom is a pulmonary exacerbation and/or (4) prophylaxis of the bronchiectasis, e.g., non-CF bronchiectasis.

Prophylaxis is expected to be particularly relevant to the treatment of persons who have suffered a previous episode of, or are otherwise considered to be at increased risk of, bronchiectasis. As such, in one embodiment of the invention, a method for providing prophylaxis of bronchiectasis in a patient in need thereof is provided. The patient in need thereof, in one embodiment, has suffered a previous episode of, or is at increased risk for being diagnosed with bronchiectasis. The method comprises administering one of the compositions provided herein to the patient. In a further embodiment, the compound of Formula (I) is (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide, or a pharmaceutically acceptable salt thereof.

A "pulmonary exacerbation" as used herein, is three or more of the following symptoms exhibited for at least 48 hours by a patient: (1) increased cough; (2) increased sputum volume or change in sputum consistency; (3) increased sputum purulence; (4) increased breathlessness and/or decreased exercise tolerance; (5) fatigue and/or malaise; (6) hemoptysis.

In one embodiment, the three or more symptoms result in a physician's decision to prescribe an antibiotic(s) to the patient exhibiting the symptoms.

In one embodiment, the treating via administering a composition provided herein comprises increasing the length of time to pulmonary exacerbation, as compared to the length of time to pulmonary exacerbation in an untreated bronchiectasis patient. For example, in some embodiments, the length of time to pulmonary exacerbation is increased at least about 20 days, as compared to the length of time to pulmonary exacerbation in an untreated bronchiectasis patient. In other embodiments, the length of time to pulmonary exacerbation is increased from about 20 to about 100 days, as compared to the length of time to pulmonary exacerbation in an untreated bronchiectasis patient. In another embodiment, the length of time to pulmonary exacerbation is increased from about 25 to about 100 days, from about 30 to about 100 days, from about 35 to about 100 days or from about 40 to about 100 days, as compared to the length of time to pulmonary exacerbation in an untreated bronchiectasis patient. In other embodiments, the increase is from about 25 to about 75 days, from about 30 to about 75 days, from about 35 to about 75 days or from about 40 to about 75 days, as compared to the length of time to pulmonary exacerbation in an untreated bronchiectasis patient. In other embodiments, the increase in time to pulmonary exacerbation is about 30 to about 60 days, as compared to the length of time to pulmonary exacerbation in an untreated bronchiectasis patient. In a further embodiment, the compound in the composition is an effective amount of Compound A, or a pharmaceutically acceptable salt thereof.

In one embodiment, the increasing of the time between pulmonary exacerbation comprises increasing by about 1 day, about 3 days, about 1 week, about 2 weeks, about 3 weeks, about 4 weeks, about 5 weeks or about 6 weeks, or increasing by at least about 1 day, at least about 3 days, at least about 1 week, at least about 2 weeks, at least about 3 weeks, at least about 4 weeks, at least about 5 weeks or at least about 6 weeks. In another embodiment, the increasing comprising increasing of from about 20 days to about 100 days, or from about 30 days to about 100 days, or from about 20 days to about 75 days, or from about 20 days to about 50 days, or from about 20 days to about 40 days. In a further embodiment, the compound in the composition is an effective amount of Compound A, or a pharmaceutically acceptable salt thereof.

In yet another embodiment, a method for treating bronchiectasis, e.g., non-CF bronchiectasis, is provided comprising administering one of the compositions provided herein to a patient in need thereof. In one embodiment, the compound is administered once daily. Treating comprises reducing the rate of pulmonary exacerbation, as compared to the rate of pulmonary exacerbation experienced by the patient prior to treatment, or as compared to an untreated bronchiectasis patient. The rate of pulmonary exacerbations can be calculated by dividing the number of exacerbations by a specific time period, e.g., 1 day, 1 week, about 1 month, about 2 months, about 3 months, about 4 months, about 5 months, about 6 months, about 9 months, about 12 months, about 15 months, about 18 months, about 21 months or about 24 months. The reduction in rate of exacerbations, in one embodiment, is a reduction by about 15%, by about 20%, by about 25%, by about 30%, by about 35%, by about 40% or by about 50%, by about 55%, by about 60%, by about 65%, by about 70%, by at least about 5%, by at least about 10%, by at least about 15%, by at least about 20%, at least about 25%, at least about 30%, at least about 35%, at least about 40%, or at least about 50%, at least about 70% as compared to the rate of pulmonary exacerbation experienced by the patient prior to treatment, or compared to an untreated bronchiectasis patient.

In another embodiment, the reduction in rate of exacerbations, in one embodiment, is a reduction by at least about 5%, by at least about 10%, by at least about 15%, by at least about 20%, at least about 25%, at least about 30%, at least about 35%, at least about 40%, or at least about 50%. In one embodiment, the compound in the composition is an effective amount of Compound A, or a pharmaceutically acceptable salt thereof.

In even another embodiment, a method for treating bronchiectasis, e.g., non-CF bronchiectasis is provided comprising administering to a patient in need thereof, one of the compositions provided herein. In one embodiment, the compound is administered once daily. The method comprises decreasing the duration of pulmonary exacerbation, as compared to the duration of a pulmonary exacerbation experienced by the patient prior to treatment, or as compared to an untreated bronchiectasis patient. The reduced duration of a pulmonary exacerbation is a reduced duration of about 12 hours, about 24 hours, about 48 hours or about 72 hours, at least about 6 hours, at least about 12 hours, at least about 24 hours, at least about 48 hours, at least about 72 hours, at least about 96 hours, at least about 120 hours, at least about 144 hours or at least about 168 hours. In another embodiment, the reduced duration of a pulmonary exacerbation is a reduced duration of about 6 hrs to about 96 hrs, about 12 hrs to about 96 hrs, about 24 hrs to about 96 hrs, about 48 hrs to about 96 hrs or about 48 hrs to about 168 hrs. In yet another embodiment, the reduced duration of a pulmonary exacerbation is a reduced duration of about 1 day to about 1 week, about 2 days to about 1 week, about 3 days to about 1 week, about 4 days to about 1 week, about 5 days to about 1 week or about 6 days to about 1 week. In yet another embodiment, the reduced duration of a pulmonary exacerbation is a reduced duration of about 1 day to about 2 weeks, about 2 days to about 2 weeks, about 4 days to about 2 weeks, about 6 days to about 2 weeks, about 8 days to about 2 weeks or about 10 days to about 2 weeks.

The reduced duration, in another embodiment, is a reduction by about 6 hrs to about 96 hrs, about 12 hrs to about 96 hrs, about 24 hrs to about 96 hrs, about 48 hrs to about 96 hrs or about 48 hrs to about 168 hrs.

The reduced duration in one embodiment is the average reduction of exacerbations experienced during treatment. In a further embodiment, the composition comprises an effective amount of Compound A, or a pharmaceutically acceptable salt thereof.

In another embodiment, a method for treating bronchiectasis, e.g., non-CF bronchiectasis, is provided comprising administering one of the compositions provided herein to a patient in need thereof. In one embodiment, the compound is administered orally, once daily. In this embodiment, treating comprises reducing the number of pulmonary exacerbation-related hospitalizations of the patient as compared to the number of pulmonary exacerbation-related hospitalizations of the patient prior to treatment, or as compared to an untreated bronchiectasis patient. The number of hospitalizations in one embodiment, is measured over the treatment period and compared to the same length of time prior to treatment or in an untreated bronchiectasis patient. In a further embodiment, the compound in the composition is an effective amount of Compound A, or a pharmaceutically acceptable salt thereof.

In one embodiment of the methods provided herein, a method for treating bronchiectasis, e.g., non-CF bronchiectasis is provided comprising administering one of the compositions provided herein to a patient in need thereof, wherein the method comprises increasing the lung function in the patient, as compared to the lung function in the patient prior to treatment, or as compared to an untreated bronchiectasis patient. In one embodiment, the compound in the composition is an effective amount of Compound A, or a pharmaceutically acceptable salt thereof.

The increase in lung function in one embodiment, is measured by spirometry.

Increasing lung function, in one embodiment, comprises increasing the post-bronchodilator forced expiratory volume in 1 second ($FEV_1$), increasing the forced vital capacity (FVC), increasing the peak expiratory flow rate (PEFR), or increasing the forced expiratory flow of the FVC between 25% and 75% (FEF25-75), as compared to the respective value prior to treatment, or as compared to an untreated bronchiectasis patient. Increasing, in one embodiment, is by about 5%, about 10%, about 15%, by about 20%, by about 25%, by about 30%, by about 35%, by about 40%, by about 45% or by about 50% of the respective value. Increasing, in one embodiment, is by at least about 5%, at least about 10%, at least about 15%, by at least about 20%, by at least about 25%, by at least about 30%, by at least about 35%, by at least about 40%, by at least about 45% or by at least about 50%. In yet another embodiment, the increase is by about 5% to about 50%, by about 5% to about 40%, by about 5% to about 30% or by about 5% to about 20%. In even another embodiment, increasing is by about 10% to about 50%, by about 15% to about 50%, by about 20% to about 50% or by about 25% to about 50%.

The assessment of lung function, e.g., via $FEV_1$, PEFR or $FEF_{25-75}$ measurement, in one embodiment, comprises comparing the lung function in the patient prior to treatment, e.g., immediately prior to treatment, to a time point during treatment, to an average of measurements taken during treatment, or after treatment has completed.

As provided herein, treatment via a method of the invention, in one embodiment, comprises improving the lung function in the patient, wherein the lung function is measured by spirometry. Spirometry is a physiological test that measures how an individual inhales or exhales volumes of air. The primary signal measured in spirometry may be volume or flow. For the methods described herein, pulmonary function test (PFT) by spirometry (e.g., $FEV_1$, FVC, PEFR, and $FEF_{25-75}$) is performed per the American Thoracic Society (ATS)/European Respiratory Society (ERS) criteria, e.g., as set forth by Miller et al. (Miller et al. (2005). Standardization of Spirometry. Eur. Respir. J. 26, pp. 319-38, incorporated by reference herein in its entirety for all purposes).

In one embodiment, the spirometer is capable of accumulating volume for greater than or equal to 15 seconds, e.g., ≥20 seconds, ≥25 seconds, ≥30 seconds, ≥35 seconds. The spirometer in one embodiment can measure volumes of ≥8 L (BTPS) with an accuracy of at least ±3% of reading or ±0.050 L, whichever is greater, with flows between 0 and 14 $L \cdot s^{-1}$. In one embodiment, the total resistance to airflow of the spirometer at 14 $L \cdot s^{-1}$ is <1.5 $cmH2O \cdot L^{-1} \cdot s^{-1}$ (0.15 $kPa \cdot L^{-1} \cdot s^{-1}$). In one embodiment, the total resistance of the spirometer is measured with any tubing, valves, pre-filter, etc. included that may be inserted between the patient and the spirometer. With respect to devices that exhibit changes in resistance due to water vapor condensation, in one embodiment, spirometer accuracy requirements are met under BTPS (body temperature, ambient pressure, saturated with water vapor) conditions for up to eight successive FVC maneuvers performed in a 10-min period without inspiration from the instrument.

With respect to the forced expiratory maneuvers described herein, in one embodiment, the range and accuracy recommendations as set forth in Table 6 of Miller et al. are met (Miller et al. (2005). Standardization of Spirometry. Eur. Respir. J. 26, pp. 319-38, incorporated by reference herein in its entirety for all purposes).

In one embodiment, the improvement in lung function is an improvement in the forced vital capacity (FVC), i.e., the maximal volume of air exhaled with maximally forced effort from a maximal inspiration. This measurement is expressed in liters at body temperature and ambient pressure saturated with water vapor (BTPS).

"Forced vital capacity" (FVC) denotes the volume of gas which is exhaled during a forced expiration starting from a position of full inspiration and ending at complete expiration and is one measure of treatment efficacy. In one embodiment of a method provided herein, improving the patient's lung function comprises improving the patient's FVC, compared to the patient's FVC prior to treatment, or compared to an untreated bronchiectasis patient. In one embodiment, the FVC of a treated patient is greater by about 1%, greater by about 2%, greater by about 3%, greater by about 4%, greater by about 5%, greater by about 6%, greater by about 7%, greater by about 8%, greater by about 9%, greater by about 10%, greater by about 11%, greater by about 12%, greater by about 13%, greater by about 14%, greater by about 15%, greater by about 16%, greater by about 17%, greater by about 18%, greater by about 19%, greater by about 20%, greater by about 25%, greater by about 30%, greater by about 35%, greater by about 40%, greater by about 45%, greater by about 50%, greater by about 55%, greater by about 60%, greater by about 65%, greater by about 70%, greater by about 75%, greater by about 80%, greater by about 85% or greater by about 90%, as compared to a FVC of the patient prior to treatment, or as compared to an untreated bronchiectasis patient.

FVC maneuvers can be performed according to the procedures known to those of ordinary skill in the art. Briefly, the three distinct phases to the FVC maneuver are (1) maximal inspiration; (2) a "blast" of exhalation and (3) continued complete exhalation to the end of test (EOT). The maneuver can be carried out via the closed circuit method or open circuit method. In either instance, the subject inhales rapidly and completely with a pause of less than 1 second at total lung capacity (TLC). The subject then exhales maximally until no more air can be expelled while maintaining an upright posture. The exhalation begins with a "blast" of air from the lungs and then is encouraged to fully exhale. Enthusiastic coaching of the subject continues for a minimum of three maneuvers.

The improvement in lung function, in one embodiment, is an improvement compared to lung function immediately prior to treatment, or compared to an untreated bronchiectasis patient. In a further embodiment, improving lung function comprises increasing the forced expiratory volume in one second ($FEV_1$) of the patient compared to the patient's $FEV_1$ prior to treatment, or compared to an untreated bronchiectasis patient's $FEV_1$. FEV is the volume of gas exhaled in a specified time (typically 1 second, i.e., $FEV_1$) from the start of the forced vital capacity maneuver (Quanjer et al. (1993). Eur. Respir. J. 6, Suppl. 16, pp. 5-40, incorporated by reference herein in its entirety for all purposes).

The increase in $FEV_1$, in one embodiment, is an increase of at least about 5%, for example, from about 5% to about 50%, or about 10% to about 50%, or about 15% to about 50%. In another embodiment, the $FEV_1$ of the treated patient is greater by about 1%, greater by about 2%, greater by about 3%, greater by about 4%, greater by about 5%, greater by about 6%, greater by about 7%, greater by about 8%, greater by about 9%, greater by about 10%, greater by about 11%, greater by about 12%, greater by about 13%, greater by about 14%, greater by about 15%, greater by about 16%, greater by about 17%, greater by about 18%, greater by about 19%, greater by about 20%, greater by about 25%, greater by about 30%, greater by about 35%, greater by about 40%, greater by about 45%, greater by about 50%, greater by about 55%, greater by about 60%, greater by about 65%, greater by about 70%, greater by about 75%, greater by about 80%, greater by about 85%, or greater by about 90%, compared to a $FEV_1$ of the patient prior to treatment, or compared to an untreated bronchiectasis patient.

In another embodiment, the improving lung function comprises increasing the patient's $FEV_1$ by about 25 mL to about 500 mL, or about 25 mL to about 250 mL, or about 50 mL to about 200 mL, as compared to a $FEV_1$ of the patient prior to treatment, or as compared to an untreated bronchiectasis patient.

In one embodiment, improving lung function comprises improving the mean forced expiratory flow between 25% and 75% of the FVC ($FEF_{25-75}$) (also referred to as the maximum mid-expiratory flow) of the patient, as compared to a $FEF_{25-75}$ of the patient prior to treatment, or as compared to an untreated bronchiectasis patient. The measurement is dependent on the validity of the FVC measurement and the level of expiratory effort. The $FEF_{25-75}$ index is taken from the blow with the largest sum of $FEV_1$ and FVC.

In one embodiment, improving lung function comprises improving the peak expiratory flow rate (PEFR) of the patient. The improvement is an improvement compared to PEFR immediately prior to treatment, or as compared to an untreated bronchiectasis patient. The PEFR measures the fastest rate of air that can be expired by a subject. In one embodiment, the PEFR of a treated patient is greater by about 1%, greater by about 2%, greater by about 3%, greater by about 4%, greater by about 5%, greater by about 6%, greater by about 7%, greater by about 8%, greater by about 9%, greater by about 10%, greater by about 11%, greater by about 12%, greater by about 13%, greater by about 14%, greater by about 15%, greater by about 16%, greater by about 17%, greater by about 18%, greater by about 19%, greater by about 20%, greater by about 25%, greater by about 30%, greater by about 35%, greater by about 40%, greater by about 45%, greater by about 50%, greater by about 55%, greater by about 60%, greater by about 65%, greater by about 70%, greater by about 75%, greater by about 80%, greater by about 85% or greater by about 90%, as compared to a PEFR of the patient prior to treatment, or as compared to an untreated bronchiectasis patient.

In yet another embodiment of the invention, a method for treating bronchiectasis is provided comprising administering one of the compositions provided herein to a patient in need thereof, wherein treating comprising increasing the quality of life (QOL) of the patient, as compared to the quality of life of the patient prior to treatment, e.g., a baseline value. In a further embodiment, the compound in the composition is an effective amount of Compound A, or a pharmaceutically acceptable salt thereof.

In one embodiment, the QOL of the patient is assessed via the Quality of Life-Bronchiectasis (QOL-B) questionnaire. The QOL-B questionnaire is a validated, self-administered Patient Reported Outcome (PRO) that assesses symptoms, functioning and health-related QOL for subjects with bronchiectasis (Quittner et al. (2014). Chest 146(2), pp. 437-448; Quittner et al. (2015) Thorax 70(1), pp. 12-20, each of which is incorporated by reference in its entirety for all purposes). The QOL-B contains 37 items on 8 domains (Respiratory Symptoms, Physical Functioning, Role Functioning, Emotional Functioning, Social Functioning, Vitality, Health Perceptions and Treatment Burden).

In another embodiment, the QOL of the patient is assessed via the Leicester Cough Questionnaire (LCQ). An improvement in QOL in one embodiment, is a change from baseline (prior to treatment) in LCQ score for the patient. The LCQ is a validated questionnaire evaluating cough on QOL in subjects with bronchiectasis and other conditions where cough is a common symptom (Murray et al. (2009). Eur Respir J. 34: 125-131, incorporated by reference herein in its entirety for all purposes). The LCQ comprises 19 items and takes 5 to 10 minutes to complete. Each item assesses symptoms or the impact of symptoms over the last 2 weeks on a seven-point Likert scale. Scores in three domains (physical, psychological and social) are calculated as a mean for each domain (range 1 to 7). A total score (range 3 to 21) is also calculated by adding the domain scores together. Higher scores indicate better QOL.

In another embodiment, the QOL of the patient is assessed via the St. George's Respiratory Questionnaire (SGRQ). An improvement in QOL in one embodiment, is a change from baseline (prior to treatment) in SGRQ score for the patient. The St. George's Respiratory Questionnaire (SGRQ) is self-administered with 50 questions designed to measure and quantify health-related health status in subjects with chronic airflow limitation (Jones et al. (1991). Respir Med. 85 Suppl B 25-31; discussion 33-7, incorporated by reference herein in its entirety for all purposes). The SGRQ assesses health related quality of life by evaluating 3 health domains: (1) symptoms (distress caused by respiratory symptoms), (2) activity (effects of disturbances to mobility and physical activity), and (3) impact (the effect of disease on factors such as employment, personal control of one's health, and need for medication). It has been shown to correlate well with the established measures of the 3 domains in subjects with asthma and COPD. It has also been validated for use in NCFBE. A composite total score is derived as the sum of domain scores for symptoms, activity, and impact with 0 the best possible score and 100 the worst possible score. A reduction in score of 4 units is generally recognized as a clinically meaningful improvement in QOL.

In another embodiment of the method for treating bronchiectasis provided herein, one of the compositions provided herein, is administered to a patient in need thereof, wherein the method comprises decreasing active neutrophil elastase (NE) sputum concentration, as compared to the patient's NE sputum concentration, prior to treatment. In one embodiment, the composition comprising a compound of Formula (I) is administered via oral administration. In a further embodiment, administration is 1× daily, every other day, 2× weekly, 3× weekly or 4× weekly. In a further embodiment, the compound in the composition is an effective amount of Compound A, or a pharmaceutically acceptable salt thereof. Decreasing active NE sputum concentration, in one embodiment, comprises decreasing by about 10%, about 20%, about 25%, about 30%, about 40%, about 50%, about 60%, about 70%, or about 80%. In another embodiment, decreasing active NE sputum concentration comprises decreasing by at least about 1%, at least about 5%, at least about 10%, at least about 20%, at least about 30%, at least about 40%, at least about 50%, at least about 60%, at least about 70% or at least about 80%.

In even another embodiment of the method for treating bronchiectasis provided herein, one of the compositions provided herein is administered to a patient in need thereof, and the method comprises lightening the sputum color of the patient, as measured by the sputum color chart of Murray 2009 (Murray et al. (2009). Eur Respir J. 2009; 34:361-364, incorporated by reference herein in its entirety for all purposes), as compared to the patient's sputum color, prior to treatment. In one embodiment, the composition comprising a compound of Formula (I) is administered via oral administration. In a further embodiment, administration is 1× daily, every other day, 2× weekly, 3× weekly or 4× weekly. The compound in the composition, in one embodiment, is an effective amount of Compound A, or a pharmaceutically acceptable salt thereof.

The lightening of color, in one embodiment, is a lightening by a single gradation. For example, in one embodiment, the lightening is from purulent (dark yellow and/or dark green) to mucopurulent (pale yellow and/or pale green). In another embodiment, the lightening is from mucopurulent (pale yellow and/or pale green) to mucoid (clear).

The change in color, in another embodiment, is a lightening of two gradations, i.e., the lightening is from purulent (dark yellow and/or dark green) to mucoid (clear).

Sputum induction is carried out if the patient cannot produce sputum on his or her own. Sputum induction, in one embodiment, is initiated via patient nebulization of a saline solution. The percentage of saline, e.g., 3% or 7% or 10% or 13%, is decided based on the user of the method's preference. The selected saline is placed in the nebulizer, and the subject is in a sitting up or in a semi-fowler position. The subject in one embodiment, wears a nose clip during the nebulization. The subject breathes slowly and deeply through the nebulizer mouthpiece inhaling the salt water mist. The subject is reminded to not breathe quickly but to have slow, deep breaths pausing at peak inspiration to allow deposition of particles. The nebulization time in one embodiment, is 10 minutes.

At the end of nebulization, the subject is instructed to take a few deep breaths, swallow the extra saliva in his/her mouth and attempt to cough up a sputum sample. The subject is encouraged to cough forcefully using the deep coughing method and/or "huffing" cough method. All sputum is deposited in the specimen container. The procedure can be repeated if the amount of sputum collected, e.g., less than 1 mL, less than 2 mL, or less than 3 mL, is not sufficient.

The compositions provided herein can be orally administered, in one embodiment, to a patient in need of treatment of an ANCA associated vasculitis (e.g., GPA or MPA). Methods of treating ANCA associated vasculitis (e.g., GPA or MPA) using a compound of Formula (I) are described in U.S. application Ser. No. 16/269,191, which is incorporated by reference herein in its entirety for all purposes.

GPA is a rare systemic autoimmune necrotizing granulomatous inflammation and systemic vasculitis of small blood vessels (Pagnoux (2016). Eur J Rheumatol. 3(3), pp. 122-33; Schönermarck et al. (2015). Nephrol Dial Transplant. 2015; 30(Suppl1): i46-52, each incorporated by reference here in its entirety for all purposes). It most commonly affects the upper and/or lower respiratory tracts, kidneys, skin, and peripheral nerves. The pathogenesis of GPA involves neutrophils and ANCAs. In most patients with GPA, ANCAs bind to membrane-bound PR3 (mPR3), triggering neutrophil activation with the release of ROS and proteases, including active NSPs (PR3, NE, and Cat G). This extracellular proteolytic activity contributes to the vascular necrosis of endothelial cells observed in GPA patients (Jerke et al. (2015). Kidney Int. 88(4):764-775; Kettritz (2016). Immunol Rev. 273(1): 232-248, each incorporated by reference here in its entirety for all purposes).

Left untreated, GPA is a severe and progressive disease that leads to death from multisystem organ failure (Millet et al. (2013). Ann Rheum Dis. 72(8):1273-9; Yates and Watts (2017). Clin Med (Lond). 17(1):60-64, each incorporated by reference here in its entirety for all purposes). The standard therapy includes cytotoxic immunosuppressive agents such as cyclophosphamide, and most recently rituximab, combined with high-dose glucocorticoids. Despite treatment, disease relapses are common (Guillevin et al. (2014). N Engl J Med. 371(19): 1771-80; Jayne et al. (2003). N Engl J Med. 2003; 349(1):36-44; Pagnoux et al. (2008). N Engl J Med. 359(26):2790-2803, each incorporated by reference herein in their entireties for all purposes) and the mortality rates remain high (Heijl et al. (2017). RMD open; Volume 3, Issue 1, p:e000435; Pearce et al. (2017). Rheumatology (Oxford). 56(4):589-96, each incorporated by reference herein in their entireties for all purposes). Furthermore, there is a narrow safety margin of current therapies due to systemic toxicities. Taken together, there remains a high unmet need for adequate treatment of GPA, particularly for the maintenance of remission. This residual unmet need underscores the necessity to develop novel therapeutic strategies, such as may be achieved by the methods of the present invention.

In some embodiments, the methods provided herein employ reversible inhibitors of the lysosomal cysteine protease dipeptidyl peptidase 1 (DPP1) of Formula (I) in methods for treating an ANCA associated vasculitis, such as, but not limited to, GPA and/or MPA. Without wishing to be bound by theory, it is thought that the compounds of Formula (I), administered via the methods provided herein have beneficial effects via inhibition of PR3 activation via the upstream inhibition of DPP1. Inhibition of DPP1, without wishing to be bound by theory, reduces the amount of activated NSPs available for release during neutrophil degranulation. Moreover, inhibition of PR3 activation in turn leads to lack of PR3 interaction and expression at the neutrophil membrane surface (mPR3). The decreased mPR3 in turn, may limit the targets to which PR3-specific ANCA can bind, and in turn, attenuates neutrophil activation. Moreover, without wishing to be bound by theory, because autoantibodies in patients with MPA bind to surface PR3 and/or to stimulate NSP release and subsequent tissue damage, the pharmacological effects of Compound A on neutrophils may treat MPA and other myeloperoxidase (MPO)-ANCA related disorders by reducing activities of NSP to decrease the tissue damage following neutrophil degranulation.

The three NSPs, abundantly secreted into the extracellular environment upon neutrophil activation at inflammatory sites, are thought to act in combination with reactive oxygen species to assist in degradation of engulfed microorganisms inside phagolysosomes. A fraction of the released proteases remains bound in an active form on the external surface of the plasma membrane so that both soluble and membrane-bound NSPs can regulate the activities of a variety of biomolecules such as chemokines, cytokines, growth factors, and cell surface receptors. Regulation is thought to occur by either converting the respective biomolecule to an active form or by degrading the biomolecule by proteolytic cleavage. Secreted proteases can stimulate mucus secretion and inhibit mucociliary clearance, but also activate lymphocytes and cleave apoptotic and adhesion molecules (Bank and Ansorge (2001). J Leukoc Biol. 69, pp. 197-206; Pham (2006). Nat Rev Immunol. 6, pp. 541-550; Meyer-Hoffert (2009). Front Biosci. 14, pp. 3409-3418; Voynow et al. (2004). Am J Physiol Lung Cell Mol Physiol. 287, pp. L1293-302; the disclosure of each of which is incorporated by reference in its entirety for all purposes).

In some embodiments, the treatment methods provided herein comprise the administration of a composition comprising an effective amount of a compound of Formula (I), or a pharmaceutically acceptable salt thereof, to a patient in need of treatment of an ANCA associated vasculitis. In one embodiment, a composition comprising an effective amount of a compound of Formula (I) is administered orally. In one embodiment, the compound is Compound A, or a pharmaceutically acceptable salt thereof. In a further embodiment, administration is 1× daily, twice daily, once every other day, once every third day, once every fourth day, 2× weekly, 3× weekly or 4× weekly. In even a further embodiment, administration is once daily. In even a further embodiment, administration is oral once daily.

In one embodiment of the method of treatments provided herein, treating a patient for an ANCA associated vasculitis comprises decreasing the Birmingham Vasculitis Activity Score (BVAS) for the patient, as compared to the BVAS score prior to treatment (Suppiah et al. (2011). Rheumatology 50, pp. 899-905; Mukhtyar et al (2009). "Modification and validation of the Birmingham Vasculitis Activity Score (version 3) ARD 2009 68:1827, each incorporated by reference herein in its entirety for all purposes). Such a decrease in one embodiment, can be a decrease to 0, i.e., where the treating achieves remission of the ANCA associated vasculitis.

In another embodiment, treating a patient comprises maintaining the BVAS score at 0, i.e., maintaining remission. The BVAS score measures the disease activity in patients with a variety of systemic vasculitides and scores abnormality ascribable to the presence of active vasculitis. Selga et al. (2006). Rheumatology 45, pp. 1276-1281, incorporated by reference herein in its entirety for all purposes.

The BVAS evaluation form includes: 56 disease items characterized in 9 groups and an "other" section. Items on the BVAS evaluation form are counted only if they are attributable to active vasculitis. The maximum possible score is 63. A score of 0 indicates disease remission, while a score of ≥1 indicates an active disease state (Suppiah et al. (2011). Rheumatology 50, pp. 899-905, incorporated by reference herein in its entirety for all purposes).

In one embodiment, the ANCA associated vasculitis is microscopic polyangiitis (MPA) and a method is provided for treating a patient in MPA remission and maintaining the remission in the patient. The method comprises administering to the patient a composition comprising an effective amount of a compound of Formula (I), or a pharmaceutically acceptable salt thereof. Remission, in one embodiment is measured by a BVAS score of 0 prior to the treatment and a BVAS score of 0 during the treatment, or subsequent to the treatment. In a further embodiment, the compound of Formula (I) is Compound A, or a pharmaceutically acceptable salt thereof. In one embodiment, the composition is administered orally. In yet a further embodiment, administration is 1× daily, twice daily, once every other day, once every third day, once every fourth day, 2× weekly, 3× weekly or 4× weekly. In even a further embodiment, administration is 1× daily. In one embodiment, administration is oral, 1× daily.

In one embodiment, the ANCA associated vasculitis is microscopic polyangiitis (MPA), and a method for treating an MPA patient comprises decreasing the patient's BVAS score to 0, from a BVAS score of ≥1. The method comprises administering to the patient a composition comprising an effective amount of a compound of Formula (I). In a further embodiment, the compound of Formula (I) is Compound A, or a pharmaceutically acceptable salt thereof. In one embodiment, the composition is administered orally. In yet a further embodiment, administration is 1× daily, twice daily, once every other day, once every third day, once every fourth day, 2× weekly, 3× weekly or 4× weekly. In even a further embodiment, administration is 1× daily. In even a further embodiment, administration is oral, 1× daily.

In one embodiment, the ANCA associated vasculitis is granulomatosis with polyangiitis (GPA), and a method for treating GPA in a patient in need thereof is provided. The patient may be in an active disease state or in remission, for example, as measured by the Birmingham Vasculitis Activity Score specific for Wegener's granulomatosis (BVAS/WG). Stone et al. (2001). A disease-specific activity index for Wegener's Granulomatosis. *Arthritis & Rheumatism* 44(4), pp. 912-920, incorporated by reference herein in its entirety for all purposes.

The BVAS/WG evaluation form includes: (1) 34 separate disease items, categorized into 9 groups; (2) an "other" section; (3) an asterisk by the 15 major items (i.e., an item that constitutes an immediate threat to the patient's life or to the function of a vital organ); (4) tick boxes to indicate new/worse or persistent disease; (5) an area to total the scores; (6) a section for the designation of disease status; (7) the physician's global assessment (PGA) of disease activity scale; and (8) a box for administrative use that contains information about the patient identification code and clinical center. Items on the BVAS/WG evaluation form are counted only if they result from active WG, and not from damage from previously active WG or another medical condition. The BVAS/WG includes categorical ratings that incorporate major and minor items into the definitions of disease status. Stone et al. (2001). *Arthritis & Rheumatism* 44(4), pp. 912-920, incorporated by reference herein in its entirety for all purposes. The four disease statuses are as follows:
(1) severe disease/flare (occurrence of any new/worse item that is major),
(2) limited disease/flare (occurrence of any new/worse item that is minor),
(3) persistent disease (presence of ≥1 item representing active disease that has continued since the patient's previous evaluation), and
(4) remission (no active disease; that is, no new/worse and no persistent items present).

The BVAS/WG score is calculated by multiplying the number of major items (either new/worse or persistent) by 3 and adding this number to the total number of minor items. The maximum BVAS/WG score, therefore, is 68, assuming that not more than 1 major and 1 minor "other" items are present. Stone et al. (2001). *Arthritis & Rheumatism* 44(4), pp. 912-920, incorporated by reference herein in its entirety for all purposes.

For a patient in an active disease state, in one embodiment, the method comprises decreasing the Birmingham Vasculitis Activity Score specific for Wegener's granulomatosis (BVAS/WG) for the patient, as compared to the BVAS/WG score prior to the treatment. In a further embodiment, a composition comprising an effective amount of a compound of Formula (I) is administered orally. In a further embodiment, the compound of Formula (I) is Compound A, or a pharmaceutically acceptable salt thereof. In yet a further embodiment, administration is 1× daily, twice daily, once every other day, once every third day, once every fourth day, 2× weekly, 3× weekly or 4× weekly. In yet a further embodiment, administration is 1× daily. In even a further embodiment, administration is oral, once daily.

In one embodiment of the method of treatments provided herein, treating GPA in a patient in need thereof comprises inhibiting a GPA flare. A GPA flare, as used herein, in one embodiment, is defined as an increase in the BVAS/WG score of 1 point or more. In a further embodiment, a composition comprising an effective amount of a compound of Formula (I) is administered orally to inhibit the GPA flare. In a further embodiment, the compound of Formula (I) is Compound A, or a pharmaceutically acceptable salt thereof. In yet a further embodiment, administration is 1× daily, twice daily, once every other day, once every third day, once every fourth day, 2× weekly, 3× weekly or 4× weekly. In yet a further embodiment, administration is 1× daily. In even a further embodiment, administration is oral once daily.

In another embodiment, the ANCA associated vasculitis is granulomatosis with polyangiitis (GPA), and the patient is in GPA remission, as indicated by, for example, a BVAS/WG of 0. The method in one embodiment comprises maintaining remission of the GPA in the patient. The patient may be in remission for at least 30, 60, 90, or 120 days prior to treatment. The patient, in one embodiment, maintains remissions during treatment and/or subsequent to treatment. Remission can be measured, in one embodiment, 1 day, 7 days, 14 days, 30 days, 60 days, 90 days or 120 days subsequent to the treatment. The patient treated with one of the methods provided herein, in one embodiment, has undergone or is currently undergoing GPA therapy with an anti-CD20 antibody (e.g., rituximab), cyclophosphamide, or a steroid (e.g., a corticosteroid, such as a glucocorticoid). In one embodiment, the compound of Formula (I) is Compound A, or a pharmaceutically acceptable salt thereof. In one embodiment, the composition is administered orally. In yet a further embodiment, administration is 1× daily, twice daily, once every other day, once every third day, once every fourth day, 2× weekly, 3× weekly or 4× weekly. In yet a further embodiment, administration is 1× daily. In even a further embodiment, administration is oral once daily. In one embodiment, the Compound A or a pharmaceutically acceptable salt thereof is administered orally at from about 10 mg to about 50 mg, or from about 20 mg to about 45 mg, e.g., 10 mg, 25 mg, 30 mg, or 40 mg, once daily. In another embodiment, the Compound A is administered orally at 40 mg once daily.

The treatment methods of the present disclosure can be employed to treat a patient in GPA remission to maintain the remission. Alternatively, the methods of the present disclosure can be employed to treat a patient with active GPA, in order to affect remission in the patient.

In some embodiments, treatment efficacy is defined by a lack of relapse, or a slowing of a relapse, as compared to a patient not treated via one of the methods provided herein. The relapse may be a major relapse or a minor relapse. A major relapse is defined as reappearance or worsening of disease with (1) a BVAS/WG≥0 and involvement of at least one major organ, (2) a life-threatening manifestation, or (3) both (1) and (2). A minor relapse is defined as reappearance or worsening of disease with a BVAS/WG≥0, not corresponding to a major relapse, but requiring mild treatment intensification.

Other measures of efficacy include rate of flares, time to relapse, change in Vasculitis Damage Index (VDI) from baseline, systemic corticosteroid use based on total oral corticosteroid dose and duration of oral corticosteroid use, and change in quality of life from baseline measured by, e.g., the short form health survey questionnaire (SF-36) score (discussed below).

VDI is a standardized clinical measure of damage in the systemic vasculitides. See Exley et al. (1997), Arthritis Rheum. 40(2):371-80, incorporated herein by reference in its entirety. VDI records the presence or absence of 64 items of damage separated into eleven groupings, which include ten organ-based systems and one general category as follows: (1) Musculoskeletal; (2) Skin; (3) Ear, nose, and throat; (4) Pulmonary; (5) Cardiovascular; (6) Renal; (7) Gastrointestinal; (8) Peripheral vascular; (9) Ocular; (10) Neuropsychiatric; and (11) Other damage.

The VDI score is the simple sum of the damage items and cumulative, i.e., all previously scored items are carried over to each subsequent assessment, and thus can only remain stable or increase.

In another embodiment of the method of treatments provided herein, treating a patient in need thereof comprises improving the short form health survey questionnaire (SF-36) score for the patient, as compared to the SF-36 score of the patient prior to treatment. The SF-36 measures eight scales: physical functioning (PF), role physical (RP), bodily pain (BP), general health (GH), vitality (VT), social functioning (SF), role emotional (RE), and mental health (MH). See, e.g., Lins and Carvalho (2016). SAGE Open Medicine 4, pp. 1-12, incorporated by reference herein in its entirety for all purposes. In a further embodiment, a composition comprising an effective amount of a compound of Formula (I) is administered orally. In a further embodiment, the compound of Formula (I) is Compound A, or a pharmaceutically acceptable salt thereof. In yet a further embodiment, administration is 1× daily, twice daily, once every other day, once every third day, once every fourth day, 2× weekly, 3× weekly or 4× weekly. In yet a further embodiment, administration is 1× daily. In even a further embodiment, administration is oral once daily.

In another embodiment of the method for treating an ANCA associated vasculitis provided herein, a composition comprising an effective amount of a compound of Formula (I), or a pharmaceutically acceptable salt thereof, is administered to a patient in need thereof. The method comprises decreasing intra-leukocyte proteinase 3 (PR3) activity, as compared to the patient's intra-leukocyte PR3 activity, prior to treatment. The compound of Formula (I) in a further embodiment, is Compound A, or a pharmaceutically acceptable salt thereof. In one embodiment, the composition is administered orally to the patient in need of treatment. In yet a further embodiment, administration is 1× daily, twice daily, once every other day, once every third day, once every fourth day, 2× weekly, 3× weekly or 4× weekly. In yet a further embodiment, administration is 1× daily. In even a further embodiment, administration is oral once daily.

In one embodiment, the PR3 activity is measured in leukocytes (e.g., neutrophils) obtained from the patient's whole blood. In another embodiment, the PR3 activity is measured in leukocytes (e.g., neutrophils) obtained from the patient's sputum. In one embodiment, the decreasing is by about 10%, about 20%, about 25%, about 30%, about 40%, about 50%, about 60%, about 70%, or about 80%. In another embodiment, decreasing PR3 activity comprises decreasing by at least about 1%, at least about 5%, at least about 10%, at least about 20%, at least about 30%, at least about 40%, at least about 50%, at least about 60%, at least about 70%, or at least about 80%. In one embodiment, the compound of Formula (I) is Compound A, or a pharmaceutically acceptable salt thereof. In one embodiment, the composition is administered orally. In yet a further embodiment, administration is 1× daily, twice daily, once every other day, once every third day, once every fourth day, 2× weekly, 3× weekly or 4× weekly. In yet a further embodiment, administration is 1× daily. In even a further embodiment, administration is oral once daily.

In another embodiment of the method of treatments provided herein, treating a patient in need thereof comprises administering to the patient a pharmaceutical composition comprising an effective amount of a compound of Formula (I), or a pharmaceutically acceptable salt thereof, and decreasing the neutrophil cell surface expression of proteinase 3 of the patient, as compared to the neutrophil cell surface expression of proteinase 3 prior to treatment. In one embodiment, decreasing comprises decreasing the PR3 neutrophil cell surface expression by about 10%, about 20%, about 25%, about 30%, about 40%, about 50%, about 60%, about 70%, or about 80%. In another embodiment, decreasing proteinase 3 cell surface expression comprises decreasing by at least about 1%, at least about 5%, at least about 10%, at least about 20%, at least about 30%, at least about 40%, at least about 50%, at least about 60%, at least about 70% or at least about 80%. In one embodiment, the compound of Formula (I) is Compound A, or a pharmaceutically acceptable salt thereof. In a further embodiment, the composition is administered orally. In yet a further embodiment, administration is 1× daily, twice daily, once every other day, once every third day, once every fourth day, 2× weekly, 3× weekly or 4× weekly. In yet a further embodiment, administration is 1× daily. As such, in one embodiment, the composition is administered orally and once daily.

In another embodiment of the method for treating an ANCA associated vasculitis (e.g., GPA or MPA), a composition comprising an effective amount of a compound of Formula (I), or a pharmaceutically acceptable salt thereof, is administered to a patient in need of the treatment, wherein the method comprises decreasing the neutrophil serine protease (NSP) activity in the patient's blood, as compared to the patient's NSP activity, prior to treatment. The compound of Formula (I) in one embodiment is Compound A, or a pharmaceutically acceptable salt thereof. In one embodiment, the composition is administered orally. In one embodiment, administration 1× daily, twice daily, once every other day, once every third day, once every fourth day, 2× weekly, 3× weekly or 4× weekly. In a further embodiment, administration is 1× daily. In a further embodiment, administration is oral once daily. In even a further embodiment, the compound of Formula (I) is Compound A. The NSP may be neutrophil elastase (NE), proteinase 3 (PR3) and/or cathepsin G (CatG). In one embodiment, decreasing NSP activity is by about 10%, about 20%, about 25%, about 30%, about 40%, about 50%, about 60%, about 70%, or about 80%. In another embodiment, decreasing NSP activity comprises decreasing NSP activity by at least about 1%, at least about 5%, at least about 10%, at least about 20%, at least about 30%, at least about 40%, at least about 50%, at least about 60%, at least about 70%, or at least about 80%.

In yet another embodiment of the method for treating an ANCA associated vasculitis (e.g., GPA or MPA) provided herein, a composition provided herein, comprising an effective amount of a compound of Formula (I), or a pharmaceutically acceptable salt thereof, is administered to a patient in need thereof, wherein the method comprises decreasing the patient's ANCA blood concentration, as compared to the patient's ANCA blood concentration prior to treatment. In one embodiment, the composition is administered via oral administration. The compound of Formula (I) in one embodiment is Compound A, or a pharmaceutically acceptable salt thereof. In one embodiment, the ANCA blood concentration is measured in the patient's blood plasma or blood serum. In a further embodiment, administration is 1× daily, twice daily, once every other day, once every third day, once every fourth day, 2× weekly, 3× weekly or 4× weekly. In one embodiment, administration is oral once daily.

In one embodiment, the method comprises decreasing the ANCA blood concentration of the patient by about 10%, about 20%, about 25%, about 30%, about 40%, about 50%, about 60%, about 70%, or about 80%. In another embodiment, decreasing ANCA blood concentration comprises decreasing by at least about 1%, at least about 5%, at least about 10%, at least about 20%, at least about 30%, at least about 40%, at least about 50%, at least about 60%, at least about 70%, or at least about 80%. In one embodiment, the ANCA blood concentration is measured in the patient's blood plasma or blood serum.

In one embodiment, decreasing the ANCA antibody concentration comprises decreasing the PR3 ANCA antibody concentration in the patient, as compared to the PR3 ANCA antibody concentration prior to treatment. In another embodiment, decreasing the ANCA antibody concentration comprises decreasing the MPO ANCA antibody concentration in the patient, as compared to the MPO ANCA antibody concentration prior to treatment.

In yet another embodiment of the method for treating an ANCA associated vasculitis (e.g., GPA or MPA) provided herein, a composition provided herein, comprising an effective amount of a compound of Formula (I), or a pharmaceutically acceptable salt thereof, is administered to a patient in need thereof, wherein the method comprises decreasing the number of CD19+ B-cells in the patient, as compared to the number of CD19+ B-cells in the patient, prior to treatment. The compound of Formula (I), in one embodiment, is Compound A, or a pharmaceutically acceptable salt thereof. In one embodiment, the composition is administered via oral administration. In a further embodiment, administration is 1× daily, twice daily, once every other day, once every third day, once every fourth day, 2× weekly, 3× weekly or 4× weekly. In one embodiment, administration 1× daily. In another embodiment, administration is oral once daily.

A composition comprising a compound of Formula (I), or a pharmaceutically acceptable salt thereof, may also be administered in conjunction with a further compound used for the treatment of an ANCA associated vasculitis (e.g., GPA or MPA) via one of the methods described herein.

The further compound is administered concurrently, sequentially or in admixture with a composition comprising a compound of Formula (I), for the treatment of an ANCA associated vasculitis.

The further compound, in one embodiment, is an anti-TNF-α antibody, e.g., infliximab, adalimumab, certolizumab pegol, and golimumab. In a further embodiment, the anti-TNF-α antibody is infliximab.

The further compound, in another embodiment, is an anti-CD20 antibody, e.g., rituximab, ocrelizumab, obinutuzumab, ofatumumab, ibritumomab, tiuxetan, tositumomab, and ublituximab. In a further embodiment, the anti-CD20 antibody is rituximab.

In yet another embodiment, the further compound is a steroid. In a further embodiment, the steroid is a corticosteroid. In even a further embodiment, the further compound is a glucocorticoid.

In even another embodiment, the further compound is cyclophosphamide (CYC), alone or in combination with one or more glucocorticoids.

In one combination therapy embodiment, the composition of the present disclosure is administered concurrently or sequentially with one or more further active ingredients selected from one or more of those provided above. For example, the composition comprising a compound of Formula (I), or a pharmaceutically acceptable salt thereof, may be administered concurrently or sequentially with a further pharmaceutical composition for use as a medicament for the treatment of an ANCA associated vasculitis. The further pharmaceutical composition may be a medicament which the patient may already be prescribed (e.g., an existing standard of care medication), and may itself be a composition comprising one or more active ingredients selected from those defined above.

EXAMPLES

The present invention is further illustrated by reference to the following Examples. However, it is noted that these Examples, like the embodiments described above, are illustrative and are not to be construed as restricting the scope of the invention in any way.

Example 1—Manufacture of Film-Coated Tablet Comprising Compound A

The film-coated tablet is manufactured using a dry granulation process, followed by tablet compression. The tablets are then coated with a hypromellose-based film coat where the coating excipients are suspended in purified water. No organic solvents are used in the manufacture.

A brief summary of the core tablet manufacturing process, and a summary of the coating process follows. Compound A is dry blended with microcrystalline cellulose, dibasic calcium phosphate dihydrate, sodium starch glycolate and silicon dioxide. Compound A may be de-lumped prior to dispensing if necessary. The amount of Compound A is corrected for purity and formula adjusted accordingly at the expense of microcrystalline cellulose.

The blend is co-milled and then dry blended with intra-granular glyceryl behenate. The lubricant may be charged together with a similar volume of microcrystalline cellulose excluded from the first dry blending step.

Ribbons are produced by roller compacting the lubricated dry blend. Subsequently the ribbons are milled into granules. The granules are blended with the extra-granular glyceryl behenate before being compressed into tablet cores.

Finally, the tablet cores are coated with a non-functional aesthetic film coat. The film coating mixture is prepared by adding the coating excipients into purified water, while mixing, in an appropriately sized vessel. Spray process parameters may be adjusted throughout the process in order to achieve the targeted weight gain per tablet. When complete the tablets are dried and discharged into an appropriate bulk container.

The excipients in the tablet core and the corresponding standards are summarized in Table 1, below.

TABLE 1

Specifications for excipients in tablet cores

| Components[a] | Standard |
| --- | --- |
| Cellulose, microcrystalline/microcrystalline cellulose | Ph, Eur or NF |
| Calcium hydrogen phosphate dihydrate/dibasic calcium phosphate dihydrate | Ph, Eur or USP |
| Sodium starch glycolate | Ph, Eur or NF |
| Silica, colloidal hydrated/Silicon dioxide | Ph, Eur or NF |
| Glycerol dibehenate/Glyceryl behenate | Ph, Eur or NF |

[a]No materials of animal origin are included in the drug product.

The excipients included in the tablet coating and their corresponding standards are summarized in Table 2. These can be added as a proprietary composite, e.g., Aquarius Prime BAP312542.

TABLE 2

Specifications for excipients in film-coating

| Components[a] | Standard |
| --- | --- |
| Hypromellose | Ph, Eur or USP |
| Macrogols/Polyethylene glycol | Ph, Eur or NF |
| Titanium dioxide | Ph, Eur or USP |
| Iron oxide red | E172 or NF |
| Iron oxide yellow | E172 or NF |
| Iron oxide black | E172 or NF |

[a]No materials of animal origin are included in the drug product.

Example 2—Excipient Compatibility with Compound A

Excipient compatibility experiments were designed as linear D-optimal designs with qualitative factors of two or more levels. The formulations used in these experiments can be directly compressed into tablets. For dry processing, three factors were evaluated, namely binary filler combination, choice of disintegrant and choice of lubricant. In the experimental design shown below (see Table 3) the effect of an HPMC-based film coat as well as the addition of colloidal silicon dioxide was evaluated using repeat corners.

Two different filler combinations were chosen for excipient compatibility, namely microcrystalline cellulose (MCC) in combination with dicalcium phosphate dihydrate (DCPD) and mannitol (MAN) in combination with MCC.

Three disintegrants were evaluated in this study: (i) croscarmellose sodium (an internally cross-linked carboxymethylcellulose sodium or NaCMC), (ii) low-substituted hydroxypropyl cellulose (L-HPC) and (iii) sodium starch glycolate (NaSG). The amount of disintegrant was varied to obtain similar disintegrating power.

The lubricants magnesium stearate (MgSt) and sodium stearyl fumarate (NaSF) were compared with glyceryl behenate. The amount of lubricant was varied to obtain similar lubrication effect.

Because of the cohesive nature of Compound A, a glidant was evaluated for high drug load drug products. Hence, colloidal silicon dioxide ($SiO_2$) was included in this study. The tablets in two experiments were coated with a film-coat containing three iron oxides that are globally acceptable.

TABLE 3

Materials used in Example 1.

| Name | Abbreviation | Supplier | Grade | Amount [%]* |
|---|---|---|---|---|
| Compound A | API | AstraZeneca | C2b-I | 1.25% |
| Microcrystalline cellulose | MCC | FMC BioPolymer | Avicel PH-102 | ~60% or 25% |
| Mannitol | MAN | Roquette | Pearlitol 100SD | ~68% |
| Dibasic calcium phosphate dihydrate | DCPD | JRS Pharma | Emcompress | 25% |
| Croscarmellose | NaCMC | FMS BioPolymer | Ac-Di-Sol | 3% |
| Sodium starch glycolate | NaSG | JRS Pharma | Explotab | 4% |
| Low-substituted hydroxypropyl cellulose | L-HPC | Shin Etsu | LH-B1 | 5% |
| Magnesium stearate | MgSt | Peter Greven | Ligamed MF-2-V | 1% |
| Sodium stearyl fumarate | NaSF | Moehs | PRUV | 2% |
| Glycerol behenate | GlyBeh | Gattefossé | Compritol 888 ATO | 3% |
| Colloidal silicon dioxide | SiO2 | Cabot | Cab-O-Sil | 0.25% |
| Film-coat premix | Coat | Colorcon | Opadry Beige 03B27164 | 4% |

TABLE 4

Experimental design for Compound A Excipient Compatibility Study

| Experiment Name | Run Order | Filler Combination | Disintegrant | Lubricant | Comments |
|---|---|---|---|---|---|
| N1 | 1 | MCC/DCPD | NaCMC | MgSt | |
| N2 | 9 | MAN/MCC | L-HPC | MgSt | |
| N3 | 4 | MAN/MCC | NaSG | MgSt | |
| N4 | 6 | MAN/MCC | NaCMC | GlyBeh | |
| N5 | 8 | MAN/MCC | L-HPC | GlyBeh | |
| N6 | 5 | MCC/DCPD | NaSG | GlyBeh | |
| N7 | 7 | MAN/MCC | NaCMC | NaSF | |
| N8 | 2 | MCC/DCPD | L-HPC | NaSF | |
| N9 | 3 | MAN/MCC | NaSG | NaSF | |
| N10 | 10 | MCC/DCPD | NaCMC | MgSt | Coated N1 |
| N11 | 11 | MAN/MCC | L-HPC | GlyBeh | $SiO_2$ coated N5 |
| N12 | 12 | MCC/DCPD | NaCMC | MgSt | $SiO_2$ 90 mg RC coated N1 |

N1 (Table 4) was considered the primary choice initially, hence it was used as one repeat corner, and that repeat experiment was film-coated. N5 was the opposite of N1 and used as the other repeat corner. Colloidal silicon dioxide was added to that repeat experiment. Finally, a modified N1 formulation with a high drug load was roller compacted (RC) to make sure that there were no implications of using that manufacturing route.

The accelerated stability program used is shown in Table 5, below. Pure drug substance was included as a reference in all conditions.

TABLE 5

Compound A accelerated stability assessment program

| Condition [° C./% RH] | First time point [days] | Second time point [days] | Third time point [days] |
|---|---|---|---|
| 50/XX | 21[2] | 45 | 65[1] |
| 50/75 | 21 | 45[1] | 65[1] |
| 60/40 | 21[2] | 45[1] | 65[1] |
| 70/XX | 21[2] | 45[3] | 65[2] |
| 70/75 | 2[1] | 6 | 21[3] |

RH: relative humidity;
XX: Ambient relative humidity (~5% assumed)
[1]Not evaluated;
[2]Not tested;
[3]Not used for the shelf life prediction model

TABLE 6

Tablet performance data.

| Experiment | CP [MPa] | TS [MPa] | $CP_{norm}$ [MPa] | $m_{var}$ [% RSD] |
|---|---|---|---|---|
| N1 | 85 | 2.3 | 75 | 1.0 |
| N2 | 113 | 2.5 | 88 | 0.9 |
| N3 | 122 | 2.8 | 87 | 0.4 |
| N4 | 117 | 2.7 | 85 | 0.3 |
| N5 | 114 | 2.6 | 88 | 0.7 |
| N6 | 83 | 2.3 | 71 | 0.7 |
| N7 | 125 | 2.7 | 94 | 0.4 |
| N8 | 94 | 2.2 | 85 | 1.3 |
| N9 | 132 | 2.9 | 92 | 0.3 |
| N10* | — | — | — | — |
| N11 | 118 | 2.6 | 91 | 0.6 |
| N12* | — | — | — | — |

RSD: relative standard deviation
*Tablet performance data was not determined

Results

Figure 2:
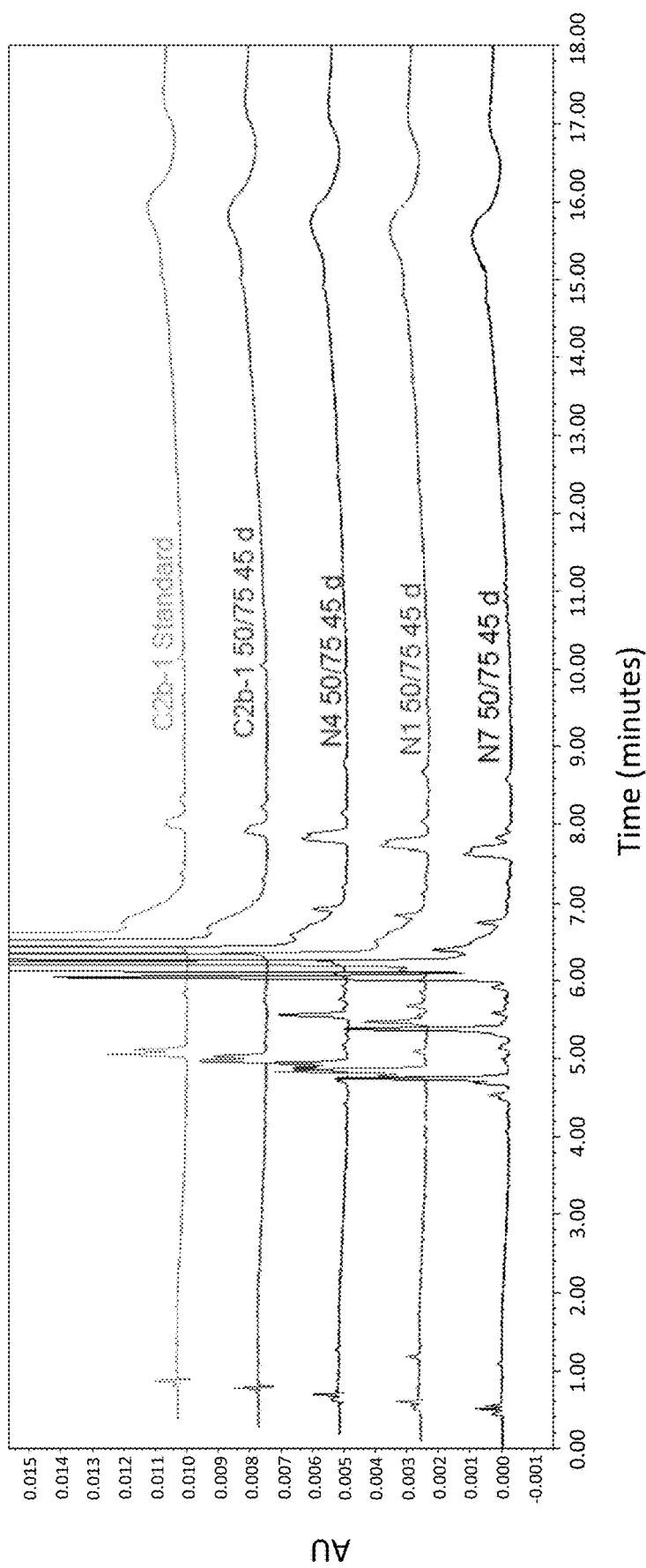
FIG. 2 are overlaid chromatograms of three of the tested compositions with different lubricants compared with API (Compound A) and standard. The chromatograms are slightly offset for clarity.

The drug product in the tablets tested degrade at a significantly faster rate than the neat drug substance (i.e., Compound A), in all conditions tested. Hence, there are incompatibilities between all excipients, but some excipients accelerate the degradation more than others. This is shown in FIG. 2, where tablets stored at 50/75 for 45 days are compared with neat drug substance stored in identical conditions as well as a freshly prepared standard solution from the same drug substance batch. The chromatograms are stacked in order of degradation (and slightly shifted for clarity).

The most degradation is seen for Batch N7, which contains NaSF as the lubricant. Most degradation peaks are significantly larger than the other batches, and one peak was not present in the other batches. This peak could be linked to a specific incompatibility between NaSF and Compound A. N1 is also slightly more degraded than N4, but there is almost no difference between the drug substance on stability and the freshly prepared standard.

The data from batches stored at 70/75 for 21 days displayed extreme levels of degradation, including secondary degradation, hence that data was not used to draw any conclusions about the relative stability of the excipients. However, the general trends from the other conditions could still be seen. In 70/XX the degradation profile looked significantly different from the other conditions. This is believed, without wishing to be bound by any particular theory, to be related to a physical form change of Compound A. The degradation profile seen for 50/XX and 70/75 matched those of 50/75 and 60/40, hence the drug substance is believed to have been physically stable at those conditions, at least for the time period investigated. Based on this, 70/XX data was omitted from the shelf life prediction model.

More than 2 megapascal (MPa) tablet tensile strength (TS) was achieved well below 150 MPa compaction pressure (CP) (Table 6). The normalized compaction pressure ($CP_{norm}$) for all batches are below 100 MPa, which is excellent. Finally, the mass variability are all below 1.5% and most are below 1% RSD. However, those values would change significantly for an optimum formulation and process that also included roller compaction.

Five different peaks were monitored at five different conditions. However, as discussed above, the 70/XX condition was excluded based on a probable conversion to Form B. Overall, Compound A in tablets containing glyceryl behenate appears to degrade to a slightly lesser degree than magnesium stearate.

While MCC/DCPD may be slightly advantageous in humid conditions, MAN/MCC had an advantage in dry conditions. However, the differences were minor, hence compaction properties determined the final choice of fillers.

In some conditions, L-HPC seemed less stable, and in others NaCMC. Hence, NaSG appears to be optimal in terms of chemical compatibility.

N10 can be directly compared with N1 to assess the effect of a HPMC-based film-coat on the stability of the drug product. N11 can be directly compared with N5 to assess the effect of colloidal silicon dioxide. N12 was based on N1, but roller compacted and containing 25% drug load not 1.25%. Hence, the key purpose of that batch was to make sure that the proposed manufacturing route was feasible for a high drug load drug product.

Multiple Linear Regression (MLR) Degradation Monitoring

The stability conditions were selected in an experimental design fashion to determine the degradation based on temperature, humidity as well as the excipients chosen. Thus the data in were evaluated using multiple linear regression (MLR). Because of the likely form change when stored at 70/XX for 45 days, that data was excluded. As were data from N10, N11 and N12, since the evaluation above indicated that the changes from N1 and N5 were not insignificant.

Figure 3:
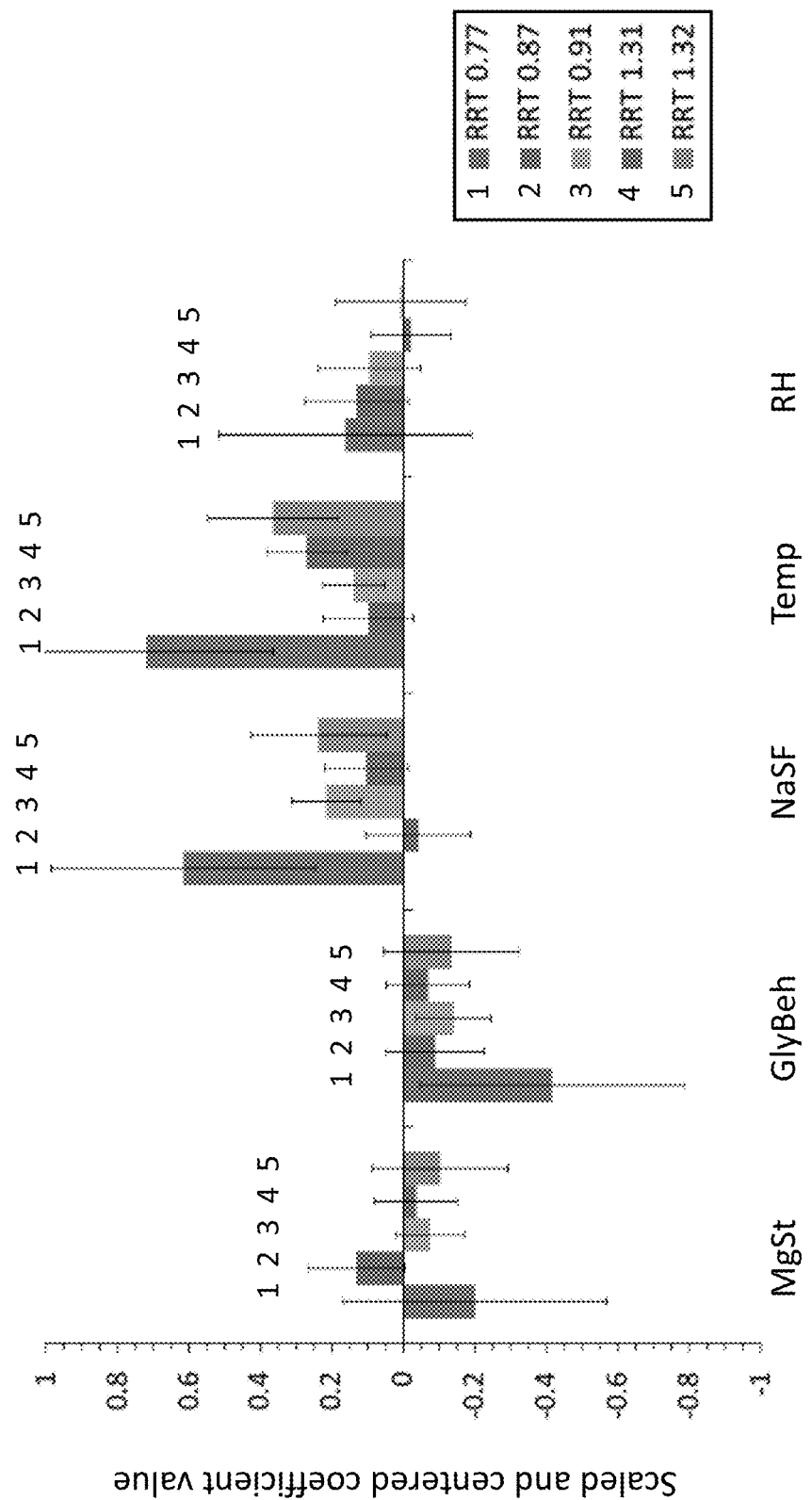
FIG. 3 shows the scaled and centered coefficient value obtained from the multiple linear regression (MLR) models for the five degradation products of Compound A as a function of excipient, temperature or relative humidity (RH).

Scaled and centered coefficients from the MLR models for the five degradation products are shown in FIG. 3. In short, GlyBeh appears better than MgSt, but the most important choice is to stay away from NaSF. Humidity is not a major concern, while increasing temperature does lead to more degradation.

Shelf Life Prediction

Chemical incompatibilities between excipients and Compound A were assessed using a modified Arrhenius expression shown in Equation 1. This approach uses the time to the specification limit in different storage conditions to predict the shelf life in other conditions (see Table 7).

$$k = k_0 e^{\frac{E_a}{RT}} e^{bH_r} \quad \text{Equation 1}$$

where k is the degradation rate constant for a degradation product, $k_0$ is the pre-exponential factor, T is the absolute temperature (in kelvins), $E_a$ is the activation energy for the degradation, R is the universal gas constant, b is the humidity sensitivity factor and $H_r$ is the relative humidity.

Figure 4:
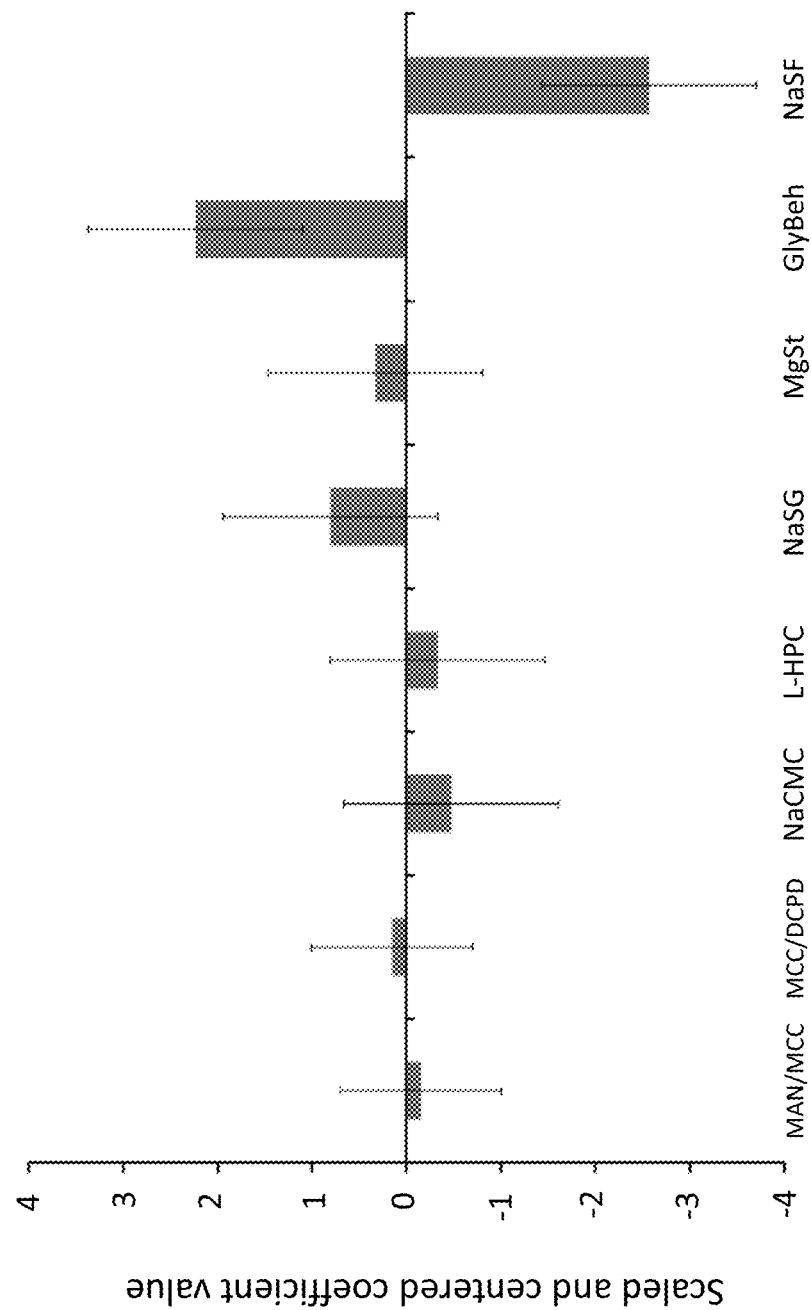
FIG. 4 shows the scaled and centered coefficient value from MLR analysis of shelf life prediction data for different excipients tested.

The results shown in Table 7 were generated by excluding the 70/XX data from the calculations. Furthermore, any model found unreliable was disregarded from the results shown. For example, no reliable models could be made for the RRT 0.91 peak. However, that degradation product was never the largest in any of the experiments, hence is unlikely to limit shelf life. The information in Table 7 was further evaluated with MLR to understand the influence of each of the excipients on the drug product shelf life. The model provided an $R^2$ of 0.96 and a $Q^2$ of 0.52. A coefficient plot is shown in FIG. 4. This model supports the results discussed above, where GlyBeh is a safer choice than MgSt in terms of chemical stability of Compound A.

TABLE 7

| Shelf life prediction at 25/60 | | |
|---|---|---|
| Experiment | Predicted shelf life | Lower 95% percentile |
| N1 | 2.2 | 2.0 |
| N2 | 3.0 | 2.7 |

TABLE 7-continued

| Shelf life prediction at 25/60 | | |
|---|---|---|
| Experiment | Predicted shelf life | Lower 95% percentile |
| N3 | 4.0 | 3.5 |
| N4 | 4.5 | 3.9 |
| N5 | 4.0 | 3.5 |
| N6 | 6.4 | 5.2 |
| N7 | 0.08* | N/A |
| N8 | 0.21* | N/A |
| N9 | 0.21* | N/A |

*Manually determined based on the RRT 1.03 peak, specific to NaSF degradation

The degradation peaks described herein can in all likelihood, be assigned according to Table 8, below. The diastereoisomer AZ13703978 and the dimer AZ13785489 did not change significantly in the excipient compatibility study, hence are not discussed herein.

TABLE 8

| Compound A degradation peak assignment | | |
|---|---|---|
| Relative retention time (RRT) | Probable degradation product | Molecular structure |
| 1.00 | Compound A | 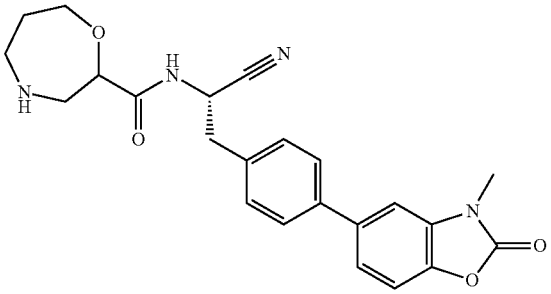 [SMILES: Cn1c(=O)oc2ccc(-c3ccc(C[C@@H](C#N)NC(=O)C4CNCCCO4)cc3)cc21] |
| 0.77 | AZ1370214 | 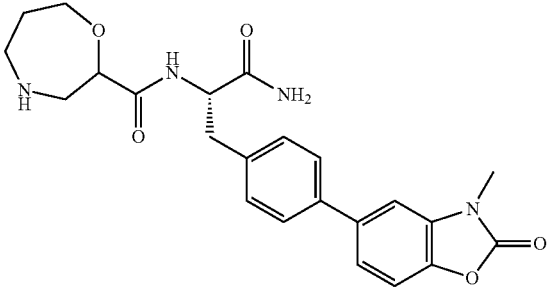 [SMILES: Cn1c(=O)oc2ccc(-c3ccc(C[C@H](NC(=O)C4CNCCCO4)C(N)=O)cc3)cc21] |
| 0.87 | Not yet named | 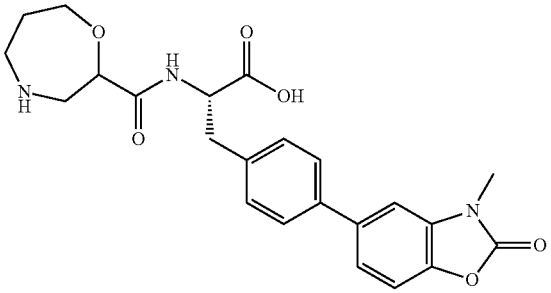 [SMILES: Cn1c(=O)oc2ccc(-c3ccc(C[C@H](NC(=O)C4CNCCCO4)C(=O)O)cc3)cc21] |

TABLE 8-continued

Compound A degradation peak assignment

| Relative retention time (RRT) | Probable degradation product | Molecular structure |
|---|---|---|
| 0.91 | Not yet determined | N/A |
| 1.03 | Not yet named (only present in combination with sodium stearyl fumarate) | [structure] |
| 1.31 | AZ13785488* | [structure] |
| 1.32 | AZ13910537* | [structure] |

*It is not currently possible to assign the diastereoisomers AZ13785488 and AZ13910537.

Tableting performance data was collected. The model obtained was very good with a regression coefficient ($R^2$) of 0.98 and a cross-correlation coefficient (Q2) of 0.90. The outcome states that MCC/DCPD is preferred over MAN/MCC and L-HPC and NaSF performed the worst for disintegrants and lubricants, respectively.

Example 3—Quantitative Formulation Development

In order to evaluate the influence of excipient ranges and one critical process parameter on the Compound A performance, a Fractional Factorial Resolution III experimental design was set up (Table 9). Materials used in these experiments are provided in Table 10.

TABLE 9

Experimental design.

| Exp. Name | Run order | Compound A | MCC | DCPD | NaSG | SiO$_2$ | GlyBeh | Roll Pressure (RP) |
|---|---|---|---|---|---|---|---|---|
| N1$^{D, I}$ | 3 | 1.25 | 76.25 | 15 | 2 | 0.5 | 5 | 8 |
| N2$^{D, I}$ | 6 | 16.25 | 63.25 | 15 | 2 | 0.5 | 3 | 4 |
| N3$^{I}$ | 11 | 1.25 | 66.75 | 25 | 2 | 0 | 5 | 4 |
| N4 | 4 | 16.25 | 53.75 | 25 | 2 | 0 | 3 | 8 |

TABLE 9-continued

Experimental design.

| Exp. Name | Run order | Compound A | MCC | DCPD | NaSG | SiO$_2$ | GlyBeh | Roll Pressure (RP) |
|---|---|---|---|---|---|---|---|---|
| N5[D, I] | 1 | 1.25 | 74.75 | 15 | 6 | 0 | 3 | 8 |
| N6[D] | 7 | 16.25 | 57.75 | 15 | 6 | 0 | 4 | 4 |
| N7[I] | 9 | 1.25 | 64.25 | 25 | 6 | 0.5 | 3 | 4 |
| N8[D, I] | 2 | 16.25 | 47.25 | 25 | 6 | 0.5 | 5 | 8 |
| N9 | 8 | 8.75 | 63 | 20 | 4 | 0.25 | 4 | 6 |
| N10[D, I] | 5 | 8.75 | 63 | 20 | 4 | 0.25 | 4 | 6 |
| N11 | 10 | 8.75 | 63 | 20 | 4 | 0.25 | 4 | 6 |

D: Dissolution testing on stability (Compound A, NaSG and GlyBeh investigated)
I: Degradation testing on stability (DCPD, SiO$_2$ and GlyBeh investigated)

TABLE 10

Materials used in Example 3.

| Name | Abbreviation | Supplier | Grade | Amount [%]* |
|---|---|---|---|---|
| Compound A | API | AstraZeneca | C2b-I | 1.25% |
| Microcrystalline cellulose | MCC | FMC BioPolymer | Avicel PH-102 | ~68% or 25% |
| Dibasic calcium phosphate dihydrate | DCPD | JRS Pharma | Emcompress | 15-25% |
| Sodium starch glycolate | NaSG | JRS Pharma | Explotab | 2-6% |
| Glycerol behenate | GlyBeh | Gattefosse | Compritol 888 ATO | 3-5% |
| Silicon dioxide | SiO2 | Grace | Syloid 244FP | 0-0.5% |
| Film-coat premix | Coat | Colorcon | Opadry Beige 03B27164 | 4% |

Drug Load

A possible dose range for Compound A is 5 mg to 65 mg, hence the drug load was chosen to accommodate that range, translating to 1.25% to 16.25%. The amount of drug substance was not corrected for purity, except for a 1:1 (mol/mol) water content. A center point level of 8.75% was chosen.

Binary Filler Level

The primary filler, microcrystalline cellulose, was allowed to vary freely to account for all other changes in the composition. The secondary filler, dibasic calcium phosphate dihydrate, was varied between 15% and 25%. These levels were selected to ensure that the yield pressure and strain rate sensitivity of each formulation was 110-160 MPa and 2%-25%, respectively. The maximum and minimum amount of microcrystalline cellulose was 76% and 47%, respectively.

Amount of Disintegrant

The amount of disintegrant was based on the usage statement in Pharmaceutical Excipients, namely that the usual concentration employed in a formulation is between 2% and 8%. In many instances, concentration employed is about 4%, although in many cases 2% is sufficient. Hence 2% was chosen as the low level and 4% as the center point. Based on symmetry, 6% was used for the high level.

Amount of Glidant

The effect of the glidant on degradation was not clear from Example 2, but an indication of an incompatibility between Compound A and colloidal silicon dioxide was noticed. For this reason, the low level was set at 0%. In the Compatibility Study of Example 2, 0.25% SiO$_2$ was used, hence this level was selected for the center point. In Example 2, colloidal silicon dioxide, Cab-O-Sil (Cabot Corp., Boston, MA, USA) was used, but for this experiment the silicon dioxide Syloid 244FP was selected for improved handling. The upper level of 0.5% was chosen for symmetry reasons.

Amount of Lubricant

In Example 2, it was noticed that 2% glyceryl behenate was insufficient to lubricate the directly compressed formulation containing 1.25% drug load. An additional experiment using 3% glyceryl behenate was manufactured to ensure that the stability benefits seen with glyceryl behenate would not diminish when a sufficient amount of lubricant was used, 3% was selected as the lower level of lubricant. Because the drug substance is quite adhesive, a higher drug load would require more lubrication, thus 5% was selected as the upper level, and 4% was used for the center point.

Amount of Film Coat

For the Example 3 coating experiment, a total amount of 3% coating solids was chosen, which corresponds to 4.8 mg/cm$^2$.

Process Parameter Variation

The compaction force was varied to understand how formulation process interplay. A suitable range on the Vector TFC-Labo roller compactor is 4 MPa to 8 MPa.

Evaluation of the Experimental Design

The experimental design was evaluated with respect to the responses discussed below using multiple linear regression (MLR). Primarily only linear coefficients was evaluated, but as discussed above the Fractional Factorial experimental design will allow for an interaction coefficient to be evaluated as well. The stability data was evaluated using a reduced experimental design.

Scanning Electron Microscopy

Scanning electron microscopy (SEM) images were collected for all steps from one of the center point batches, namely N11. A Cressington 108 Auto gold sputterer coated the materials with gold. The images were than captured using a FEI Quanta 200 scanning electron microscope equipped with an Everhart Thornley (SE) detector.

Roll Compaction Characterization
Ribbon Characterization

The true density of representative secondary blends were determined in duplicate using an AccuPyc 1330. The envelope density of the ribbons was measured using a GeoPyc 1360 Envelope Density Analyzer. The analysis was performed in duplicate using the following settings:
Sample amount: about 2 g
Sample chamber diameter: 25.4 mm
Number of cycles: 7
Consolidation force: 51 N
Conversion factor: 0.5153 cm3/mm The relative density of the ribbon, which is a good metric of the remaining compatibility of the material, was calculated by dividing the ribbon envelope density with the true density of a representative secondary blend.

Amount of Fines

A rudimentary measure of fines was determined by collecting the ribbons from the roller compactor onto a 2 mm mesh. The ribbons were dusted off on the screen, and everything passing through the mesh was weighed and called fines. This was compared to the total amount of material exiting the roller compactor.

Granule Characterization

The bulk density of the secondary blend was compared to the bulk density of the final blend as a measure of the density increase exerted by the roller compaction process. The bulk density was determined according to USP.

Granule Size Distribution

A Malvern Mastersizer 2000 (Malvern Instruments Ltd, Malvern, UK) laser diffraction analyzer was used for particle size distribution (PSD) measurements. Sample preparation was performed by gently adding 1 g of the sample on a measuring tray before placed in the dispersion unit. Three measurements were performed for each sample and average d[0.1], d[0.2], d[0.5], d[0.8] and d[0.9] calculated in the Malvern software. Furthermore, Span was calculated as a metric of the width of the size distribution.

Flowability Determination
Permeability

A Freeman Technology FT4 Powder Rheometer (Freeman Technology, Tewkesbury, UK) was used for measuring the pressure drop across the powder bed. Measurements were performed at increasing normal stresses between 1-30 kPa and with a constant airflow rate at 2 mm/s. At each normal stress, after airflow rate reached equilibrium at 2 mm/s, the pressure drop was measured in the powder bed. A scatter chart plotting the pressure drop across the powder bed as a function of the applied normal stress was constructed. Analysis of data was performed in the FT4 data analysis software.

Wall Friction Angle

The wall friction test is conducted by applying a wall normal stress on the sample with a decreasing pattern using the FT4 Powder Rheometer. Before starting the measurements, a blade is used to condition the sample, removing localized stress and excess air. A vented metal piston thereafter puts pressure from above to compact the powder bed. Finally, a metal piston with a plate of stainless steel, 1.2 μm in groove depth, compresses the powder sample while is rotated to measure the frictional resistance. The load was varied from 1 kPa to 15 kPa. A wall friction disk had a roughness of Ra 1.2 μm. An angle of 30° or more is considered adhesive. Angles significantly lower than 150 may lead to insufficient grip during roller compaction, poor compaction properties during tablet compression and possible dissolution issues if related to significant overlubrication.

Mass Flow Rate

Mass flow rates were measured with an Erweka GTB flow tester. The flow tester measures the predefined amount of powder (g) discharging from a hopper for a certain period (s) (Erweka GmbH, Heusenstamm, Germany). An orifice of 10 mm was used. The testing time was set to 10 s with a stirrer setting of 2. A value of 5 g/s or more is typically required for adequate die filling during tablet compression.

Drug Product Characterization
Compaction Properties

The compaction properties were determined using an Erweka MultiCheck Turbo 3.

Dissolution

The dissolution was determined initially for all batches, but during stability storage according to Table 9.

Degradation

The assay and organic impurities was determined initially for all batches, but during stability storage degradation was determined in accordance with Table 9.

Results

Initially the roller compactor was setup with the punch-type roll with a serrated surface, while the die-type roll had a smooth surface. The grip on the smooth roll was insufficient, hence the roller compaction did not work. The smooth punchtype roll was then changed to one with serrated surface, and the entire experimental design was completed with that setup. The first two experiments were re-run, but herein referred to as N5 and N8.

Roller Compaction Characterization

The roller compaction process was studied by determining the envelop density (ED) for each batch and then computing the relative density of the ribbon (RD).

The powder and granule bulk densities (PDB and GBD, respectively) was determined to understand fill volumes when scaling up the process. However, a density increase value (DI) was also calculated as a measure of the densification of the material during the roller compaction unit operation. Batch N1 stand out as very minimal densification, whereas N6 saw a 75% increase in bulk density. N11 is a clear outlier compared to the other two center points.

Finally, the amount of fines remaining following the roller compaction unit operation was determined. The difference in fines between batches is believed to be a relevant measure, but the overall level of fines is larger from the small-scale equipment used in this study, due to worn side seals.

Flowability Determination

The flowability of the final blends were analyzed using three different methodologies (Table 11). Permeability is a measure of the cohesive character of the final blend, whereas the wall friction angle determines the adhesiveness of the blend. Finally, the mass flow rate is a direct measure of the flowability of the blend.

TABLE 11

Flowability for final blends.

| Exp. Name | Mass flow rate [g/s] | Wall friction angle [°] | Permeability @ 50 kPa ×10$^9$ [cm$^2$] |
|---|---|---|---|
| N1 | 14.8 | 25.1 | 90 |
| N2 | 9.5 | ND | 14 |
| N3 | 9.8 | ND | 115 |

TABLE 11-continued

Flowability for final blends.

| Exp. Name | Mass flow rate [g/s] | Wall friction angle [°] | Permeability @ 50 kPa ×10$^9$ [cm$^2$] |
|---|---|---|---|
| N4 | 4.0 | 30.2 | 17 |
| N5 | 10.4 | ND | 84 |
| N6 | 4.0 | 29.7 | 14 |
| N7 | 14.6 | 23.8 | 78 |
| N8 | 9.5 | ND | 10 |
| N9 | 11.9 | ND | 39 |
| N10 | 12.5 | 28.7 | 40 |
| N11 | 5.5 | ND | 35 |

ND: Not determined

Drug Product Characterization

The most relevant physical tablet characteristics are shown in Table 12. CPnorm is an approximation of the compaction pressure required to produce a tablet with a tensile strength of 2.0 MPa. The mass variability is the relative standard deviation of the weight of 10 tablets. As is evident from the data in Table 12, the mass variability for all batches is 1.000 or less.

TABLE 12

Physical table characteristics of all batches.

| Exp. Name | CPnorm [MPa] | Mvar [% RSD] |
|---|---|---|
| N1 | 126 | 0.54 |
| N2 | 136 | 1.03 |
| N3 | 295 | 0.77 |
| N4 | N/A | N/A |
| N5 | 172 | 0.41 |
| N6 | 202 | 0.86 |
| N7 | 121 | 0.49 |
| N8 | 188 | 0.79 |
| N9 | 163 | 0.71 |
| N10 | 161 | 0.33 |
| N11 | 150 | 0.90 |

Batch N4 could not be compressed into tablets.

The dissolution data for all batches is listed in Table 13. All batches reach 85% dissolved within 15 minutes, and for all batches except N1 all Compound A is released within 10 minutes or less.

TABLE 13

Compound A dissolution results [% Compound A dissolved]

| Time [min.] | N1 | N2 | N3 | N5 | N6 | N7 | N8 | N9 | N10 | N11 |
|---|---|---|---|---|---|---|---|---|---|---|
| 5 | 69 | 89 | 89 | 106 | 92 | 99 | 90 | 119 | 130 | 134 |
| 10 | 85 | 94 | 99 | 109 | 96 | 101 | 96 | 129 | 136 | 139 |
| 15 | 93 | 95 | 101 | 109 | 97 | 102 | 97 | 132 | 136 | 139 |
| 20 | 97 | 95 | 101 | 109 | 97 | 102 | 97 | 133 | 136 | 139 |
| 25 | 99 | 95 | 101 | 109 | 97 | 102 | 97 | 134 | 136 | 139 |
| 30 | 101 | 95 | 101 | 109 | 97 | 102 | 97 | 134 | 136 | 139 |
| 45 | 103 | 96 | 101 | 109 | 98 | 102 | 98 | 135 | 137 | 139 |
| 60 | 103 | 96 | 101 | 109 | 98 | 102 | 98 | 135 | 137 | 139 |
| 75 | 103 | 96 | 102 | 109 | 98 | 102 | 98 | 136 | 137 | 140 |
| 90 | 104 | 97 | 102 | 110 | 98 | 102 | 98 | 136 | 137 | 140 |
| 105 | 104 | 97 | 102 | 110 | 98 | 102 | 98 | 136 | 137 | 140 |
| 120 | 104 | 97 | 102 | 110 | 99 | 102 | 98 | 137 | 138 | 140 |
| 135 | 104 | 98 | 102 | 110 | 99 | 102 | 99 | 138 | 138 | 140 |
| 150 | 104 | 98 | 102 | 110 | 99 | 102 | 99 | 138 | 138 | 140 |

Six selected batches were put in stability storage and analyzed with respect to dissolution. Only N1 was affected by the various storage conditions after 1 month, see Table 14, Table 15 and Table 16.

TABLE 14

Dissolution stability results at the 10 min. time point after 1 month.

| Exp. Name | Initial | 25/60 Open | 40/75 Closed | 40/75 Open | 50/XX Open |
|---|---|---|---|---|---|
| N1 | 85 | 66 | 71 | 75 | 67 |
| N2 | 94 | 96 | 95 | 94 | 97 |
| N5 | 109 | 108 | 110 | 110 | 108 |
| N6 | 96 | 97 | 96 | 97 | 97 |
| N8 | 96 | 96 | 96 | 96 | 97 |
| N10 | 97 | 93 | 94 | 96 | 98 |

TABLE 15

Dissolution stability results at the 30 min. time point after 1 month.

| Exp. Name | Initial | 25/60 Open | 40/75 Closed | 40/75 Open | 50/XX Open |
|---|---|---|---|---|---|
| N1 | 101 | 94 | 96 | 97 | 92 |
| N2 | 95 | 97 | 96 | 95 | 97 |
| N5 | 109 | 109 | 110 | 110 | 109 |
| N6 | 97 | 98 | 97 | 97 | 98 |
| N8 | 97 | 97 | 97 | 96 | 98 |
| N10 | 97 | 96 | 97 | 96 | 98 |

TABLE 16

Dissolution stability results at the 150 min. time point after 1 month.

| Exp. Name | Initial | 25/60 Open | 40/75 Closed | 40/75 Open | 50/XX Open |
|---|---|---|---|---|---|
| N1 | 104 | 103 | 102 | 103 | 104 |
| N2 | 98 | 98 | 98 | 98 | 99 |
| N5 | 110 | 109 | 110 | 111 | 109 |
| N6 | 99 | 100 | 100 | 100 | 99 |
| N8 | 99 | 99 | 100 | 99 | 99 |
| N10 | 99 | 98 | 99 | 98 | 99 |

Organic impurity data from 1-month stability storage was also collected at various conditions. No significant differences were found between storage at 5/XX and 25/60, and overall lower drug load lead to increased degradation. Degradation was significant in both 40/75 and 50/XX.

Figure 5:
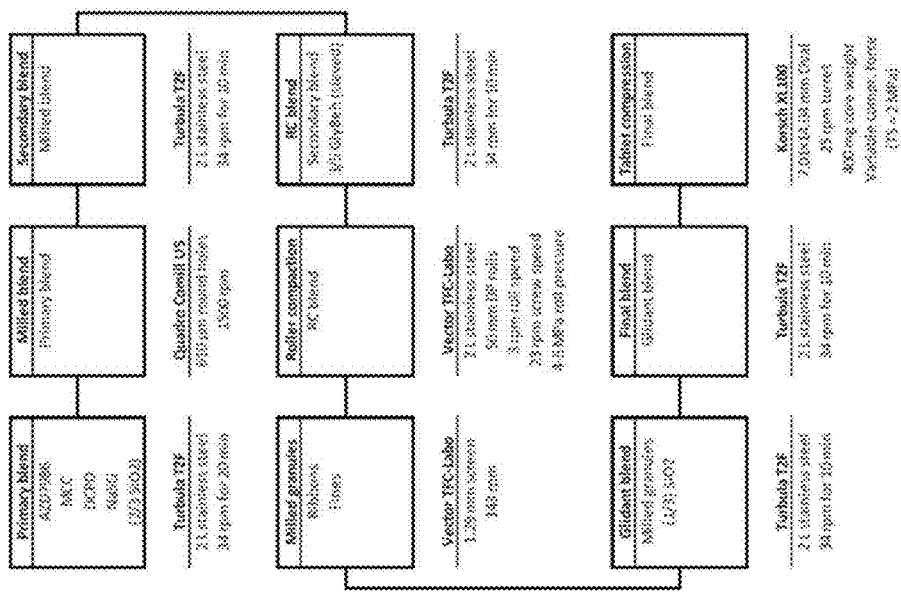
FIG. 5 shows the steps of the manufacturing process that were captured using SEM images.
Figure 6:
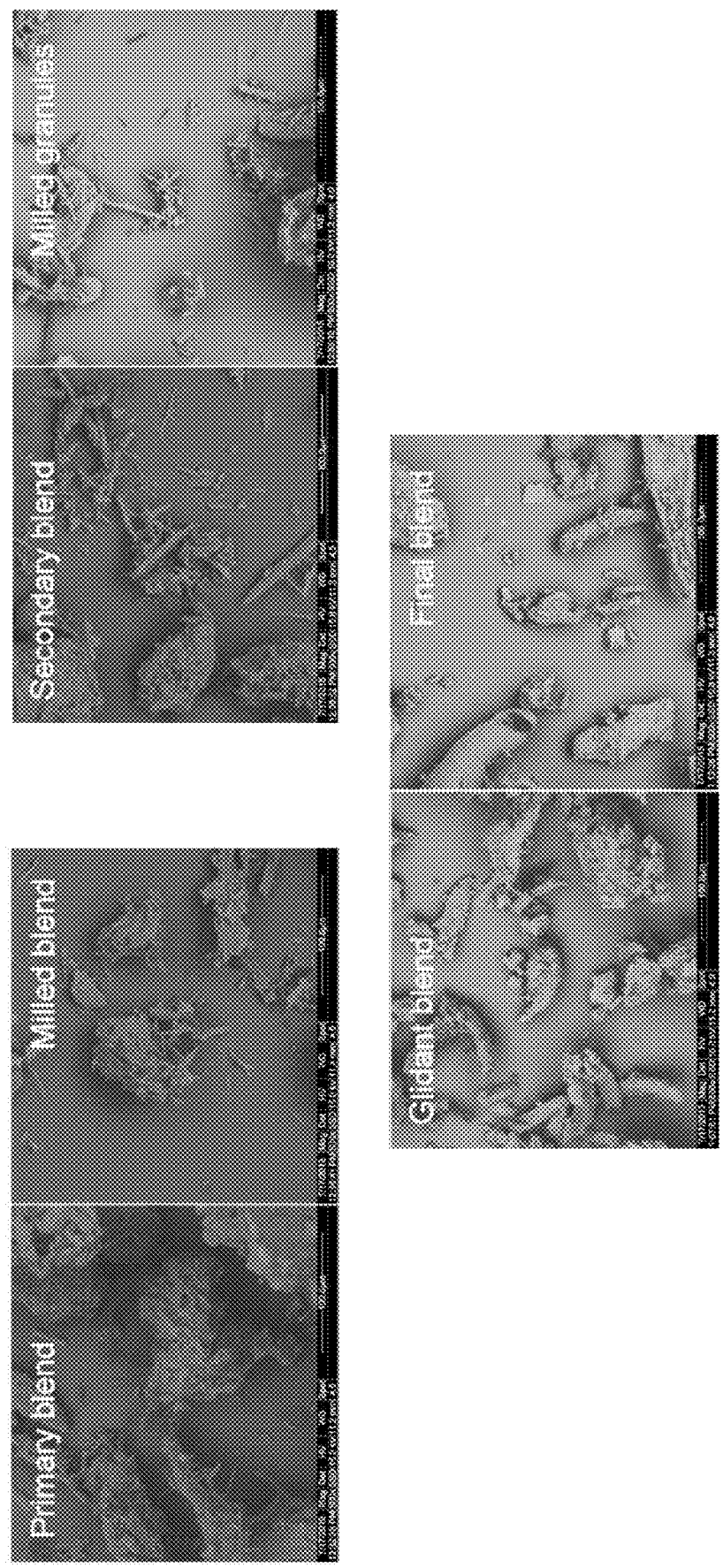
FIG. 6 are scanning electron microscopy (SEM) images of each step of the manufacturing process.

SEM images of each step in the manufacturing processes was captured to better understand the influence of processing route on the final drug product. FIG. 5 shows the steps of the manufacturing process that were captured using SEM images. A selection of SEM images from each step of the manufacturing process are shown in FIG. 6. Based on the results presented herein and the images of the materials from the different steps, the conclusion was drawn that the milled blend and glidant blend steps provide little advantage for the quality of the drug product, but their exclusion from the manufacturing route would improve the manufacturability aspects of the drug product when considering a commercial drug product embodiment.

Figure 7:
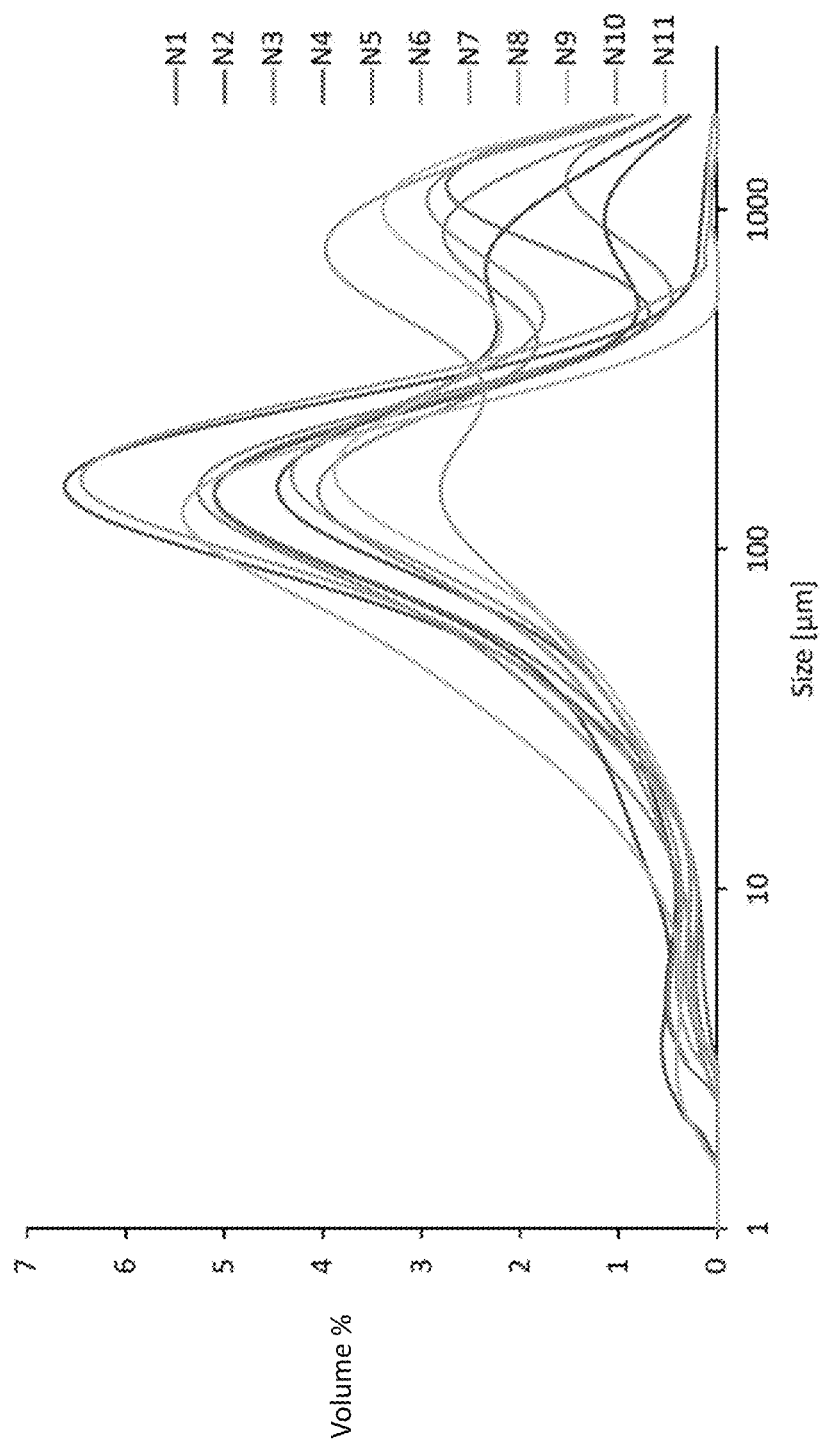
FIG. 7 are graphs of the particle size distribution for the final blends for formulations N1-N11

The particle size distributions (PSDs) for the final blend of all batches are shown in FIG. 7. All distributions are trimodal. There is one hump below 10 μm, which is likely related to uncompacted API. The most prominent peak is just over 100 μm, which is related to uncompacted material. The last peak relates to the amount of granules in the final blend.

The dissolution was immediate for all tested batches, except N1, which still showed rapid dissolution. The drug release was largely unaffected during storage with the exception of batch N1, which showed a significant drop in dissolution after 1 month storage. However, in each condition about 85% dissolved was reached within 20 minutes.

Statistical Evaluation

All results were evaluated using multiple linear regression in an effort to establish models for each response relating the factors of the experimental design. As aforementioned, batch N11 is an outlier compared to the other two center points N9 and N10. In order to construct any relevant models, the results of N11 had to be excluded from all models. N1, which is an extreme corner with low levels of most factors, had to be excluded from the PSD models as well as those related to that, such as granule density. Finally, batch N4 had to be excluded from all models of final drug product, since it was not possible to produce tablets from that batch.

In Table 17, the most relevant models are summarized. The correlation coefficient R2 is a description of how well the data fit the model. The cross-correlation coefficient Q2 is a description of the predictive powder of the model. The columns positive and negative lists the factors significant or near significant to the model, in order of importance. For example, for Powder density DCPD is the most influential factor for increased density of the powder. The amount of Compound A has a negative contribution to the model, meaning that an increased amount of Compound A in the formulation will lead to a decrease in powder bulk density.

TABLE 17

Summary of model statistics

| Response | R2 | Q2 | Positive | Negative | Exclusion |
|---|---|---|---|---|---|
| Powder density | 0.991 | 0.915 | DCPD, SiO2, NaSG | API | N11 |
| Relative density | 0.681 | 0.418 | API, GlyBeh | | N1, N11 |
| Granule density | 0.779 | 0.598 | GlyBeh, SiO2 | | N1, N11 |
| Density increase | 0.987 | 0.953 | API, GlyBeh | DCPD | N1, N11 |
| D[0.5] | 0.923 | 0.311 | GlyBeh, SiO2, RP | DCPD | N1, N11 |
| Span | 0.958 | 0.510 | GlyBeh, RP | APIP, DCPD, NaSG | N1, N11 |
| Mass flow rate | 0.891 | 0.795 | SiO2 | API | N11 |
| Permeability | 0.905 | 0.826 | | API | N11 |
| CPnorm | 0.820 | 0.268 | DCPD, GlyBeh | SiO2 | N4, N11 |
| Disso 1 m 40/75 Open | 0.996 | 0.959 | API, NaSG | GlyBeh | N3, N4, N7, N11 |
| Disso 1 m 40/75 Closed | 0.996 | 0.969 | API, NaSG | GlyBeh | N3, N4, N7, N11 |
| RRT 0.68 1 m | 0.848 | 0.405 | SiO2 | API | N4, N6, N9, N11 |
| RRTs 1.38 1 m | 0.827 | 0.718 | | API | N4, N6, N9, N11 |
| Total degradation (degr) | 0.878 | 0.535 | SiO2 | API | N4, N6, N9, N11 |
| Degr @ 25/60 | 0.860 | 0.698 | | API | N4, N6, N9, N11 |
| Degr @ 40/75 | 0.945 | 0.591 | SiO2 | API, NaSG | N4, N6, N9, N11 |

Increasing amounts of disintegrant improved dissolution. Because the only batch that showed a somewhat lower drug release profile was one batch at the minimum disintegrant level, an amount of disintegrant above that should be sufficient. An increased amount of API was also beneficial to the overall dissolution, while increased lubricant had a detrimental effect on dissolution. The drug load also decreased flowability, but had a positive effect on dissolution.

Figure 8:
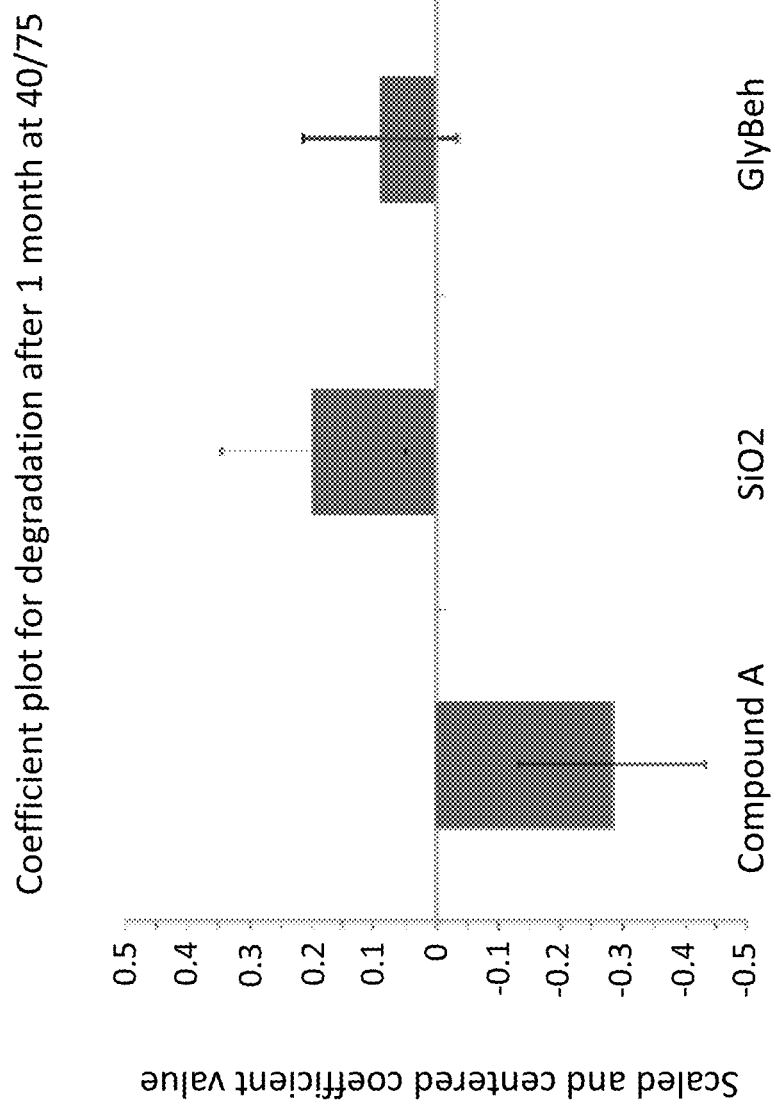
FIG. 8 is a coefficient plot for degradation after 1 month at 40/75.

As for the degradation of the drug product, SiO2 led to an increase in degradation of some peaks, while, as expected a decrease in drug load also increased the overall degradation (see FIG. 8).

Choice of Excipient Levels

DCPD had a minor negative influence on some responses, but is needed to control the strain rate sensitivity of the formulation, thus it was concluded to keep DCPD at the center point level of 20%. NaSG was beneficial for drug release, but the center point level was sufficient to ensure complete dissolution in 15 minutes. The lubricant glyceryl behenate negatively affected compaction properties and dissolution, but had a positive influence on the roller compaction.

The most influential excipient was the silicon dioxide. In this study a hydrated silicon dioxide (Syloid 244FP) was used. Based on the results herein, the SiO2 has a negative impact on degradation. However, SiO2 improved flowability and compaction properties of the formulation. At the lowest drug load, no SiO2 is suggested to be included in the formulation, but as the drug load increases, so does the level of SiO2.

Example 4—Lubricant Screen

Different lubricants and amounts were investigated. Three lubricants were examined and these were glyceryl behenate (GlyBeh), magnesium stearate (MgSt) and stearic acid (StAc). Tablets were produced either by direct compression or using a dry granulation process. After analyzing organic impurities of direct compressed low dose tablets, StAc was excluded from the study since that formulation showed slightly worse degradation profile than the other two.

Three different lubricants were investigated (GlyBeh, MgSt and StAc) and tablets were produced in three different dose strengths (5, 25 and 65 mg). The low-dose tablets were stored in three different conditions, namely 40° C./75 RH (closed), 50° C. (open) and 50° C./75 RH (open). Then two lubricants were selected (GlyBeh and MgSt) and two different dose strengths were produced (5 and 45 mg). Finally, tablets with the final lubricant, GlyBeh, were manufactured in three different dose strengths (4.8, 24 and 43 mg). The final formulations had a drug load of 1.3% to 11.4%, which corresponds to 1.2% to 10.7% when taking purity into account. The tablets were investigated for stability and were stored in five different conditions, namely—20° C., 25° C./60 RH, 30° C./75 RH, 40° C./75 RH and 50° C.

Materials used in this study are provided in Table 19

TABLE 19

Materials used in Example 4.

| Name | Abbreviation | Supplier | Grade |
|---|---|---|---|
| Compound A | API | AstraZeneca | C628/1[a], C628/2[b], C610/2[c] |
| Microcrystalline cellulose | MCC | FMC BioPolymer | Avicel PH-102 |
| Dibasic calcium phosphate dihydrate | DCPD | JRS Pharma | Emcompress |
| Sodium starch glycolate | NaSG | JRS Pharma | Explotab |
| Silicon dioxide | SiO2 | Grace | Siloid 944 FP |
| Glycerol behenate | GlyBeh | Gattefosse | Compritol 888 ATO |
| Stearic Acid | StAc | Peter Greven | Ligamed SA-l-V |
| Coating pre-mix[d] | Coat | Ashland | Aquarius Prime Brown BAP 312542 |

[a]First lubrication trial;
[b]Second lubrication trial;
[c]Third lubrication trial;
[d]pre-mix comprises hypromellose, polyethylene glycol, titanium dioxide and iron oxide red, iron oxide yellow and iron oxide black Equipment and Settings Tablets were manufactured using roller compaction (RC). However, in the first lubrication trial, formulations were direct compressed, except for the 5 mg 1% IG GlyBeh formulation. All other batches were produced using RC. The small pharmaceutical unit operations used for formulations manufactured by RC were blending, co-milling, blending, roller compaction, milling, final blending and compaction, for tablets produced by direct compression the manufacturing steps were blending, co-milling, final blending and compaction. Tablets in supportive stability trial were also film-coated. All equipment and settings are listed in Table 20.

TABLE 20

Equipment and settings used in the Example 4 Study

| Process | Equipment | Settings |
|---|---|---|
| Blending | Turbula T2C | 2 L container size, 30 rpm, 10 + 5[a] or 10[b] min |
| Co-milling | Quadro Comil U5 | 813 μm screen with round openings, 1500 rpm |
| Roller compaction | Vector TFC-Labo | Effective roll width 14 mm, serrated concave-convex rolls, roll speed 3 rpm, feed screw speed 21-24 rpm, roll pressure 5-6 MPa |
| Milling | Vector TFC-Labo | Mill speed 143 rpm, screen size 1.29 mm |
| Final blending | Turbula T2C | 2 L container size, 30 rpm, 10 min |
| Compaction | Korsch EK0[a] | Tooling 10 mm round, target tablet weight 400 mg |
|  | Korsch XL 100[b] | Tooling type B, gravity feeder, tooling 10 mm round, 2 or 5 punches, compaction speed 20 rpm, fill cam 4-10 or 8-14, target tablet weight 400 mg |
| Coating | Vector LDCS | Pan speed 25 rpm, pan size 0.5 L, air flow 60 m³/h, outlet air temperature 40° C., target weight gain percentage 3% |

[a]First lubrication trial;
[b]Second lubrication trial

Blending I

In the first blending step API, MCC, DCPD, NaSG and SiO2 (when present) were mixed in a 2 L container for 10 min at 30 rpm.

Co-Milling

The powder blend was milled to better distribute the silicon dioxide in the blend, ensuring sufficient flow subsequent unit operations. A screen of 813 μm was used to ensure that primary particles remained intact and a speed of 1500 rpm was used to keep the energy exerted on the materials low. No physical change to ingredients has been seen following the co-milling step.

Blending II

At the second blending step 50% of the total amount of lubricant was added (for the first lubrication trial 60% of the total amount of lubricant was added). A pre-blend was prepared by adding the lubricant to a small amount of blend I through a 0.5 mm sieve. The pre-blend was manually mixed and added to Blend I, which was then blended for 5 min (first lubrication trial) or 10 min (second lubrication trial and supportive stability) at 30 rpm. A sample (RC blend) was withdrawn for analysis.

Roller Compaction and Milling

The blend was then roller compacted according to the settings in Table 20. Sample of ribbons were collected during the process. Ribbons and fines were weighed and milled.

Final Blending

At the final blending the remaining 50% (40% for the first lubrication trial) of the total amount of lubricant was added. A pre-blend was prepared by adding the lubricant to a small amount of the granules through a 0.5 mm sieve. The pre-blend was manually mixed and added to the remaining granules, which was then blended for 10 min at 30 rpm. A sample of final blend was withdrawn for analysis.

Compaction

Tablet weight was 400 mg for all batches. The first lubrication trial was compacted with Korsch EK0, the two other trials were compacted with Korsch XL-100. The compaction profile was investigated by compacting the tablets in the second lubrication trial at different compaction forces (low, medium and high). The thickness and breaking force of tablets were measured at each compaction force to establish the relationship between those IPCs and compaction force. The remaining material was compacted to tablets with a tensile strength of 2 MPa, which was true for all material from the first lubrication trial and supportive stability as well.

Film-Coating

Tablets from the supportive stability trial were coated with Ashland pre-mix using Vector LDCS according to the settings in Table 20. The pre-mix was applied as a 10-15% solid suspension in purified water. The amount added is equivalent to an approximate 4.8 mg/cm² weight gain per tablet.

Analyses and Responses

Flow Function Coefficient and Wall Friction Angle

Powder blend withdrawn after blending II was analyzed for flow function coefficient (ffc) and wall friction angle using Schulze Ring Shear tester. The settings used are presented in Table 21, the test was performed once for blends from the supportive stability trial and twice for the other trials. The flow function coefficient was classified according to Jenike. Storage and flow of solids, as seen in Table 22.

TABLE 21

Settings for Schulze ring shear tester

| | Flow function coefficient | Wall friction angle |
|---|---|---|
| Cell | Cell volume: 31.37 cm$^3$ | Wall friction cell |
| Control file | 4000 Pa PreShear.ctf | 4000 Pa PreShear wall test.ctw |
| Load at pre-shear (Pa) | 4000 | 4000 |
| Loads at shear (Pa) | 1000 | 4000 |
| | 1400 | 3200 |
| | 2000 | 2400 |
| | 2600 | 1200 |
| | 1000 | 800 |
| | | 400 |
| Wall friction sample | 0.02 or 0.85 Ra$^a$ | |
| Backing disks | 10 | |

$^a$Ra 0.85 used for supportive stability trial, Ra 0.2 used for the other formulations.

TABLE 22

Classification of ffc

| Ffc | Classification |
|---|---|
| <1 | Not flowing |
| 1-2 | Very cohesive |
| 2-4 | Cohesive |
| 4-10 | Easy flowing |
| >10 | Free-flowing |

Powder Density

The true density of Blend II from the supportive stability trial was analyzed using AccuPyc 1330 with the following settings: 10 ml sample cell, 10 number of purges at purge fill pressure 19.5 psi, 10 runs at run fill pressure 19.5 psi, equilibration rate 0.02 psi/min with the exception that 20 number of purges and 20 runs were used for the 4.8 mg formulation. Two replicates were run.

Ribbon Density

The envelope density of the ribbons was measured using GeoPyc 1360 Envelope Density Analyzer. The analysis was performed in duplicate using the following settings: sample chamber diameter 25.4 mm, number of cycles 5, consolidation force 51 N and conversion factor 0.5153 cm$^3$/mm.

Tablet Properties

Tablets from second lubrication trial and supportive stability trial were analyzed for weight, thickness and breaking force using an Erweka Multicheck Turbo 3 tablet tester (n=10 for tablets from second lubrication trial, n=20 for tablets from supportive stability). The data generated was used to calculate weight variation (% RSD) and tablet tensile strength.

Organic Impurities

Five mg tablets from first lubrication trial (EB15-329701, EB15-329706 and EB15-329704) were investigated for degradation products by UPLC gradient elution analysis of five tablets per sample dissolved in a diluent consisting of water:acetonitrile 50/50 (v/v) with 0.03% TFA added. The sample concentrations were 0.1-0.5 mg/mL. The chromatographic column was either 50 mm or 100 mm long, had an inner diameter of 2.1 mm, and was packed with Waters Acquity BEH C18 particles 1.7 µm. The two mobile phase components were 0.03% TFA in water and 0.03% TFA in acetonitrile. A combination of linear gradient elution and isocratic elution was applied and the total analysis time was 18 minutes. The sample impurity profiles were followed by UV detection at 227 nm.

Dissolution

Tablets with a dose strength of 5 and 65 mg from the first lubrication trial (EB15-329701, EB15-329706, EB15-329704, EB15-329703 and EB15-329707) were analyzed for dissolution. The dissolution test was performed in HCl 0.1 M, at 37° C., using USP apparatus 2 at a rotational speed of 50 rpm using three tablets. Samples were removed at 5, 10, 15, 20, 25, 30, 45, 60, 75, 90, 105 and 120 minutes. At the end of the test the rotational speed was increased to 200 rpm as infinity time points and additional measurements at 135 and 150 minutes were performed. Further information of the settings used are displayed in Table 23.

TABLE 23

Dissolution parameters

| Parameter | Setting |
|---|---|
| Instrument | Automated dissolution workstation, multidose G3 |
| Medium volume (mL) | 1000 |
| Optical path length (mm) | 10 |
| Quantitation wavelength (nm) | 226 nm (5 mg), 277 nm (65 mg) |
| Background correction wavelength (nm) | 350 nm |
| Sampling filter | Millipore automation compatible 25 mm syringe filter, APFB 0.1 um filter (glass fiber pre-filter |
| Sampling volume (mL) | 20 (recirculated back to vessel) |

Roller compaction of 5 mg formulations from the first lubrication trial (EB15-329701, EB15-329706 and EB15-329704) did not work since the powder did not grip on the rolls and robust ribbons could not be formed. This indicates over lubrication of the formulations, which the wall friction angle also indicates. Due to problems with roller compaction all 5 mg formulations were direct compressed and the resulting tablets were analyzed for degradation on stability. Results of organic impurities showed that StAc was the worst choice with respect to degradation products, while GlyBeh had the best profile closely followed by MgSt.

After analyzing organic impurities of low dose formulations, StAc was excluded from the study and the high drug load formulations (65 mg) were produced with GlyBeh and MgSt. Roller compaction of these batches worked rather well. There were no difficulties with the formulation containing MgSt but for the formulation containing GlyBeh there were problems with powder covering the rolls indicating under lubrication (WFA=28°). The RC process had to be stopped and the rolls had to be cleaned during the process.

The dissolution profile of all batches shows that GlyBeh had the fastest dissolution profile followed by MgSt and StAc.

Since the first 5 mg formulations were over lubricated a new 5 mg formulation was produced without lubricant and glidant. Roller compaction of this formulation did not work either, the rolls were squeaking indicating under lubrication. 1% of intra-granular GlyBeh was added and the roller compaction went fine (EB16-257401). However, the ribbons were too thin (relative density <0.5) and further experiments on the amount of lubricant and different process parameters of the roller compactor needs to be investigated.

In the second lubrication trial GlyBeh and MgSt were used as lubricant and formulations with a dose strength of 5 and 45 mg were produced. Roller compaction of these batches proceeded well except for the 45 mg GlyBeh formulation. The powder formed a plug in the orifice to the rolls and the RC process had to be stopped and the funnel and rolls had to be cleaned. When the feeder screw speed was lowered from 24 rpm to 21 rpm and when only a small portion of material was added the RC process progressed in a satisfying way. Data from tablet characterization showed that tablets containing MgSt had a lower tensile strength compared to tablets with GlyBeh. Thus, GlyBeh was chosen as the final lubricant based on the experiences during the manufacturing process and the fact that GlyBeh had a better dissolution profile and tablet tensile strength compared to MgSt.

Supportive Stability

Disintegration, dissolution and organic impurities after three months storage are discussed. Analysis of disintegration was performed using Erweka ZT32 (n=3, MilliQ water, 37° C., without disks).

Results

Ribbon Density and Powder Density

Results of average ribbon density and powder density are presented in Table 24.

TABLE 24

Ribbon density and powder density

| Trial | Sample | Batch ID | Powder density [g/mL] | Ribbon density [g/mL] |
|---|---|---|---|---|
| First lubrication trial | 5 mg w/o lubricant | NA | NT | 1.14 |
| | 5 mg 1% GlyBeh | EB16-257401 | NT | 0.82 |
| | 65 mg MgSt | EB15-329707 | NT | 1.09$^a$ |
| Second lubrication trial | 5 mg GlyBeh | EB16-024901 | NT | 0.92 |
| | 45 mg GlyBeh | EB16-024903 | NT | 0.94 |
| | 5 mg MgSt | EB16-024902 | NT | 1.05$^a$ |
| | 45 mg MgSt | EB16-024904 | NT | 1.07$^a$ |
| Supportive stability | 4.8 mg GlyBeh | EB16-029123 | 1.73 | 1.02 |
| | 24 mg GlyBeh | EB16-029130 | 1.70 | 0.96 |
| | 43 mg GlyBeh | EB16-029134 | 1.67 | 1.14 |

NT Not tested;
$^a$one measurement

Flow Function Coefficient and Wall Friction Angle

Results of flow function coefficient and wall friction angle of Blend Its are presented in Table 25. According to the classification system by Jenike, all Blend Its are classified either as easy-flowing (ffc 4-10) or free-flowing (ffc>10).

TABLE 25

Result of flow function coefficient and wall friction angle

| Trial | Sample | Batch ID | Flow function coefficient | Wall friction angle [°] |
|---|---|---|---|---|
| First lubrication trial | 5 mg w/o lubricant | EB15-329701 | 15.5 | 13.9$^a$ |
| | 5 mg 1% GlyBeh | EB16-257401 | NT | 20.6$^a$ |
| | 5 mg without lubricant | NA | NT | 18.6$^a$ |
| | 25 mg GlyBeh | EB15-329702 | 8.36 | 17.3$^a$ |
| | 65 mg GlyBeh | EB15-329703 | 6.83 | 27.9$^a$ |
| | 5 mg MgSt | EB15-329706 | 23.6 | 11.7$^a$ |
| | 65 MgSt | EB15-329707 | 7.25 | 19.1$^a$ |
| | 5 mg StAc | EB15-329704 | 21.4 | 14.2$^a$ |
| | 65 mg StAc | EB15-329705 | 7.95 | 21.5$^a$ |
| Second lubrication trial | 5 mg GlyBeh | EB16-024901 | NT | 11.2$^a$ |
| | 5 mg MgSt | EB16-024902 | NT | 10.9$^a$ |
| Supportive stability | 4.8 mg GlyBeh | EB16-029123 | 16.0 | 27.7$^b$ |
| | 24 mg GlyBeh | EB16-029130 | 14.1 | 28.1$^b$ |
| | 43 mg GlyBeh | EB16-029134 | 10.6 | 31.1$^b$ |

NT Not tested;
$^a$Ra 0.2;
$^b$Ra 0.85

Tablet Characterization

Figure 9:
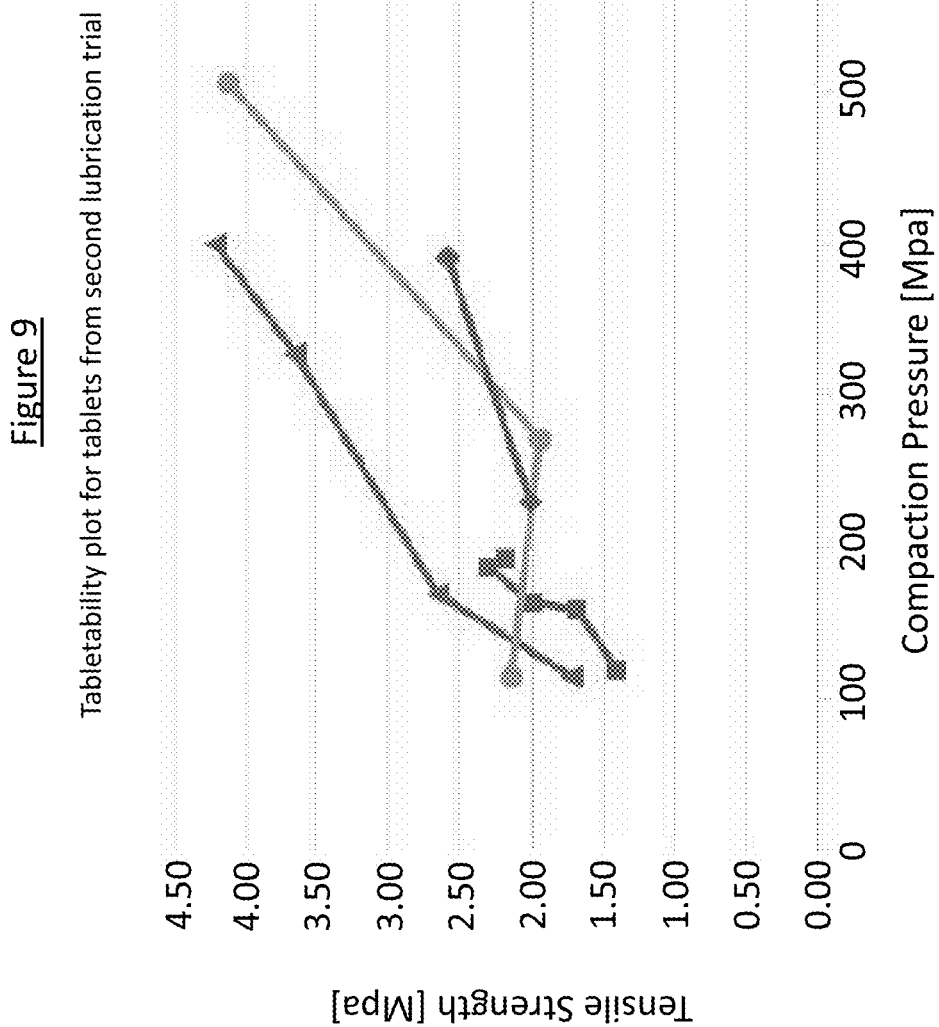
FIG. 9 is a graph of tensile strength (MPa) of tablets from a lubrication trial as a function of compaction pressure (MPa), for various formulations.

Results of tablet properties are summarized as an average in Table 26. In FIG. 9 a plot of compaction pressure and tensile strength of tablets from the second lubrication trial is presented.

The average tablet weight of tablets from the second lubrication trial was high. The average tablet weight for the supportive stability trial was close to nominal and tablet weight variation (RSD) was low for 24 and 43 mg tablets (4.6-1.1), but high for the low dose (3.6%). Regarding compaction of tablets from supportive stability trial, all batches had a rather good flow but were sensitive to adjustments of punch separation and fill depth.

TABLE 26

Tablet properties

| Trial | Sample | Batch ID | Compaction force [kN] | Normalized compaction pressure [MPa] | Tensile strength [MPa] | Tablet weight [mg] | % RSD table weight | Tablet height [mm] |
|---|---|---|---|---|---|---|---|---|
| Second Lubrication trial | 5 mg GlyBeh | EB16-024901 | 8.7 | 133 | 1.71 | 397.2 | 3.14 | 4.56 |
| | 5 mg GlyBeh | EB16-024901 | 12.9 | 127 | 2.66 | 417.7 | 1.43 | 4.60 |
| | 5 mg GlyBeh | EB16-024901 | 24.9 | 179 | 3.66 | 416.2 | 1.38 | 4.45 |
| | 5 mg GlyBeh | EB16-024901 | 30.4 | 190 | 4.21 | 418.2 | 1.34 | 4.36 |
| | 45 mg GlyBeh | EB16-024903 | 8.7 | 106 | 2.15 | 415.7 | 1.23 | 4.72 |
| | 45 mg GlyBeh | EB16-024903 | 20.7 | 278 | 1.95 | 420.3 | 1.84 | 5.01 |
| | 45 mg GlyBeh | EB16-024903 | 38.5 | 245 | 4.13 | 416.5 | 1.27 | 4.35 |
| | 5 mg MgSt | EB16-024902 | 9.1 | 169 | 1.41 | 420.0 | 1.36 | 4.85 |

TABLE 26-continued

Tablet properties

| Trial | Sample | Batch ID | Compaction force [kN] | Normalized compaction pressure [MPa] | Tensile strength [MPa] | Tablet weight [mg] | % RSD table weight | Tablet height [mm] |
|---|---|---|---|---|---|---|---|---|
| | 5 mg MgSt | EB16-024902 | 12.1 | 188 | 1.69 | 420.7 | 1.83 | 4.81 |
| | 5 mg MgSt | EB16-024902 | 12.5 | 164 | 2.00 | 416.3 | 1.41 | 4.63 |
| | 5 mg MgSt | EB16-024902 | 14.2 | 161 | 2.31 | 413.5 | 1.60 | 4.44 |
| | 5 mg MgSt | EB16-024902 | 14.7 | 176 | 2.19 | 422.3 | 1.71 | 4.69 |
| | 45 mg MgSt | EB16-024904 | 17.5 | 227 | 2.02 | 424.7 | 4.70 | 4.50 |
| | 45 mg MgSt | EB16-024904 | 29.8 | 302 | 2.59 | 425.4 | 3.41 | 4.36 |
| Supportive stability | 4.8 mg GlyBeh | EB16-029123 | 10.0 | 111 | 2.37 | 396.2 | 3.61 | 4.39 |
| | 24 mg GlyBeh | EB16-029130 | 12.0 | 128 | 2.45 | 398.5 | 0.63 | 4.42 |
| | 43 mg GlyBeh | EB16-029134 | 12.0 | 137 | 2.29 | 403.5 | 1.06 | 4.42 |

Organic Impurities

The degradation product profiles of 5 mg tablets with the three different lubricants GlyBeh, StAc and MgSt from the first lubrication trial (EB15-329701, EB15-329706 and EB15-329704) stored in 40° C./75 (closed), 50° C. (open) and 50° C./75 (open) for one month were analyzed. Tablets with GlyBeh as lubricant were also analyzed for organic impurities after three months storage in the environments mentioned above.

The organic impurities at time zero was 0.700 in all three 5 mg tablet types corresponding to the impurity profile in the API. Thus, the drug product manufacturing process does not increase degradation products.

Storage for 1 month at 40° C./75%0 RH (closed) resulted in a total organic impurities of 0.9% (GlyBeh), 1.00% (StAc) and 1.10% (MgSt). If the contribution from the API is subtracted an increase in the level of organic impurities was 0.20% (GlyBeh), 0.30% (StAc) and 0.4% (MgSt).

Storage for 1 month at 50° C. (open) resulted in total organic impurities of 2.8% (GlyBeh), 6.7% (StAc) and 3.0% (MgSt). If the contribution from the API is subtracted, an increase in the level of organic impurities was 2.1% (GlyBeh), 6.0% (StAc) and 2.3% (MgSt). The increase of impurities comprised mainly of peaks close to the Compound A peak. The impurity AZ13701214 increased about 0.1% in all three kinds of tablets whereas the two diastereoisomers eluting at 7.7 mins increased significantly in the StAc tablets.

Storage for 1 month in 50° C./75% RH (open) resulted in a total organic impurity level of 4.8% (GlyBeh), 5.0% (StAc) and 4.5% (MgSt). If the contribution from the substance is subtracted an increase in the level of organic impurities was 4.1% (GlyBeh), 4.3% (StAc) and 3.8% (MgSt). The synthesis impurity AZ13701214 increased as well as peaks close to the Compound A peak, and a late eluting impurity at 12 min.

Results of organic impurities after storage in three different conditions for one month revealed that the formulation with StAc as lubricant had a slightly worse degradation profile compared to the other two formulations.

Degradation products of 5 mg tablets with GlyBeh as lubricant (EB15-329701) after three months storage in 40° C./75% (closed), 50° C. (open) and 50° C./75% RH (closed) was also analyzed. After 3 months of storage at 40° C./75% RH (closed), the total amount of impurities had increased from 0.7 area % at time zero to 1.4 area % (0.7 area % (time zero)–0.9 area % (1 month)–1.4 area % (3 months)). AZ13701214 at RRT 0.79 after 3 months increased from 0.3 to 0.5 area %. One of the formamide/diastereoisomers AZ13785488 at RRT 1.31 had increased slightly from 0.2 to 0.3 area % under the same conditions.

After 3 months storage in 50° C. (open) the total impurities had increased from 0.7 area % at time zero to 4.4 area % (0.7 area % (time zero)–2.8 area % (Im)–4.4 area % (3 m)). It was mainly impurities eluting after the Compound A main peak that increased. An impurity at RRT 1.05 increased from <0.05 area % at time zero to 1.0 area % after 3 months. The formamide diastereoisomers AZ13785488 and AZ13910537 at RRT 1.30 and RRT 1.31 had increased from 0.2 area % to 0.7 and 0.8 area % respectively.

After 3 months storage at 50° C./75% RH (open) the total impurities had increased from 0.7 area % at time zero to 9.9 area % (0.7 area % (time zero)–4.8 area % (Im)–9.9 area % (3 m)). Under those conditions the increase in impurities eluting both before and after the Compound A main peak was seen. The impurity AZ13701214 at RRT 0.79, for example, increased from 0.3 area % at time zero to 2.5 area % after 3 months. Other impurities eluting at RRT 0.9 and 1.1 increased from <0.05 area % at time zero to about 1.4 area % after 3 months storage.

The synthesis by-product AZ13905472 eluting at RRT 0.76 just in front of AZ13701214, having a low UV-absorbance at 227 nm, was shown to be uninfluenced by the different tablet compositions and storage conditions.

The total amount of organic impurities increased 0.5 area % after closed storage for 3 months in 40° C./75% RH. Open storage for 3 months in 50° C. increased the total amount of impurities 3.7 area % and 9.2 area % in 50° C./75% RH.

Dissolution
First Lubrication Trial

Figure 10:
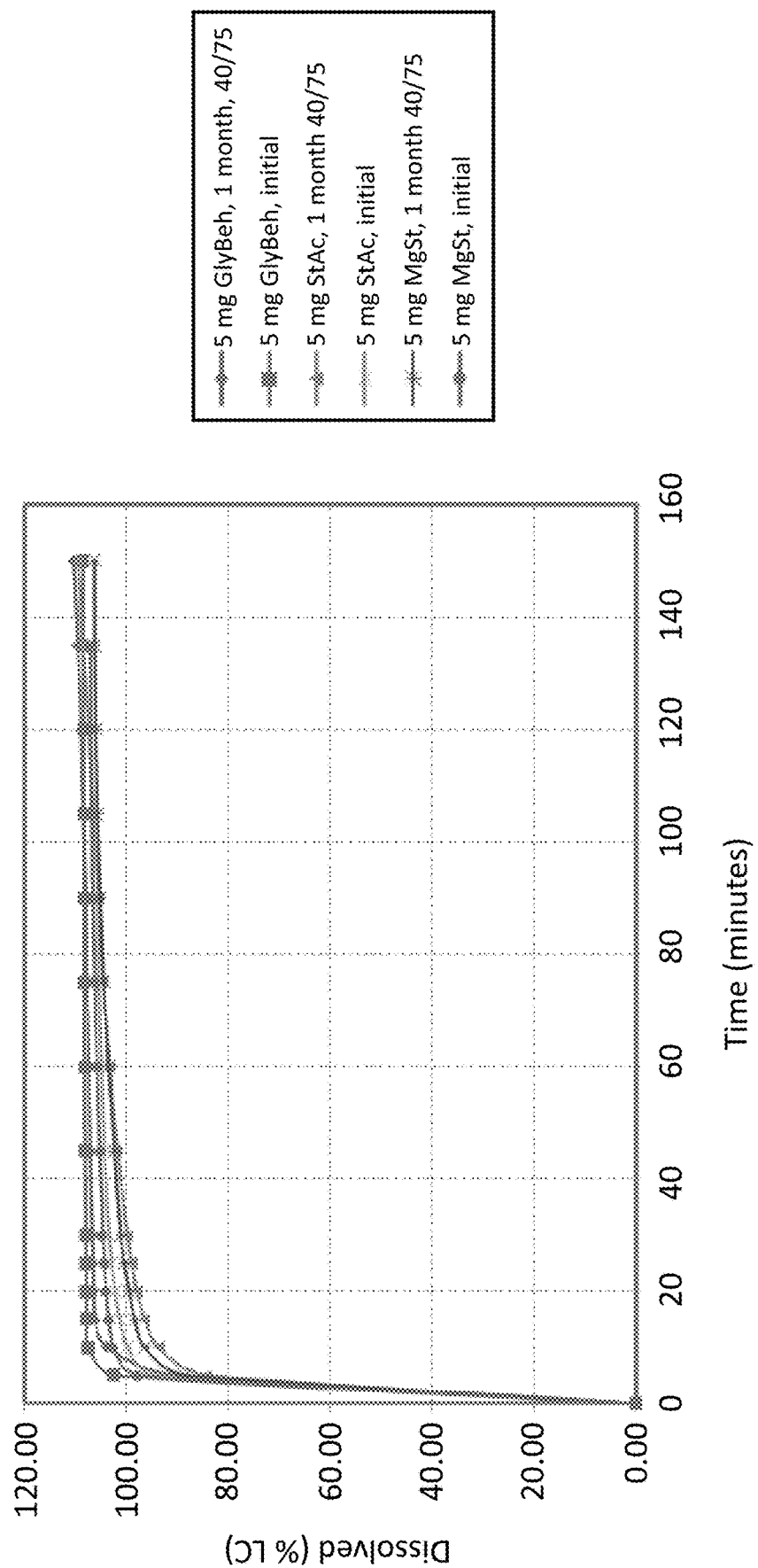
FIG. 10 is a dissolution profile of 5 mg formulation from the first lubrication trial at initial state and after storage in 40/75 for one month.
Figure 11:
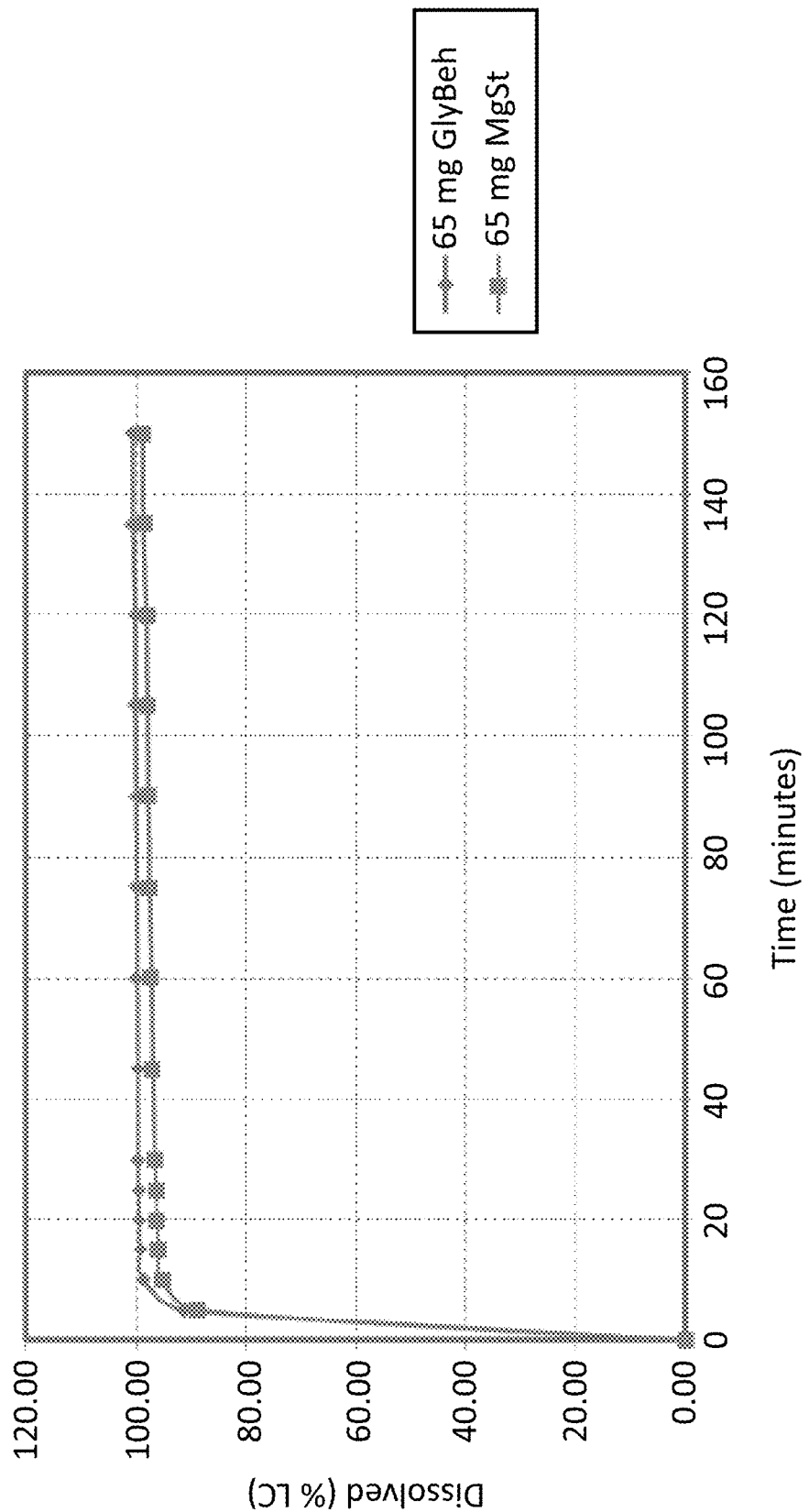
FIG. 11 is a dissolution profile of 65 mg formulation from the first lubrication trial at initial state.

Dissolution profile of tablets from the first lubrication trial are presented in FIG. 10 and FIG. 11. In FIG. 10, results from 5 mg tablets (EB15-329701, EB15-329706 and EB15-329704) at initial conditions and after storage in 40° C./75 for one month are presented. In FIG. 11, results of 65 mg tablets (EB15-329703 and EB15-329707) at initial state is shown. The dissolution is rapid for both dose strengths, 80% is dissolved within 10 min.

Supportive Stability—Organic Impurities

Results of the analysis of organic impurities of tablets stored in −20° C., 25° C./60, 40° C./75 and 50° C. for one and three months are presented in Table 27, Table 28 and Table 29, for 4.8, 24 and 43 mg, respectively. All detectable peaks were within specification.

TABLE 27

Organic impurities of 4.8 mg (EB16-029123) at initial stage and after one and three months storage 4.8 mg

|  | Initial | −20° C. 1 month | 25° C./ 60% RH 1 month | 40° C./ 75% RH 1 month | 50° C. 1 month | −20° C. 3 months | 25° C./ 60% RH 3 months | 40° C./ 75% RH 3 months | 50° C. 3 months |
| --- | --- | --- | --- | --- | --- | --- | --- | --- | --- |
| AZ13701214 | <0.05 | NT | <0.05 |  |  | <0.05 | <0.05 |  | <0.05 |
| AZ14102478 | ND | NT | ND | ND | 0.08 | ND | ND | ND | ND |
| AZ13785488 | 0.14 | NT | 0.15 | 0.20 | 0.36 | 0.13 | 0.13 | 0.24 | 0.14 |
| AZ13910537 | 0.13 | NT | 0.14 | 0.18 | 0.27 | 0.13 | 0.13 | 0.21 | 0.32 |
| Total | 0.95 | NT | 0.95 | 1.11 | 1.74 | 0.87 | 0.85 | 1.46 | 2.33 |

TABLE 28

Organic impurities 24 mg (EB16-029130) at initial stage and after one and three months storage

|  | Initial | 25° C./ 60% RH 1 | 40° C./ 75% RH 1 | 25° C./ 60% RH 3 months | 40° C./ 75% RH 3 months |
| --- | --- | --- | --- | --- | --- |
| AZ13701214 | <0.05 | NT | 0.05 | <0.05 | 0.13 |
| AZ14102478 | ND | NT | ND | ND | 0.05 |
| AZ13785488 | 0.12 | NT | 0.14 | 0.14 | 0.17 |
| AZ13910537 | 0.11 | NT | 0.13 | 0.12 | 0.15 |
| Total | 0.89 | NT | 0.96 | 0.81 | 1.16 |

TABLE 29

Organic impurities of 43 mg (EB16-029134) at initial stage and after one and three months storage

|  | Initial | −20° C. 1 month | 25° C./ 60% RH 1 month | 40° C./ 75% RH 1 month | 50° C. 1 month | −20° C. 3 months | 25° C./ 60% RH 3 months | 40° C./ 75% RH 3 months | 50° C. 3 months |
| --- | --- | --- | --- | --- | --- | --- | --- | --- | --- |
| AZ13701214 | <0.05 | NT | <0.05 | 0.05 | 0.16 | <0.05 | <0.05 | 0.13 | 0.22 |
| AZ14102478 | ND | NT | ND | ND | 0.07 | ND | ND | 0.06 | 0.11 |
| AZ13785488 | 0.11 | NT | 0.13 | 0.14 | 0.16 | 0.114 | 0.12 | 0.15 | 0.17 |
| AZ13910537 | 0.11 | NT | 0.11 | 0.13 | 0.15 | 0.10 | 0.11 | 0.13 | 0.16 |
| Total | 0.82 | NT | 0.94 | 0.93 | 1.22 | 0.77 | 0.79 | 1.08 | 1.31 |

Dissolution

In Table 30, results of dissolution at initial state and after three months storage in −20° C., 25° C./60, 40° C./75 and 50° C. are presented for all dose strengths. The result is presented as the average of 3 measurements (six for initial state) and the reported value is the time read at 15 min. The dissolution is rapid for all dose strengths in all conditions and at 15 min close to 100% is dissolved for all batches.

TABLE 30

Dissolution (% of label claim) after 3 months storage.

| Dose [mg] | Initial | −20° C. | 25° C./ 60% RH | 40° C./ 75% RH | 50° C. |
| --- | --- | --- | --- | --- | --- |
| 4.8 | 103 | 98 | 98 | 98 | 99 |
| 24 | 94[a] | 98 | 100 | 98 | 99 |
| 43 | 96[b] | 99 | 99 | 100 | 100 |

[a]The test was performed using uncoated tablets and modified method, 900 mL media and with 50 rpm instead of 1000 mL media and with 75 rpm.
[b]2 measurements Disintegration In Table 31, results of disintegration time(s) of coated tablets stored in five different conditions for three months are presented as the maximum of three tablets. The disintegration time was quick for all batches (within 4 min 10 s), the time increased with increasing drug load and increasing temperature/humidity.

TABLE 31

Disintegration time(s) at initial stage and after 3 months storage.

| Dose [mg] | Initial | −20° C. | 25° C./ 60% RH | 30° C./ 75% RH | 40° C./ 75% RH | 50° C. |
|---|---|---|---|---|---|---|
| 4.8 | 19[a] | 64 | 70 | 70 | 94 | 115 |
| 24 | 20[a] | 70 | 62 | 76 | 100 | 144 |
| 43 | 33[a] | 90 | 95 | 121 | 145 | 247 |

[a]Uncoated tablet

A non-functional aesthetic hypromellose-based film coat is used as coating agent. In order to ensure good coating coverage regardless of tablet size, the amount of film coat is varied based on the tablet surface area. Approximately 4.8 mg/cm² of film coat is applied on the drug product, corresponding to 3% for a tablet core of 400 mg (10 mm normal concave round used herein) and 3.3% for a tablet core of 300 mg (9 mm normal concave round).

The composition of the three manufactured supportive stability batches are displayed in Table 32.

TABLE 32

Components in Compound A Supportive Stability Batches

| Component | Amount in 4.8 mg formulation [%] | Amount in 24 mg formulation [%] | Amount in 43 mg formulation [%] |
|---|---|---|---|
| Compound A | 1.2[a] (1.3)[b] | 6.0[a] | 10.7[a] (11.4)[b] |
| Microcrystalline cellulose | 72.7 | 65.8 | 59.3 |
| Dibasic calcium phosphate dihydrate | 20.0 | 19.8 | 19.7 |
| Sodium starch glycolate | 4.0 | 4.0 | 3.9 |
| Colloidal Silicon dioxide | 0.0 | 0.15 | 0.30 |
| Glyceryl behenate | 2.2 | 4.3 | 6.1 |

[a]The amount of drug substance is adjusted to take into account the purity of AZD7896 free base
[b]The amount of drug substance without taking purity into account

Example 5—Exemplary Compositions

For a 400-mg tablet, a dosage form comprising 45 mg of Compound A would have a 11.25% drug load for a 400-mg tablet) and 5 mg Compound A (1.25% drug load for a 400-mg tablet). Since the lowest possible dose was 5 mg, a drug load of 1.25% would be needed for the same 400-mg core weight. The drug product contains Compound A as drug substance, microcrystalline cellulose and dibasic calcium phosphate dihydrate as diluents, sodium starch glycolate as disintegrant, silicon dioxide as glidant and glyceryl behenate as lubricant. Glyceryl behenate is added both intra and extra-granularly. In order to deliver size-matched drug product for clinical studies, silicon dioxide and glyceryl behenate is varied with drug load to balance the cohesive and adhesive properties of the formulation, while maintaining good drug product stability. Also, the amount of microcrystalline cellulose is changed to obtain the target weight of the drug product as well as to correct for the drug substance purity. The amount of each component is calculated according to Table 33. Composition of tablet cores is presented in Table 34.

TABLE 33

Components in Compound A Formulation

| Component | Amount [%] |
|---|---|
| Compound A | Dose [mg]/core weight [mg] × 100 |
| Microcrystalline cellulose | 100 − sum of other components [%] |
| Dibasic calcium phosphate dihydrate | 20.0 |
| Sodium starch glycolate | 4.0 |
| Silicon dioxide | 0.03 × Compound A [%] − 0.05 (0.00 if Compound A ≤ 1.67%) |
| Glyceryl behenate | 0.36 × Compound A [%] + 1.5 |
| Coat | 4.8 [mg/cm²] |

TABLE 34

Composition of tablet cores

| Component | Amount in lowest drug load table core [%] | Amount in highest drug load table core [%] |
|---|---|---|
| Compound A | 1.2[a] | 11.4[a] |
| Microcrystalline cellulose | 72.9[a] | 58.7[a] |
| Dibasic calcium phosphate dihydrate | 20.0 | 20.0 |
| Sodium starch glycolate | 4.0 | 4.0 |
| Silicon dioxide | 0.0 | 0.3 |
| Glyceryl behenate | 1.9 | 5.6 |

[a]Adjusted to take purity into account

Figure 12:
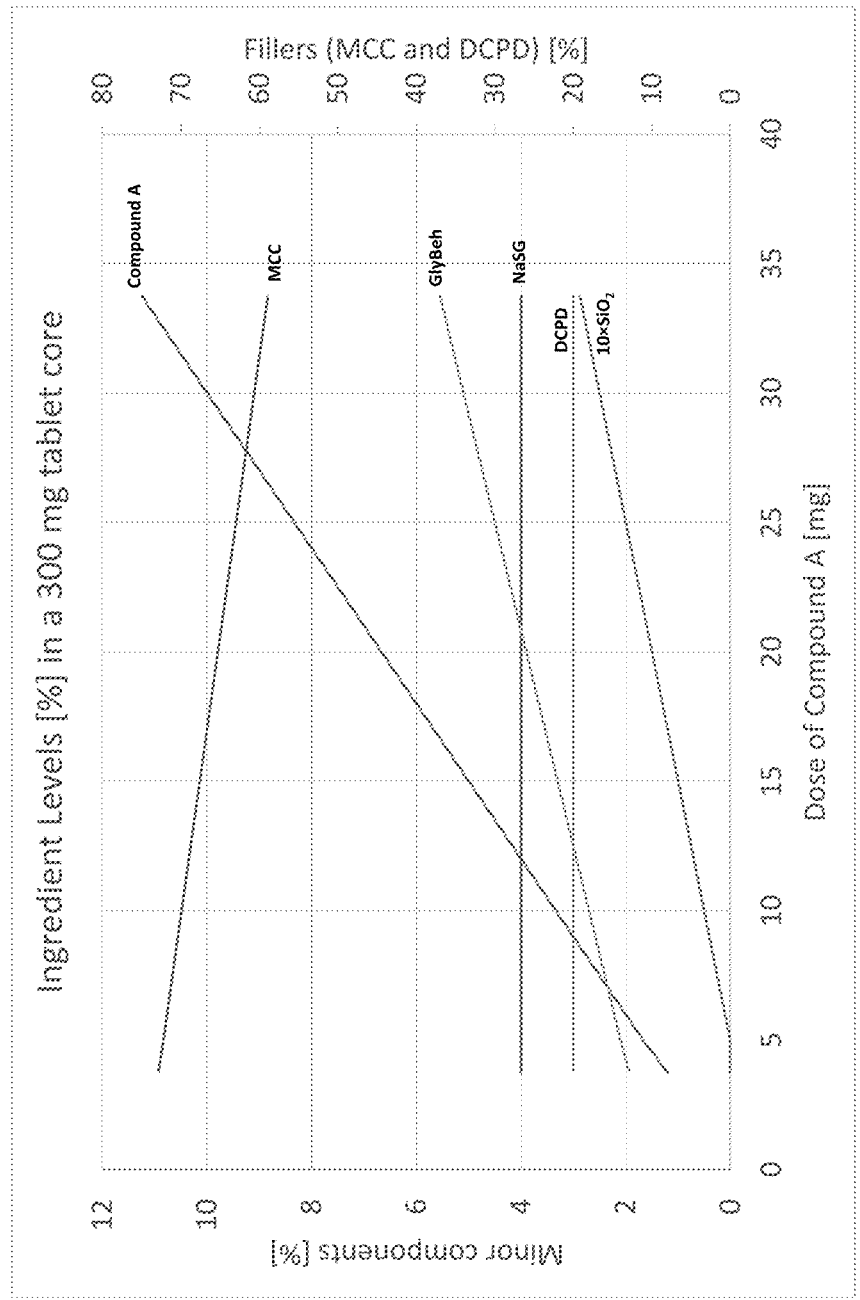
FIG. 12 is a graph of excipient levels (percentage of core weight) as a function of API dose.

Exemplary compositions, e.g., 10 mg, 25 mg and 40 mg compositions of Compound A are provided in FIG. 12 and Tables 35, 36, 38 and 39 and 36, below.

TABLE 35

Exemplary 10 mg Formulation

| Component | Quantity per unit (mg) | Quantity per Batch (g) |
|---|---|---|
| Tablet Core | | |
| Compound A | 10.0[a] | 500 |
| Microcrystalline cellulose/Cellulose, microcrystalline | 210[a] | 10488 |
| Dibasic calcium phosphate dihydrate/Calcium hydrogen phosphate dihydrate | 60.0 | 3000 |
| Sodium starch glycolate, Type A | 12.0 | 600 |
| silicon dioxide | 0.15 | 7.5 |
| Glyceryl behenate/Glycerol dibehenate | 8.1 | 405 |
| Tablet core weight | 300 | 15000 |
| Tablet Coat | | |
| Hypromellose | 6.25[b] | 313[b] |
| Polyethylene glycol/Macrogels | 1.25[b] | 62.5[b] |
| Titanium dioxide | 1.45[b] | 72.5[b] |
| Ferric oxide red/Red iron oxide | 0.30[b] | 15.0[b] |
| Ferric oxide yellow/Yellow iron oxide | 0.55[b] | 27.5[b] |
| Ferric oxide black/Black iron oxide | 0.20[b] | 10.0[b] |

TABLE 35-continued

Exemplary 10 mg Formulation

| Component | Quantity per unit (mg) | Quantity per Batch (g) |
|---|---|---|
| Purified water/Water, purified | 73.3[c] | 3667[c] |
| Coated tablet weight | 310 | 15500 |

[a] The amount of drug substance will be adjusted to take into account the purity of the Compound A free base. The amount of microcrystalline cellulose will then be adjusted accordingly to maintain the same tablet weight.
[b] May be added as a proprietary coating pre-mix, e.g., Aquarius Prime BAP312542, in a 10% to 15% solid suspension with purified water.
[c] Purified water is used as the solvent/carrier fluid during film coating and is removed during the process. The amount of water corresponds to that of a 12% solid suspension.

TABLE 36

Exemplary 10 mg Formulation

| Component | Quantity per unit (mg) | Quantity per Batch (g) |
|---|---|---|
| Tablet Core | | |
| Compound A | 10.0[a] | 500 |
| Microcrystalline cellulose/Cellulose, microcrystalline | 204[a] | 10200 |
| Dibasic calcium phosphate dihydrate/Calcium hydrogen phosphate dihydrate | 60.0 | 3000 |
| Sodium starch glycolate, Type A | 12.0 | 600 |
| silicon dioxide | 0.60 | 7.5 |
| Glyceryl behenate/Glycerol dibehenate | 13.5 | 405 |
| Tablet core weight | 300 | 15000 |
| Tablet Coat | | |
| Hypromellose | 6.25[b] | 313[b] |
| Polyethylene glycol/Macrogels | 1.25[b] | 62.5[b] |
| Titanium dioxide | 1.45[b] | 72.5[b] |
| Ferric oxide red/Red iron oxide | 0.30[b] | 15.0[b] |
| Ferric oxide yellow/Yellow iron oxide | 0.55[b] | 27.5[b] |
| Ferric oxide black/Black iron oxide | 0.20[b] | 10.0[b] |
| Purified water/Water, purified | 73.3[c] | 3667[c] |
| Coated tablet weight | 310 | 15500 |

[a] The amount of drug substance will be adjusted to take into account the purity of the Compound A free base. The amount of microcrystalline cellulose will then be adjusted accordingly to maintain the same tablet weight.
[b] May be added as a proprietary coating pre-mix, e.g., Aquarius Prime BAP312542, in a 10% to 15% solid suspension with purified water.
[c] Purified water is used as the solvent/carrier fluid during film coating and is removed during the process. The amount of water corresponds to that of a 12% solid suspension.

TABLE 37

Exemplary 25 ms Formulation

| Component | Quantity per unit (mg) | Quantity per Batch (g) |
|---|---|---|
| Tablet Core | | |
| Compound A | 25.0[a] | 1250[a] |
| Microcrystalline cellulose/Cellulose, microcrystalline | 189[a] | 9445[a] |
| Dibasic calcium phosphate dihydrate/Calcium hydrogen phosphate dihydrate | 60.0 | 3000 |
| Sodium starch glycolate, Type A | 12.0 | 600 |
| silicon dioxide | 0.60 | 30 |
| Glyceryl behenate/Glycerol dibehenate | 13.5 | 675 |
| Tablet core weight | 300 | 15000 |
| Tablet Coat | | |
| Hypromellose | 6.25[b] | 313[b] |
| Polyethylene glycol/Macrogels | 1.25[b] | 62.5[b] |
| Titanium dioxide | 1.45[b] | 72.5[b] |
| Ferric oxide red/Red iron oxide | 0.30[b] | 15.0[b] |
| Ferric oxide yellow/Yellow iron oxide | 0.55[b] | 27.5[b] |
| Ferric oxide black/Black iron oxide | 0.20[b] | 10.0[b] |
| Purified water/Water, purified | 73.3[c] | 3667[c] |
| Coated tablet weight | 310 | 15500 |

[a] The amount of drug substance will be adjusted to take into account the purity of the Compound A free base. The amount of microcrystalline cellulose will then be adjusted accordingly to maintain the same tablet weight.
[b] May be added as a proprietary coating pre-mix, e.g., Aquarius Prime BAP312542, in a 10% to 15% solid suspension with purified water.
[c] Purified water is used as the solvent/carrier fluid during film coating and is removed during the process. The amount of water corresponds to that of a 12% solid suspension.

TABLE 38

Exemplary 40 mg Formulation

| Component | Quantity per unit (mg) | Quantity per Batch (g) |
|---|---|---|
| Tablet Core | | |
| Compound A | 40.0[a] | 1250[a] |
| Microcrystalline cellulose/Cellulose, microcrystalline | 174[a] | 8700[a] |
| Dibasic calcium phosphate dihydrate/Calcium hydrogen phosphate dihydrate | 60.0 | 3000 |
| Sodium starch glycolate, Type A | 12.0 | 600 |
| silicon dioxide | 0.60 | 30 |
| Glyceryl behenate/Glycerol dibehenate | 13.5 | 675 |
| Tablet core weight | 300 | 15000 |
| Tablet Coat | | |
| Hypromellose | 6.25[b] | 313[b] |
| Polyethylene glycol/Macrogels | 1.25[b] | 62.5[b] |
| Titanium dioxide | 1.45[b] | 72.5[b] |
| Ferric oxide red/Red iron oxide | 0.30[b] | 15.0[b] |
| Ferric oxide yellow/Yellow iron oxide | 0.55[b] | 27.5[b] |
| Ferric oxide black/Black iron oxide | 0.20[b] | 10.0[b] |
| Purified water/Water, purified | 73.3[c] | 3667[c] |
| Coated tablet weight | 310 | 15500 |

[a] The amount of drug substance will be adjusted to take into account the purity of the Compound A free base. The amount of microcrystalline cellulose will then be adjusted accordingly to maintain the same tablet weight.
[b] May be added as a proprietary coating pre-mix, e.g., Aquarius Prime BAP312542, in a 10% to 15% solid suspension with purified water.
[c] Purified water is used as the solvent/carrier fluid during film coating and is removed during the process. The amount of water corresponds to that of a 12% solid suspension.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A pharmaceutical composition comprising:
   (a) from about 3 wt % to about 10 wt % of (2S)-N-{(1S)-1-cyano-2-[4-(3-methyl-2-oxo-2,3-dihydro-1,3-benzoxazol-5-yl)phenyl] ethyl}-1,4-oxazepane-2-carboxamide (Compound A);

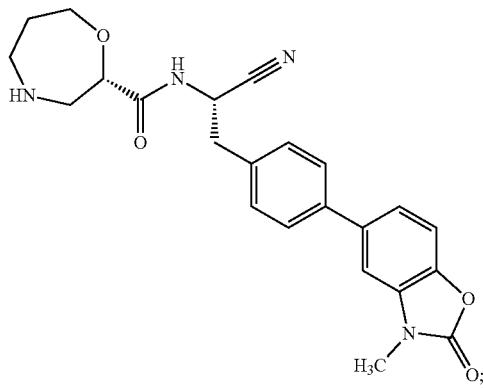 [SMILES: Cn1c(=O)oc2ccc(-c3ccc(C[C@@H](C#N)NC(=O)[C@@H]4CNCCCO4)cc3)cc21]

(b) from about 55 wt % to about 70 wt % microcrystalline cellulose, acting as a pharmaceutical diluent;
   (c) from about 18 wt % to about 22 wt % dibasic calcium phosphate dihydrate, acting as a compression aid;
   (d) from about 3.5 wt % to about 4.5 wt % sodium starch glycolate, acting as a pharmaceutical disintegrant;
   (e) from about 0.05 wt % to about 0.25 wt % silicon dioxide, acting as a pharmaceutical glidant;
   (f) from about 2.5 wt % to about 4.5 wt % glycerol behenate, acting as a pharmaceutical lubricant;
   and wherein the weights of the components (a)-(f) add up to 100 wt %.

2. The pharmaceutical composition of claim 1, wherein the composition is in tablet form.

3. The pharmaceutical composition of claim 2, wherein the composition further comprises a tablet coat.

4. The pharmaceutical composition of claim 1, wherein Compound (A) is present at from about 5 mg to about 50 mg in the composition.

5. The pharmaceutical composition of claim 1, wherein Compound (A) is present at from about 10 mg to about 40 mg in the composition.

6. The pharmaceutical composition of claim 1, wherein Compound (A) is present at 10 mg in the composition.

7. The pharmaceutical composition of claim 1, wherein Compound (A) is present at 25 mg in the composition.

8. The pharmaceutical composition of claim 1, wherein Compound (A) is present at 40 mg in the composition.

* * * * *